US006475745B1

(12) United States Patent
Giulian

(10) Patent No.: US 6,475,745 B1
(45) Date of Patent: *Nov. 5, 2002

(54) IDENTIFICATION OF AGENTS THAT PROTECT AGAINST INFLAMMATORY INJURY TO NEURONS

(75) Inventor: Dana Giulian, Houston, TX (US)

(73) Assignee: Baylor College of Medicine, Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/922,889

(22) Filed: Sep. 3, 1997

Related U.S. Application Data

(62) Division of application No. 08/717,551, filed on Sep. 20, 1996.

(51) Int. Cl.[7] .......................... G01N 33/53; C07K 7/00; C07K 4/12
(52) U.S. Cl. ...................... 435/7.2; 530/300; 530/350; 530/402
(58) Field of Search .................. 435/7.2, 7.1; 530/300, 530/350, 402; 424/450

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,728,605 A | 3/1988 | Fudenberg et al. | 435/29 |
| 4,800,159 A | 1/1989 | Mullis et al. | 435/172.3 |
| 4,801,533 A | 1/1989 | Fudenberg | 435/7 |
| 4,919,915 A | 4/1990 | Averback | 424/7.1 |
| 5,134,062 A | 7/1992 | Blass | 435/7.21 |
| 5,221,607 A | 6/1993 | Cordell et al. | 435/6 |
| 5,231,000 A | 7/1993 | Majocha et al. | 435/7.1 |
| 5,348,963 A | 9/1994 | Gandy et al. | 514/313 |
| 5,430,039 A | 7/1995 | Roberts-Lewis et al. | 514/297 |
| 5,434,050 A * | 7/1995 | Maggio et al. | |
| 5,538,845 A | 7/1996 | Knops et al. | 435/6 |
| 5,547,841 A | 8/1996 | Marotta et al. | 435/6 |
| 5,578,451 A | 11/1996 | Nishimoto | 435/7.1 |
| 5,593,846 A | 1/1997 | Schenk et al. | 435/7.9 |
| 5,604,102 A | 2/1997 | McConlogue et al. | 435/7.1 |

FOREIGN PATENT DOCUMENTS

| | | |
|---|---|---|
| CA | 2116460 | 9/1994 |
| EP | 329822 | 8/1988 |
| EP | 320308 | 12/1988 |
| GB | 2 202 328 | 3/1988 |
| JP | 06329551 A | 11/1994 |
| WO | WO 87/06270 | 4/1987 |
| WO | WO 88/10315 | 6/1988 |
| WO | WO 89/06700 | 1/1989 |
| WO | WO 89/09284 | 3/1989 |
| WO | WO 90/05138 | 5/1990 |
| WO | WO 94/01772 | 1/1994 |
| WO | WO 94/07144 | 3/1994 |
| WO | WO 96/12736 | 5/1996 |

OTHER PUBLICATIONS

Ii et al., Brain Research 720: 93–100, May 1996.*
Harrigan et al., Neurobiol. Aging 16: 779–789, 1995.*
Arimatsu et al., Devel. Brain Research 58: 189–201, 1991.*
Mattson et al., Trends Neurosci. 16: 409–414, 1993.*
Rohr AE, et. al, J. of Biol Chem, V. 271, No. 34, pp. 20631–20635, Aug. 1996.*
Pike et al, J. Neurochem., 66, 1374–82, Apr. 1996.*
McGeer, Br. Res Rev, 21, pp. 195–218, Dec. 1995.*
Pike et al, Neuroscience, V. 63, No. 2, pp. 517–531, 1994.*
Skolnick et al., Trends in Biotech 18(1):34–39, 2000.*
Abstract, Kim et al., Mol. Biol of the Cell 5(7), 1994.*
Abstract, Baird et al., Biochem. & Biophys. Res. Comm., 142(2), 1987.*
Eikelboom, P. et al., "Cerebral amyloid plaques in Alzheimer's disease but not in scrapie–affected mice are closely associated with a local inflammatory process", *Virchows Archiv Cell. Path.*, 1991, 60(5), 329–339.
Gehrmann, J. et al., "Reactive microglia in cerebral ischaemia: an early mediator of tissue damage?", *Neuropath. Appl. Neurobiol.*, 1995, 21, 277–289.
Giulian, D. et al., "Specific Domains of β–Amyloid from Alzheimer Plaque Elicit Neuron Killing in Human Microglia", *J. Neurosc.*, 1996, 16(19), 6021–6037.
Kalaria, R. et al., "Cellular Aspects of the Inflammatory Response in Alzheimer's Disease", *Neurodegeneration*, 1996, 5(4), 497–503.
Khoury, J. et al., "Scavenger receptor–mediated adhesion of microglia to β–amyloid fibrils", *Nature*, 1996, 382, 716–719.
McGeer, P. et al., "The inflammatory response system of brain: implications for therapy for Alzheimer and other neurodegenerative diseases", *Brain Res. Rev.*, 1995, 21, 195–218.
Meda, L. et al., "β–Amyloid (25–35) Peptide and IFN–γSynergistically Induce the Production ofthe Chemotactic Cytokine MCP–1/JE in Monocytes and Microglial Cells", *J. Immunol.*, 1996, 157, 1213–1218.

(List continued on next page.)

*Primary Examiner*—Gary L. Kunz
*Assistant Examiner*—Sharon Turner
(74) *Attorney, Agent, or Firm*—Vinson & Elkins L.L.P.

(57) ABSTRACT

The present invention is directed to screening for an agent that inhibits the effect of a neurotoxin from a plaque component activated mononuclear phagocyte on a neuron. In addition, the present invention is directed to methods of screening for agents that inhibit mononuclear phagocyte-plaque component complex formation, plaque component activation of a mononuclear phagocyte, plaque component induced neurotoxicity of a mononuclear phagocyte. An agent obtained by the method of screening for an agent that inhibits mononuclear phagocyte-plaque component complex formation and a pharmaceutical composition comprising the agent are embodied by the present invention.

23 Claims, 38 Drawing Sheets

OTHER PUBLICATIONS

Siripont, J. et al., "Receptor–Mediated Binding of the Acute–Phase Reactant Mouse Serum Amyloid P–Component (SAP) to Macrophages", *Cell. Immunol.*, 1988, 117(2), 239–252.

Wright, S. et al., "Fibronectin and Serum Amyloid P Component Stimulate C3b–and C3bi–Mediated Phagocytosis in Cultured Human Monocytes", *J. Exp. Med.*, 1983, 158, 1338–1343.

Banati et al., "Cytotoxicity of Microglia", *Glia*, 1993, 7, 111–118.

Bansal et al., "Multiple and Novel Specificities of Monoclonal Antibodies 01, 04, and R–mAb Used in the Analysis of Oligodendrocyte Development", *J. Neurosci. Res.*, 1989, 24, 548–557.

Beckman et al., "Apparent hydroxyl radical production by peroxynitrite: Implications for endothelial injury from nitric oxide and superoxide", *Proc. Natl. Acad. Sci USA*, 1990, 87, 1620–1627.

Beppu et al., "A Simple method for the Assessment of Macrophage Scavenger Recptor–Ligan Interaction: Adherence of Erythrocytes Coated with Oxidized Low–Density Lipoprotein and Modified Albumin to Macrophages", *Biol. Pharmaceut. Bull.*, 1994, 17, 39–46.

Behl et al., "Hydrogen Peroxide Mediates Amyloid β Protein Toxicity", *Cell*, 1994, 77, 817–827.

Bolsi D., "Placche Senili e microglia", *Riv di Pat Nerv ment*, 1927, 32, 65–82.

Breitner et al., "Inverse association of anti–inflammatory treatments and Alzhemier's disease", *Neurology*, 1990, 44, 227–232.

Brunden et al., "pH–Dependent Binding of Synthetic β–Amyloid Peptides to glycosaminoglycans", *Neurochem.*, 61, 1993, 2147–2154.

Bu'ee et al., "Binding of secreted human neuroblastoma proteoglycans to the Alzheimer's amyloid A4 peptide", *Brain Res.*, 1993, 601, 154–163.

Chang, "Studies on insect neurotoxinetyramine as the neurotoxin released in hemolymph of DDT–prostrated cockroaches", *Kunchong Xuebao*, 27(1), 15–22 (Abstract Only: 101:67757z).

Christie et al., "Expression of the Macrophage Scavenger Receptor, a Multifunctional Lipoprotein Receptor, in Microglia Associated with Senile Plaques in Alzheimer's Disease", *Am. J. Pathol.*, 1996, 148, 399–403.

Cotman et al., "β–Amyloid Neurotoxicity: A Discussion of In Vitro Findings", *Neurobio. Aging*, 1992, 13, 587–590.

Davies P., "Neuronal abnormalities, not amyloid are the cause of dementia in Alzheimer disease", *Alzheimer Disease*, Terry, Katzman, and Bick (Eds.), New York, Raven Press, 1994, 327–333.

Davis et al., "The Amyloid Beta–Protein of Alzheimer's Disease is Chemotactic for Mononuclear Phagocytes", *Biochem. Biophys. Research Comm.*, 1992, 189(2), 1096–1100.

Davis, T.L., "Anti–Thy–1 immunotoxin, OX7–saporin, destroys cerebellar Purkinje cells after intraventricular injection in rats" *Brain Res.*, 1989, 504, 216–222.

Denis, M., "Human monocytes/macrophages: No or no No?", *J. Leukoc Biol.*, 1994, 55, 682–684.

Eikelenboom et al., "Inflammatory mechanisms in Alzheimer's disease", *TIPS*, 1994, 15, 447–450.

Faraj et al., "Tyramine Neurotoxicity and First–Pass Brain Technetium–99m– Diethylenetriamine Penta–Acetic Acid", *J. Pharm. Exp. Ther.*, 1987, 241, 42–47.

Flood et al., "Amnestic effects in mice of four synthetic peptides homologous to amyloid β protein from patients with Alzheimer disease", *Proc. Natl. Acad. Sci. USA*, 1991, 88, 3363–3366.

Fraser et al., "$\alpha_1$–Antichymotrypsin Binding to Alzheimer Aβ Peptides Is Sequence Specific and Induces Fibril Disaggregation In Vitro", *J. Neurochem.*, 1993, 61, 298–305.

Fraser et al., "Conformation and Fibrillogenesis of Alzheimer Aβ Peptides with Selected Substitution of Charged Residues", *J. Molecular Biol.*, 1994, 244, 64–73.

Fraser et al., "Fibril Formation by Primate, Rodent, and Dutch–Hemorrhagic Analogues of Alzheimer Amyloid β–Protein", *Biochem.*, 1992, 31, 10716–10723.

Games et al., "Lack of Alzheimer Pathology After β–Amyloid Proten Injections in Rat Brain", *Neurobiol. Aging*, 1992, 13, 569–576.

Gennaro A., Remington's Pharmaceutical Sciences 18th Ed., 1990, Mack Publishing Co.

Giaccone et al., "Down patients: extracellular preamyloid deposits precede neuritic degeneration and senile plaques", *Neurosci. Lett.*, 1989, 97, 232–238.

Giulian D., "Microglia and Diseases of the Nervous System", *Current Neurology*, Appel, S.H (ed.), St. Louis: Mosby–Year Book, Inc., 1992, 12, 23–54.

Graham, "Catecholamine Toxicity: A Proposal for the Molecular Pathogenesis of Manganese Neurotoxicity and Parkinson's Disease", *NeuroToxicology*, 1984, 5(1), 83–95.

Giulian, "Specific domains of beta–amyloid from Alzheimer plaque elicit neuron killing in human microglia", *J. Neurosci.*, 1996, 16(19), 6021–6037 (Abstract only).

Giulian et al., "Characterization of Ameboid Microglia Isolated from Developing Mammalian Brain", *J. Nurosci.*, 1986, 6, 2163–2178.

Giulian et al., "Inhibition of Monocuclear Phagocytes Reduces Ischemic Injury in the Spinal Cord", *Ann. Neurol.*, 1990, 27, 33–42.

Giulian et al., "The Role of Mononuclear Phagocytes in Wound Healing After Traumatic Injury to Adult Mammalian Brain", *J. Neurosci.*, 1989, 9, 4416–4429.

Giulian et al., "Brain Glia Release Factors with Opposing Actions upon Neuronal Survival", *J. Neurosci.*, 1993, 13, 29–37.

Giulian et al., "Reactive Mononuclear Phagocytes Release Neurotoxins After Ischemic and Traumatic Injury to the Central Nervous System", *J. Neurosci. Res.*, 1993, 36, 681–693.

Giulian et al., "The Impact of Microglia–Derived Cytokines upon Gliosis in the CNS", *Dev. Neurosci.*, 1994, 16, 128–136.

Giulian et al., "Rapid Communication", *Neurochem Int.*, 1995, 27, 119–137.

Giulian et al., "Cell Surface Morphology Identifies Microglia as a Distinct Class of Monoculear Phagocyte", *J. Neurosci.*, 1995, 15, 7712–7726.

Harris et al., "B–Amyloid peptide–derived, oxygen–dependent free radicals inhibit glutamate uptake in cultured astrocytes: implications for Alzheimer's disease", *NeuroReport*, 1995, 6, 1875–1879.

Hensley et al., "A model for β–amyloid aggregation and neurotoxicity based on free radical generation by the peptide: relevance to Alzheimer disease", *Proc. Natl. Acad. Sci. USA*, 1994, 91, 3270–3274.

Howlett et al., "Aggregation state and neurotoxic properties of Alzheimer beta–amyloid peptide", *Neurodegenertion*, 1995, 4, 23–32.

Hunter et al., "Amidination", *Meth. Enzymol.*, 1972, 25, 585–596.

Ignarro L., "Nitric Oxide", *Hypertension*, 1990, 16, 477–483.

Kallapur et al., "The Neural Cell Adhesion Molecule (NCAM) Heparin Binding Domain Binds to Cell Surface Heparan Sulfate Proteoglycans", *J. Neurosci Res.*, 1992, 35, 538–548.

Koh et al., "B–Amyloid protein increases the vulnerability of cultured cortical neurons to excitotoxic damage", *Brain Res.*, 1990, 533, 315–320.

Kohler et al., "Continuous cultures of fused cells secreting antibody of predefined specificity", *Nature*, 1975, 256, 495–497.

Koo et al., "Amyloid β–protein as a substrate interacts with extracellular matrix to promote neurite outgrowth", *Proc. Natl. Acad. Sci. USA*, 1993, 90, 4748–4752.

Kuo et al., "Water–soluble Aβ (N–40, N–42) Oligomers in Normal and Alzheimer Disease Brains", *J. Biol. Chem.*, 1996, 271, 4077–4081.

Lees, "The possible contribution of microglia and macrophages to delayed neuronal death after ischemia", *J. Neurol Sci.*, 1993, 114, 119–122.

London et al., "Neurocytopathic effects of β–amyloid––stimulated moncytes: A potential mechanism for central nervous system damage in Alzheimer disease", *Proc. Natl. Acad. Sci. USA*, 1996, 93, 4147–4152.

Lorenzo et al., "B–Amyloid neurotoxicity requires fibril formation and is inhibited by Congo red", *Proc. Natl. Acad. Sci. USA*, 1994, 91, 12243–12247.

Lucca et al., "Nonsteroidal Antiinflammatory Drug Use in Alzheimer's Disease", *Biol. Psychiat.*, 1994, 36, 854–856.

Masliah et al., "Diffuse Plaques Do Not Accentuate Synapse Loss in Alzheimer's Disease", *Am. J. Pathol.*, 1990, 137, 1293–1297.

Maslia et al., Re–evaluation of the structural organization of neuritic plaques in Alzheimer's disease, *J. Neurophatol Exp Neurol*, 1993, 52(6), 619–632.

Mattson et al., "B–Amyloid Precursor Protein and Alheimer's Disease: the Peptide Plot Thickens", *Neurobiol. Aging*, 1992, 13, 617–621.

Mattson et al., "B–Amyloid Peptides Destabilize Calcium Homeostasis and Render Human Cortical Neurons Vulnerable to Excitotoxicity" *J. Neurosci.*, 1992, 12, 376–389.

May et al., "B–Amyloid Peptide in Vitro Toxicity: Lot–to––Lot Variability", *Neurobiol. Aging*, 1992, 13, 605–607.

McGeer et al., "Reactive Microglia in patients with senile dementia of the alzheimer type are positive for the histocompatibility glycoprotein HLA–DR", *Neurosci. Lett.*, 1987, 79, 195–200.

McGeer et al., "Anti–Inflammatory drugs and Alzheimer disease", *Lancet*, 1990, 335, 1037.

Meda et al., "Activation of microglial cells by B–Amyloid protein and interferon–γ", *Nature*, 1995, 374, 647–650.

Miles E., "Modification of Histidyl Residues in Proteins by Diethylyrocarbonate", *Meth. Enzymol.*, 1977, 47, 431–442.

Mirra et al., "The Neuropathology Assessement of Alzheimer's Disease and Related Dementias: The CERAD Experience", Alzheimer's Disease: Advances in Clinical and Basic Research, Corain (ed.), John Wiley & Sons, Decature, GA, 1993, 207–211.

Mrak et al., "Glial Cytokines in Alzheimer's Disease: Review nad Pathogenic Impliations", *Hum. Pathol.*, 1995, 26, 816–823.

Narindrasorasak et al., "High Affinity Interactions between the Alzheimer's B–Amyloid Precursor Proteins and the Basement Membrane Form of Heparan Sulfate Proteoglycan", *J. Biol. Chem.*, 1991, 266, 12878–12883.

Patthy et al., "Reversible Modification of Arginine Residues", *J. Biol. Chem.*, 1975, 250, 557–564.

Perlmutter et al., "MHC class II–positive microglia in human brain: association with Alzheimer lesions", *J. Neurosci Res.*, 1992 33, 549–558.

Piani et al., "Murine brain macrphages induce NMDA receptor mediated neurotoxicity in vitro by secreting glutamate", *Neurosci. Lett.*, 1991, 133, 159–162.

Pike et al., "Aggregation–related toxicity of synthetic B–Amyloid protein in hippocampal cultures", *Eur. J. Pharmacol.*, 1991, 207, 367–368.

Pike et al., "Neurodegeneration induced by B–Amyloid Peptides in vitro: The role of Peptide Assembly State", *J. Neurosci.*, 1993, 13, 1676–1687.

Pike et al., "Amino–terminal Deletions Enhance Aggregation of B–Amyloid Peptides in vitro", *J. Biol Chem.*, 1995, 270, 2385–23898.

Podlinsny et al., "Synthetic Amyloid β–Protein Fails to Produce Specific Neurotoxicity in Monkey Cerebral Cortex", *Neurobiol. Aging*, 1992, 13, 561–567.

Pollack et al., "Sulfonated dyes attenuate the toxic effects of B–Amyloid in a structure–specific fashion", *Neurosci. Lett.*, 1995, 197, 211–214.

Price et al., "Toxicity of Synthetic Aβ Peptides and Modeling of Alzheimer's Disease", *Neurobiol. Aging*, 1992, 13, 623–625.

Rio–Hortega P., Cytology and Cellular Pathology of the Nervous System, Penfield (ed.) NY Hocker, Inc., 1932, 481–584.

Riordan et al., "Diazonium Salts as Specific Reagents and Probes of Protein Conformation", *Meth. Enzymol.*, 1972, 25, 521–531.

Rogers et al., "Expression of immune system–associated antigens by cells of the human central nervous system: relationship to the pathology of Alzheimer's disease", *Neurobiol. Aging*, 1988, 9, 339–349.

Rogers et al., "Complement activation by B–Amyloid in Alzheimer disease", *Proc. Natl. Acad. Sci. USA*, 1992, 89, 10016–10020.

Roher et al., "Isolation and Chemical Characterization of Alzheimer's Disease Paired Helical Filament Cytoskeletons: Differentiation from Amyloid Plaque Core Protein", *J. Cell Biol.*, 1988, 107, 2703–2716.

Roher et al., "Structural Alterations in the Peptide Backbone of β–Amyloid Core Protein May Account for its Depoisition and Stability in Alzheimer's Disease", *J. Biol. Chem.*, 1993, 268, 3072–3083.

Roher et al., "Morpholigical and Biochemical Analyses of Amyloid Plaque Core Proteins Purified from Alzheimer Disease Brain Tissue", *J. Neurochem.*, 1993, 61, 1916–1926.

Schnabel J., "New Alzheimer's Therapy Suggested", *Science*, 1993, 260, 1719–1720.

Schrode et al., "Transglutaminase–catalyzed Cross–linking through Diamines and Polyamines", *J. Biol. Chem.*, 1978, 253, 4837–4840.

Selkoe D.J., "The Molecular Pathology of Alzheimer's Disease", *Neuron.*, 1991, 6, 487–498.

Simmons et al., "Secondary Structure of Amyloid β Peptide Correlates with Neurotoxic Activity in Vitro", *Mol. Pharmacol.,* 1994, 45, 373–379.

Sommer et al., "Monoclonal Antibodies (01 to 04) to Oligodendrocyte Cell Surfaces: An Imunocytoological Study in the Central Nervous System", *Develop. Biol.,* 1981, 83, 311–327.

Stephenson et al., "In vivo effects of β–Amyloid implants in rodents: lack of potentiation of damage associated with transient global forebrain ischemia", *Brain Res.,* 1992, 586, 235–246.

Terry et al., "Structural Basis of the Cognitive Alterations in Alzheimer Disease", *Alzheimer's Desease,* NY, Raven Press, 1994, Ch. 11, 179–196.

Thery, "Cytotoxic Effect of Brain Macrophages on Developing Neurons", *Eur. J. Neurosci,* 1991, 3, 1155–1164.

Verga et al., "Alzheimer patients and Down patients: cerebral preamyloid deposits differ ultrastructurally and histochemically frm the amyloid of senile plaques", *Neurosci. Lett.,* 1989, 105, 294–299.

Whitson et al., "Amyloid β Protein Enchances the Survival of Hippocampla Neurons in Vitro", *Science,* 1989, 243, 1488–1490.

Wujek et al., "Deposits of Aβ Fibrils are Not Toxic to Cortical and Hippocampal Neurons in Vitro", *Neurobiol. Aging,* 1996, 17, 107–113.

Yamaguchi et al., "Diffuse Types of Senile plaques in the brains of Alzheimer–type dementia", *Acta Neurophatol.,* 1988, 77, 113–119.

Yankner et al., "Seminars in Medicine of the Beth Israel Hosipital", *New Eng. J. Med.,* 1991, 325, 1849–1857.

Yankner et al., "Neurotrophic and Neurotoxic Effects of Amyloid β Protein: Reversal by Tachykinin Neuropeptides", *Science,* 1990, 250, 279–282.

Younkin S., "Evidence that Aβ42 Is the Real Culprit in Alzheimer's Disease", *Ann. Neurol.,* 1995, 37, 287–288.

* cited by examiner

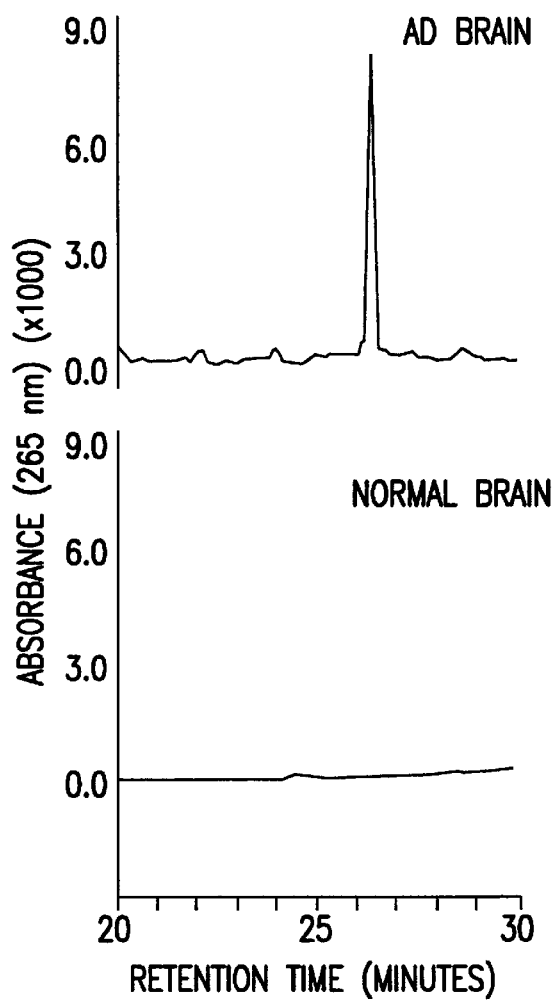
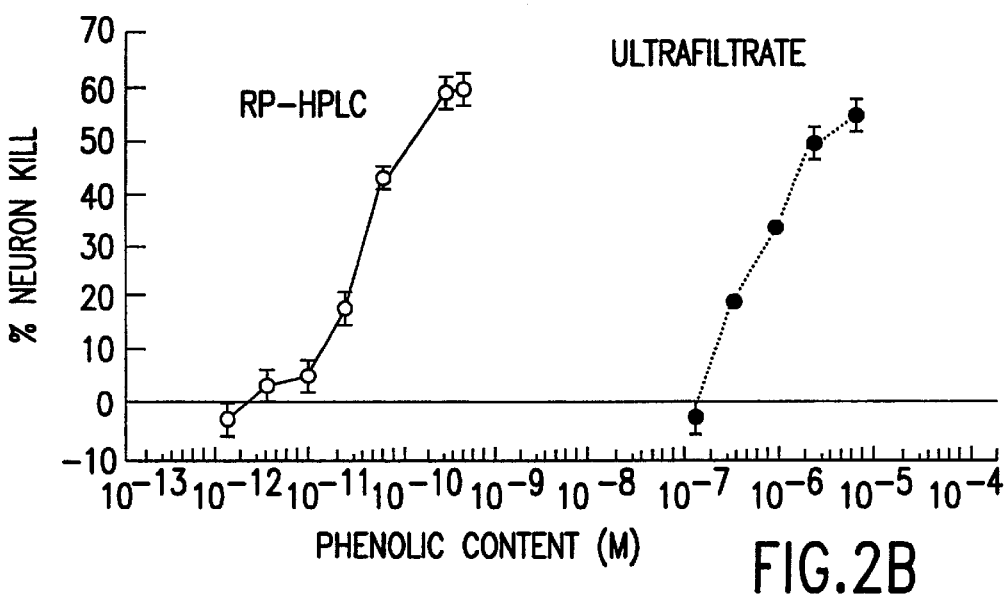
FIG.2A
FIG.2B

NTox

TYROSINE

TYRAMINE

DOPAMINE

FIG.17

EFFECTS OF Aβ PEPTIDES UPON MICROGLIA

| PEPTIDE | BLOCKED Aβ1-42 BEAD BINDING | BLOCKED Aβ1-42 TOXICITY | BLOCKED PLAQUE TOXICITY |
|---|---|---|---|
| β1-42 (HUMAN) | NA | NA | NA |
| β1-40 (HUMAN) | + | NA | NA |
| β1-40 (RODENT) | − | − | − |
| β36-42 | − | − | − |
| β17-43 | − | − | − |
| β25-35 | − | − | − |
| β1-28 | + | + | + |
| β10-20 | + | + | + |
| β1-16 | + | + | + |
| β1-16 (Gln₁₁) | − | − | − |
| β1-11 | − | − | − |
| β1-42 (Gln₁₃Gln₁₄) | + | NA | NA |
| β10-42 | + | + | + |
| β10-16 | + | + | + |
| β12-28 | − | − | − |
| β1-5 | | | |

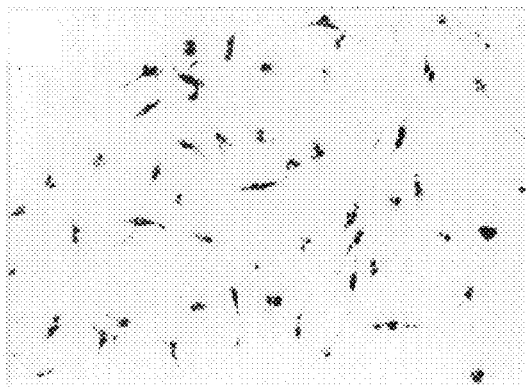
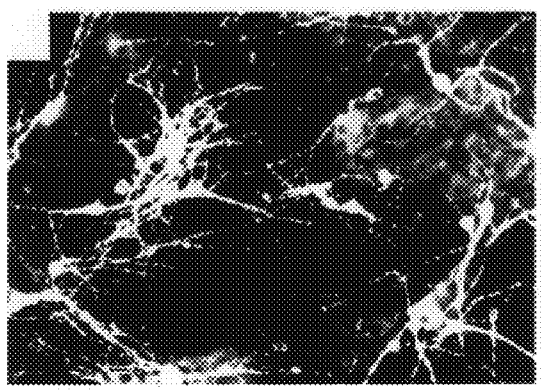
FIG.22A  FIG.22B
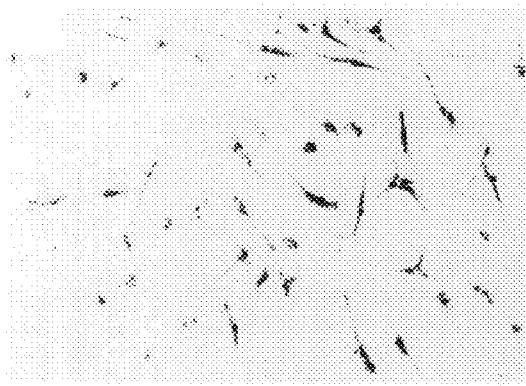
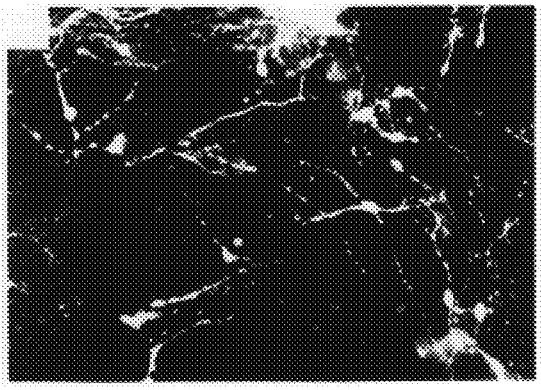
FIG.22C  FIG.22D
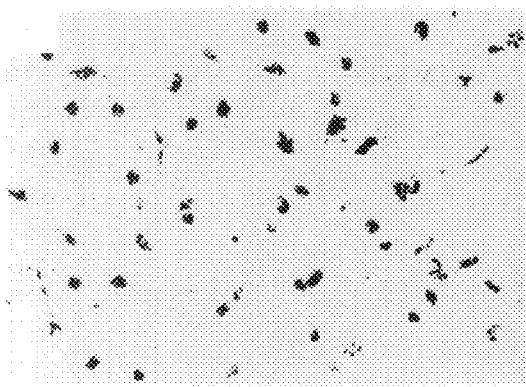
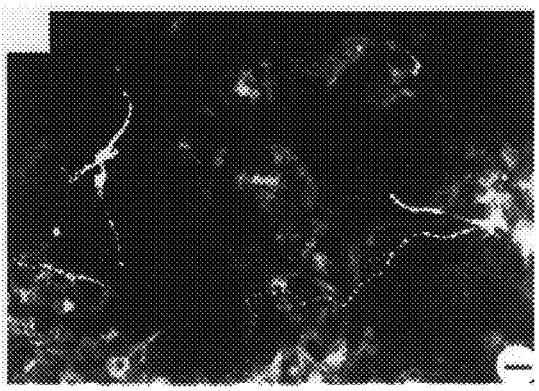
FIG.22E  FIG.22F

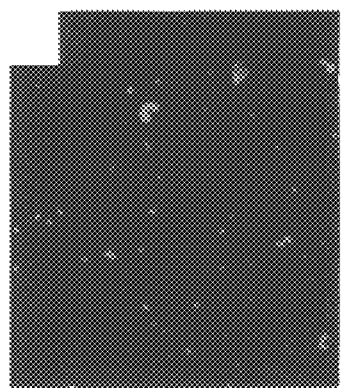 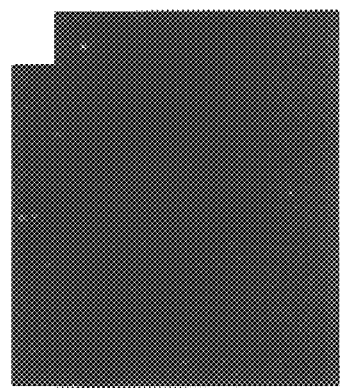
FIG.28A FIG.28B
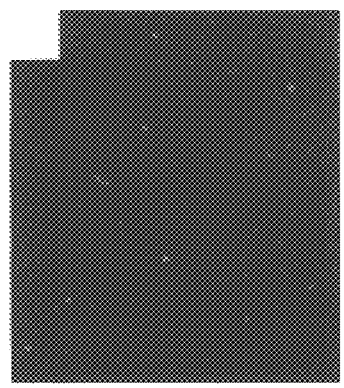 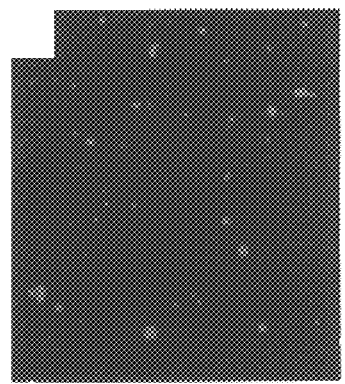
FIG.28C FIG.28D
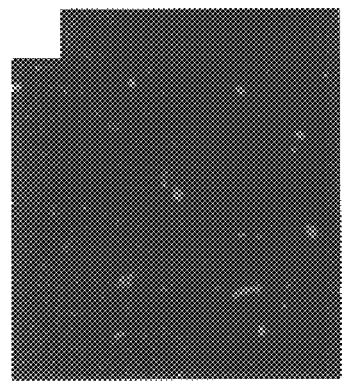 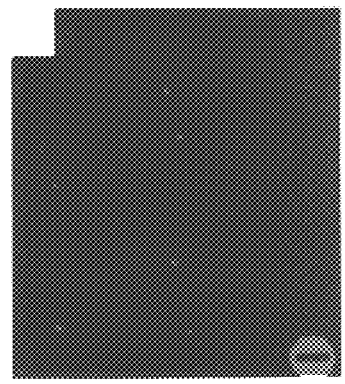
FIG.28E FIG.28F

FIG.29B

SEQUENCE LISTING (1) GENERAL INFORMATION:

(iii) NUMBER OF SEQUENCES: 2

```
(2) INFORMATION FOR SEQ ID NO: 1:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION:  SEQ ID NO: 1:

His His Gln Lys (2) INFORMATION FOR SEQ ID NO: 2:

(i) SEQUENCE CHARACTERISTICS:
        (A) LENGTH: 42 amino acids
        (B) TYPE: amino acid
        (D) TOPOLOGY: linear (ii) MOLECULE TYPE: peptide (xi) SEQUENCE DESCRIPTION:  SEQ ID NO: 2:

Asp Ala Glu Phe Arg His Asp Ser Gly Tyr Glu Val His His Gln Lys
5               10                  15

Leu Val Phe Phe Ala Glu Asp Val Gly Ser Asn Lys Gly Ala Ile Ile
20              25                  30

Gly Leu Met Val Gly Gly Val Val Ile Ala
35              40
```

IDENTIFICATION OF AGENTS THAT PROTECT AGAINST INFLAMMATORY INJURY TO NEURONS

This is a division, of application Ser. No. 08/717,551, filed Sep. 20, 1996, the disclosure of which is herein incorporated by reference.

REFERENCE TO GOVERNMENT GRANTS

This work has been supported in part by a grant from the National Institutes of Health, grant number NS25637. The United States Government may have certain rights in this invention.

BACKGROUND OF THE INVENTION

Mononuclear phagocytes are closely associated with diseases of the central nervous system. Microglia found in normal adult brain are highly ramified, quiescent cells that retract processes and become reactive during CNS injury (Rio-Hortega, 1932). Reactive microglia (activated brain mononuclear phagocytes) have been identified with Alzheimer Disease (AD) neuritic plaques (Bolsi, 1927; McGeer et al., 1987; Rogers et al., 1988; Giulian, 1992; Perlmutter et al., 1992; Giulian et al., 1995a). As a result, β amyloid (Aβ)-induced neuron damage is thought to involve inflammatory cells. In Alzheimer Disease, quantitative histopathology has determined that >80% of core plaques are associated with clusters of reactive microglia while fewer than 2% of diffuse Aβ deposits show such an association (Giulian et al., 1995a). These observations suggest that brain inflammatory responses may be directed specifically against the constituents of neuritic and core plaques. As the principal immune effector cells of the brain, activated microglia are capable of releasing such cytotoxic agents as proteolytic enzymes, cytokines, complement proteins, reactive oxygen intermediates, NMDA-like toxins, and nitric oxide (Thery et al., 1991; Giulian, 1992; Rogers et al., 1992; Lees, 1993; Banati, R. B., 1993).

Alzheimer Disease accounts for more than 15 million cases worldwide and is the most frequent cause of dementia in the elderly (Terry, R. D., Katzman, Bick, K. L. (eds), 1994) and is thought to involve mechanisms which destroy neurons and synaptic connections. The neuropathology of this disorder includes formation of senile plaques which contain aggregates of Aβ1–42 (Selkoe, D. J., 1991, Yankner and Mesulam, 1991; Price et al., 1992; Younkin, 1995). Senile plaques found within the gray matter of AD patients are in contact with reactive microglia and are associated with neuron damage (Terry, R. D., 1994 a and b, Masliah, E., et al., 1994, and Perlmutter, et al., 1992). Plaque components from microglial interactions with Aβ plaques tested in vitro were found to stimulate microglia to release a potent neurotoxic amine, thus linking reactive microgliosis with AD neuronal pathology (Giulian, et al., 1995). However, the plaque component, or components, which elicits neurotoxic responses in microglia remained elusive.

A second tyye of Aβ accumulation found in both AD and aged normal brain consists of diffuse plaques (discrete mesh-like structures of 70 to 100 μm diameter, visualized by silver staining, thioflavine S, or immunohistochemistry) which are not associated with such pathological changes as dystrophic neurites or decline in cognitive function (Yamaguchi et al., 1988; Masliah et al., 1990, 1993). Finally, diffuse, amorphous deposits of Aβ, demonstrable only by immunohistochemistry, have been described in aged brain and as an early manifestation of AD-like pathology in Down's syndrome (Giaccone et al., 1989; Verga et al., 1989). Although the mechanisms which link neuritic and core plaques to dementia remain unresolved, two principal hypotheses have been advanced: 1) that AD acts as a potent and direct neurotoxic agent (Yankner et al., 1990) or 2) that neuritic/core plaques elicit a cascade of cellular events which lead to neuronal pathology (Davies, 1994; Giulian et al., 1995a). Support for the first hypothesis comes from in vitro observations in which synthetic Aβ peptides appear toxic to enriched cultures of neurons (Pike et al., 1991; Cotman et al., 1992) or to various non-neuronal cell lines (Behl et al.,1994; Pollack et al., 1995). Support for the second hypothesis comes from evidence that neuritic/core plaques are not directly neurotoxic, as shown by the fact that neurons can be grown successfully atop Aβ peptides (Koo et al., 1993; Wujek et al., 1996), that neuritic/core plaques added directly to neurons do not cause neuron damage (Giulian et al., 1995a), and that Aβ peptides infused into the brain do not cause tissue injury (Games et al. 1992; Podlisny et al., 1992; Stephenson and Clemens., 1992).

Since the description by Bolsi (1927) of reactive microglia near plaques in AD brain, it has been uncertain whether these reactive non-neuronal cells actually contribute to the disease process or merely reflect ongoing pathology. Recently, however, it has become clear that reactive microglia surround only certain types of amyloid deposits in the brain (the neuritic and core plaques) while ignoring nearby deposits of other types, including diffuse plaques (Perlmutter et al., 1992; Giulian et al., 1995a). Such selectivity in the distribution of reactive glia suggest that specific signals within neuritic and core plaques drive brain inflammation. With the increasing recognition that reactive microglia can mediate neuronal injury through release of cytotoxic factors (Banati et al., 1993; Giulian et al., 1993a), speculation on the involvement of microglia in AD has encompassed the release of complement proteins (Rogers et al., 1988, 1992), cytokines (Meda et al., 1995; Mrak et al., 1995), NMDA-like toxins (Piani et al., 1991; Giulian et al., 1995a, b), and free radicals (Thery et al., 1991; Hensley et al., 1994.

The present invention demonstrates that Aβ1–42 is the plaque-derived component which elicits neurotoxic responses in microglia. Importantly, the N-terminus of human Aβ provides an anchoring site necessary for initiating this neurotoxic cascade. More particularly, the HHQK-containing sequence is found to be significant in initiation. Because HHQK-like agents suppress toxic microgliosis in AD brain, neuronal loss and dementia may thereby be slowed. The present invention provides strategies for blocking the activation of microglia, thus making possible screening for therapies for the treatment of inflammatory injury to neurons in conditions such as Alzheimer Disease, stroke, trauma, multiple sclerosis (MS), Parkinson's disease, HIV infection of the central nervous system, amyotrophic lateral sclerosis (ALS), hereditary hemorrhage with amyloidosis-Dutch type, cerebral amyloid angiopathy, cerebral amyloid angiopathy, Down's syndrome, spongiform encephalopathy, Creutzfeld-Jakob disease, and the like.

SUMMARY OF THE INVENTION

The present invention is directed to a method of screening for an agent that inhibits the effect of a neurotoxin from a plaque component activated mononuclear phagocyte on a neuron comprising comparing measured mononuclear phagocyte-plaque component complex formation in the presence of an agent suspected of inhibiting complex formation to a measured control, wherein reduction of mononuclear phagocyte-plaque component complex formation compared to said control results in detection of an agent that inhibits mononuclear phagocyte-plaque component complex formation, and isolating a mononuclear phagocyte from an inhibited mononuclear phagocyte-plaque component complex formation, comparing said plaque component activation of a mononuclear phagocyte from an inhibited complex in the presence of an agent suspected of inhibiting activation to a measured control, wherein reduction of plaque component activation of said mononuclear phagocyte compared to said control results in detection of an agent that inhibits plaque component activation of mononuclear phagocytes and isolating a mononuclear phagocyte which is plaque component activation inhibited, comparing plaque component induced neurotoxicity of an activation inhibited mononuclear phagocyte in the presence of an agent suspected of inhibiting neurotoxicity to a measured control, wherein reduction of plaque component induced neurotoxicity compared to a control results in detection of an agent that inhibits a plaque component induced neurotoxic mononuclear phagocyte and isolating a plaque component induced neurotoxic mononuclear phagocyte, and measuring neuron function of a neuron in the presence of a neurotoxin from a plaque component activated mononuclear phagocyte or from a plaque component induced neurotoxic mononuclear phagocyte and an agent suspected of inhibiting the effect, wherein an increase in neuron function compared to a control results in detection of an agent that inhibits the effect of a neurotoxin from a plaque component activated mononuclear phagocyte on a neuron.

The present invention is directed to a method of screening for an agent that inhibits mononuclear phagocyte-plaque component complex formation by comparing mononuclear phagocyte-plaque component complex formation in the presence of an agent suspected of inhibiting the complex formation with a control such that a decrease in complex formation as compared to the control results in the detection of an agent that is inhibitory to mononuclear phagocyte-plaque component complex formation.

In addition, a method of screening for an agent that inhibits mononuclear phagocyte activation by a plaque component is embodied by the present invention and comprises comparing mononuclear phagocyte activation by a plaque component in the presence of an agent suspected of inhibiting the activation to a control such that a decrease in activation as compared to the control results in the detection of an agent that is inhibitory to mononuclear phagocyte activation by a plaque component.

Another method of the present invention is directed to screening for an agent that inhibits neurotoxicity of a mononuclear phagocyte which neurotoxicity is induced by a plaque component comprising comparing such neurotoxicity of a mononuclear phagocyte in the presence of an agent suspected of inhibiting neurotoxicity with a control where a decrease in mononuclear phagocyte neurotoxicity compared to the control results in the detection of an agent that is inhibitory to mononuclear phagocyte neurotoxicity induced by a plaque component.

A method of screening for an agent that inhibits the effect of a neurotoxin on a neuron, which neurotoxin is from a plaque component-activated mononuclear phagocyte comprising comparing neuron function of a neuron in the presence of a neurotoxin from a plaque component-activated mononuclear phagocyte and an agent suspected of inhibiting such effect to a measured control such that an increase in neuron function compared to said control results in detection of an agent that inhibits the effect of a neurotoxin from a plaque component activated a mononuclear phagocyte on neurons is yet another method embodied by the present invention.

Methods of measuring mononuclear phagocyte-plaque component complex formation, mononuclear phagocyte activation by a plaque component, mononuclear phagocyte neurotoxicity induced by a plaque component and the effect of a neurotoxin from a plaque component activated mononuclear phagocyte on a neuron include labeling one of the above- identified elements followed by imaging and amplifying nucleic acids from the mononuclear phagocyte or neuron and observing the amplified nucleic acids. Further to the forgoing detection methods, plaque suppressors may be measured by observing altered mononuclear phagocyte morphology, observing the expression of cell surface molecules on mononuclear phagocytes, and observing the release of nitric oxide, free radicals, cytokines, lipoproteins, enzymes, and proteins from mononuclear phagocytes. Furthermore, inactivators of neurotoxic mononuclear phagocytes may be detected by observing a loss of metabolic function, release of intracellular material, penetration of impermeant dyes, and reduction of cell number of neurons. Yet additional methods of detecting neurotoxic blockers include observing disruption of normal cell metabolism such as metabolism of glucose, the production of ATP, maintenance of ion gradients across a cell membrane, protein synthesis, nucleic acid synthesis, and mitochondrial respiration.

An agent is also provided by the present invention which agent is obtained by the process of screening for an agent suspected of inhibiting mononuclear phagocyte-plaque component complex formation, neurotoxicity of mononuclear phagocytes, and effects of neurotoxins on neurons. Agents having the sequence HHQK (SEQ ID NO: 1), chloroquine, tyramine, or an agent having activity similar to these agents, are objects of the present invention. A pharmaceutical compositions comprising an agent are also provided for by the present invention.

BRIEF DESCRIPTION OF THE DRAWINGS

FIGS. 2A and B display steps in the isolation of NTox from frozen Alzheimer brain gray matter that involved extractions into ethyl acetate, acid hydrolysis and sequential gradient reverse phase high performance liquid chromatography (RP-HPLC). FIG. 2A shows the final step of purification by RP-HPLC, using a C18 column and an acetonitrile gradient, shows a peak with elution at about 14% acetonitrile. Importantly, this peak is found in Alzheimer but not in control brain and corresponds to activity which is highly toxic to ciliary neurons. FIG. 2B displays the degree of purification of neurotoxin from Alzheimer brain tissue. Dose response curves show that the $ED_{50}=10\ \mu M$ in the ultrafiltrate compared with 100 pM for highly purified toxin following acid hydrolysis and C18 RP-HPLC. From such preparations, estimations of >100,000 fold purification of toxin from human brain. The phenolic content is estimated by $UV_{max}$ at 265 nm with a similar result obtained when values are normalized to amine content measured by fluorescamine.

FIG. 6A) Photomicrograph of trypan blue(+) control HEK cells exposed to NTox. Few blue, dead cells are noted.

FIG. 8A reveals that at two weeks after implantation, there is a 5-fold increase in receptor mRNA surrounding the Sphere$_{A\beta1-42}$ when compared to undamaged control tissue or Sphere$_{BSA}$.

FIG. 14A shows a fluorescence photomicrograph of neurons immuno-stained with anti-neurofilament and anti-MAP 2 antibodies found in control hippocampal cultures (1,200 cells per $mm^2$) that were supplemented with microglia (500 per $mm^2$). FIG. 14B shows a culture identical to FIG. 13A exposed to synthetic human A$\beta$1–42 (1 $\mu$mole/l) for 72 hours resulting in a dramatic loss of neurons (Bar=20 microns). FIG. 14C shows testing of various A$\beta$ peptides in a neurotoxicity assay using rat hippocampal cultures supplemented with microglia resulting in 70–80% killing of neurons after exposure for 72 hours to human A$\beta$1–40, A$\beta$1–42, or A$\beta$1–42 coupled to microspheres (Spheres A$\beta$1–42) while elimination of microglia from the cultures prevented neuron death. The pattern of neuron killing by synthetic peptides was similar to that elicited by either isolated AD plaques or native A$\beta$ purified from plaques. Interestingly, rodent A$\beta$1–40 (Arg5, Phe10, and Arg13) did not activate microglia. The A$\beta$ peptides containing either the N-terminus of the peptide (A$\beta$1–11, A$\beta$1–16, and A$\beta$1–28) or C-terminus (A$\beta$17–43) alone also were inactive. FIG. 14D shows the capacity of A$\beta$1–42 (1 $\mu$mole/1) to activate microglia examined after modification of the N-terminal region by chemical or enzymatic methods. Altering residues in the 13 to 16 domain blocked the A$\beta$1–42 induction of neurotoxic microglia. Cyclohexanedione (CHD)—modification of Arg5; tetranitromethane (TNM)—modification of Tyr10; diethylpyrocarbonate (DEPC)—modification of His6, His13, His14 with hydroxylamine used to reverse the DEPC effect; transglutaminase (TNG) modification of Gln15; ethyl acetimidate (EAM)—modification of Lys16.

FIG. 15A shows Aβ1–42 coupled to fluorescent microspheres and the Spheres Aβ1–42 monitored for binding to microglia after 4 hours at 37° C. in the presence of peptides (all at 10 μmoles/1). Only peptides containing residues 13–16 were able to competitively block sphere binding. FIG. 15B shows that enzymatic treatments of microglia altered Aβ binding to cells. Spheres$_{mal-BSA}$ (which bind to scavenger receptors) or Spheres$_{Aβ1-42}$ were incubated with microglia for 4 hours following pre-treatment of cells with trypsin (5000 units/ml at 37° C. for 60 min followed by inactivation with soybean trypsin inhibitor), with heparinase (heparin lyase EC 4.2.2.7; two consecutive treatments each of 0.01 units/ml for 60 min), or with chondroitinase ABC (chondroitin ABC lyase EC 4.3.3.4; two consecutive treatments each of 0.02 units/ml for 60 min). Binding by either Spheres$_{Aβ1-42}$ or Spheres$_{mal-BSA}$ to microglia were reduced by trypsin. Heparinase, however, only decreased Spheres$_{Aβ1-42}$ while chondroitinase affected neither Aβ or scavenger ligand binding sites. FIG. 15C shows that competition with ligands again suggest the involvement of a heparin sulfate-containing site on microglia with reduction of binding in the presence of heparin sulfate (50 μ/ml) or Aβ1–16 (10 μmole/1). In contrast, scavenger receptor binding of Spheres$_{mal-BSA}$ was blocked by known scavenger receptor ligands such as dextran sulfate (500 μg/ml) or acetylated LDL (ac-LDL, 200 μg/ml). FIG. 15D shows that plaque induction of neurotoxicity in microglia involves heparin sulfate-containing site. Microglia mixed with hippocampal neurons were treated with combinations of β-D-xyloside (1 mm), heparinase (0.02 units/ml), or chondroitinase (0.04 units/ml) and then exposed to plaques. Enzyme treatments alone, particularly that of heparinase brought on some reduction in neurotoxic activity; however, a combination of both enzymatic degradation of heparin sulfate plus competitive blockade of glycosylation by β-D-xyloside completely eliminated plaque activation.

FIG. 16A shows both Aβ1–42 (1 μmoles/1) in solution and or Spheres$_{Aβ1-42}$ (250,000 per well) added to hippocampal cultures supplemented with microglia in the presence of various synthetic Aβ peptides (all at 10 μmoles/1). Peptides containing residues 13 to 16 prevented Aβ induction of neurotoxic microglia FIG. 16B shows that dose curves show a greater blocking capacity for those peptides containing residues within the 1–16 hydrophilic portion of Aβ. Addition of more hydrophobic segments (beyond residue 16) diminish the ability of peptide to block Aβ1–42 interactions with microglia. FIG. 16C sets forth comparisons of various peptides confirm that the HHQK domain of Aβ blocks plaque activation of neurotoxic microglia.

FIG. 17 sets forth a table of the effects of β-Amyloid peptides upon microglia. All peptides which contain the unmodified region encompassing residues 13–16 (shaded) block Aβ1–42 to bind to Spheres$_{Aβ1-42}$, the ability of Aβ1–42 to induce microglial neurotoxicity, and the ability of AD plaques to induce microglial neurotoxicity. NA=not applied in this neurotoxicity test, since the free peptide induces microglial toxicity.

FIG. 18G shows counts of specific cell populations with and without Sap-ac-LDL treatment confirm the specific depletion of microglia. Data are expressed as mean values +/− standard error obtained from 9 randomly selected fields from at least 5 independent cultures viewed at 200× magnification.

FIG. 19A shows neuritic/core or diffuse plaques were isolated from cortical gray matter, solubilized in formic acid, and dialyzed against a betaine buffer. Equal amounts of plaque protein (normalized to total amine content at 400 μmoles/1) were added to neuronal cultures in the presence (100,000 cells per culture) or absence of rat microglia As shown, solubilized neuritic/core plaque proteins (Neuritic/Core Plaque) lead to significant killing of neurons, but only in the presence of microglia. Neither solubilized diffuse plaque proteins (Diffuse Plaque) nor the betaine buffer (Buffer Control) elicited neurotoxic activity. FIG. 19B shows size-exclusion chromatography of neuritic/core plaque proteins using two Superose 12 columns in tandem (300 mm×10 mm×2; beads 10 μm diameter). The chromatogram was developed with 80% glass distilled formic acid at a flow rate of 0.3 ml per minute and monitored at 280 nm. The approximate molecular masses of the fractions were: S1, 200 kDa; S2, 45 kDa; S3, 15 kDa; S4, 10 kDa; and S5, 5 kDa. FIG. 19C shows a histogram in which exposure to peaks S3, S4, and S5 all elicited significant increases in the percent of reactive microglia as defined by morphologic criteria, whereas peaks S1 and S2 do not. FIG. 19D shows fractions of solubilized neuritic/core plaques applied to hippocampal cultures in the presence or absence of microglia. No neuron killing was detected in cultures free of microglia. Neuron loss appeared, however, in microglia containing cultures exposed to peaks S3, S4, and S5, all which contain Aβ.

FIGS. 21A and 21B shows high concentrations of most Aβ peptides placed in hippocampal cultures containing neurons and astroglia (but depleted of microglia) show little effect. There is, however, a generalized cytotoxic action by Aβ25–35 at >30 μmoles/l on both neurons (FIG. 21A) and astroglia (FIG. 21B). In the absence of microglia, none of the Aβ peptides (at 1 μmole/1) produce destruction of neurons. When rat microglia are added to neuronal cultures, however, only Aβ1–40 and Aβ1–42 elicit neuron killing (FIG. 21C). As shown in FIG. 21D, addition of increasing numbers of microglia show a saturated neuron killing response at a density of 150 microglia per mm$^2$ when incubated with 1 μmole/liter Aβ1–42; microglia found within the E18 culture at the time of plating (endogenous microglia) also showed an efficient killing capacity in the presence of Aβ. These observations point to the need to deplete neuron cultures of microglia when assessing mechanisms of Aβ toxicity. Dose response curves reveal Aβ1–42 to be the most potent microglial stimulus with an estimated $ED_{50}$ of 10 nmoles/1 compared to 80 nmoles/1 for Aβ1–40 (500 microglia per $mm^2$; FIG. 21E).

FIG. 22A–F depicts cellular responses upon exposure to synthetic Aβ peptides. Phase microscopy shows that cultured rat microglia undergo morphological changes with retraction of processes when exposed to 1 μmole/1 Aβ1–42 (FIG. 22E); in contrast, 1 μmole/1 Aβ17–43 (FIG. 22C) does not alter microglial morphology which appear identical to untreated cells grown under control conditions (FIG. 22A). Fluorescence microscopy of neuron plus microglia cultures showed robust NF(+) MAP2(+) hippocampal neurons (FIG. 22B) that are undamaged after addition of conditioned media (10% vol/vol) from microglia incubated with 1 μmole/1 Aβ17–43 (FIG. 22D). Significant neuron loss occurred, however, if hippocampal cultures were exposed to conditioned media from microglia incubated with 1 μmole/1 Aβ1–42 (FIG. 22F). Bar=25 microns.

FIG. 23E) Comparison of capacity of Aβ in solution or coupled to microspheres (bead-bound) to elicit neurotoxic microglia (250,000 microspheres per culture; 100,000 microglia per culture; 72 hour incubation). Neuronal loss was similar if Aβ peptides were in solution or bound to beads, indicating that fibril formation, or other changes in tertiary structure, were not necessary to stimulate neurotoxic microglia.

FIG. 24A shows control cultures show complex networks of NF(+), MAβ-2(+) neurons. FIG. 24B shows exposure of cultures to 100 μmoles/liter Aβ1–42 in the absence of microglia has no effect on neuron number, while (FIG. 24C) addition of 100 nmoles/liter Aβ1–42 in the presence of rat microglia (500 cells per mm2) destroyed nearly all neurons. FIGS. 24D–G shows immunostaining for neuron-specific enolase (NSE) is not specific to neurons in CNS cultures as shown by immunofluorescent visualization of glia in cultures of neuron-free optic nerve, including galactocerebroside(+) oligodenroglia (FIG. 24D) and GFAβ(+) astrocytes (FIG. 24F) which are both NSE(+) (FIGS. 24E and 24G, respectively). Bar=10 μm. In FIG. 24H, ciliary neuron cultures showed that Aβ1–42 is not toxic to neurons in the absence of brain glia (Aβ1–42 only) after 48 hour exposure. Conditioned media from Aβ1–42-stimulated microglia (Microglia +Aβ1–42) did, however, kill neurons, indicating that astrocytes are not necessary to the microglial neurotoxicity.

FIG. 25A shows only Aβ-containing fractions from solubilized neuritic/core plaques [peaks S3 (54 nmole/1), S4 (220 nmole/1), and S5 (250 nmole/1)] elicit human microglia to engage in neurotoxic behaviors. FIG. 25B shows that when tested at 1 μmole/liter concentrations, synthetic Aβ1–40 and Aβ1–42 also stimulated release of neurotoxin from human microglia, while smaller AP fragments had no effect. Despite neuron killing, there is no evidence of increased production of nitrate or nitrite by human cells stimulated with either native (FIG. 25C) or synthetic (FIG. 25D) AD. FIG. 25E shows that neuron killing could be induced by human or rat microglia exposed to 1 μmole/liter of the human forms of either Aβ1–42 or Aβ1–40. The rodent form of Aβ1–40, however, was inactive, as were fragments of human Aβ, including 1–28, 12–28, and 17–43.

FIG. 26A shows agents that act as free radical scavengers (vitamin E, 100 μM; catalase, 25 units/ml; glutathione, 100 μM) did not block microglial killing of neurons. No protective effects were observed with the nitric oxide synthetase inhibitors L-N-5-(1-iminoethyl)ornithine hydrochloride (L-NIO, 10 μM) or diphenyl iodonium (DPI, 300 nM), although the NMDA antagonist AP5 prevented neuron death. FIG. 26B shows other NMDA antagonists acting at the receptor site (AP7), at the polyamine regulatory site (ifenprodil), or at the ion channel (MK801) all blocked neuron death, while the non-NMDA glutamate antagonists (GAMS, BNQX) did not. All drugs were applied at 1 μM. FIG. 26C shows isolation of neurotoxin from culture media conditioned by Aβ-stimulated rat microglia (Aβ1–42/Microglia) or from frozen AD gray matter (AD Brain) involved extractions in ethyl acetate (pH 10.5), acid hydrolysis, and sequential gradient RP-HPLC (C18 column using a 0 to 20% acetonitrile gradient in $dH_{20}$ with 0.1% trifluoroacetic acid). Neurotoxin activities from microglial conditioned media co-purifies with that from AD brain tissue with a co-elution using RP-HPLC at about 14% acetonitrile. Neurotoxicity was not found within control brain extracts or from unstimulated microglial culture media.

FIG. 10A shows a phase photomicrograph of rat microglial cell adhering to Sepharose bead coupled to human Aβ1–42 peptides. FIG. 27B shows a fluorescence photomicrograph of the same bead showing adherent cell labeled by the fluorescent microglial marker DiI-ac-LDL; Bar=20 microns. FIG. 27C shows rat microglial adherence to Sepharose-coupled beads after six hours. Plaque proteins derived from neuritic/core plaques provided an anchoring site for microglia, as did Aβ1–42. Importantly, Aβ1–28 also promoted bead binding, while Aβ17–43 did not. Controls included beads coupled to glycine (Control glycine) and to bovine serum albumin (Control-BSA). Data shown are expressed as the numbers of adhering cells per 100 randomly selected beads +/- standard error after 6 hour incubation at 37 ° C.

FIGS. 28A–G displays that the Aβ cell binding domain is required for activation of neurotoxic microglia. Fluorescent photomicrographs showing microsphere binding to enriched cultures of rat microglia (500/$mm^2$) after 4 hour incubation at 37 C. Coupling of Aβ peptides to fluorescent microspheres showed that Aβ1–42 (FIG. 28A), Aβ12–28 (FIG. 28D), and Aβ10–16 (FIG. 28E) readily bind, while peptides Aβ17–43 (FIG. 28B), Aβ1–11 (FIG. 28C), and Aβ1–5 (FIG. 28F) did not. Quantitations of binding pattern (FIG. 28G) indicated that regions of the N-terminus-containing amino acid residues 10–16 were necessary for Aβ binding to microglia. Data are expressed as mean values +/- standard error when viewed at 200× magnification.

FIGS. 29A–29B displays the comparison of Aβ effects upon microglia. FIG. 29A shows dose response curves in which although Aβ10–16 is able to bind to microglia, it did not elicit neurotoxic microglia. The addition of this microglial binding domain to Aβ17–42 (which neither binds to microglia nor elicits toxicity) created a peptide, Aβ10–42, which both bound to microglia and stimulated microglia to kill neurons. FIG. 29B shows a diagram comparing the structures and functions of synthetic peptides. The shaded area illustrates the N-terminal portion of Aβ that differs between human and rat forms and which appears necessary for microglial adherence.

DETAILED DESCRIPTION OF THE INVENTION

Figure 1:
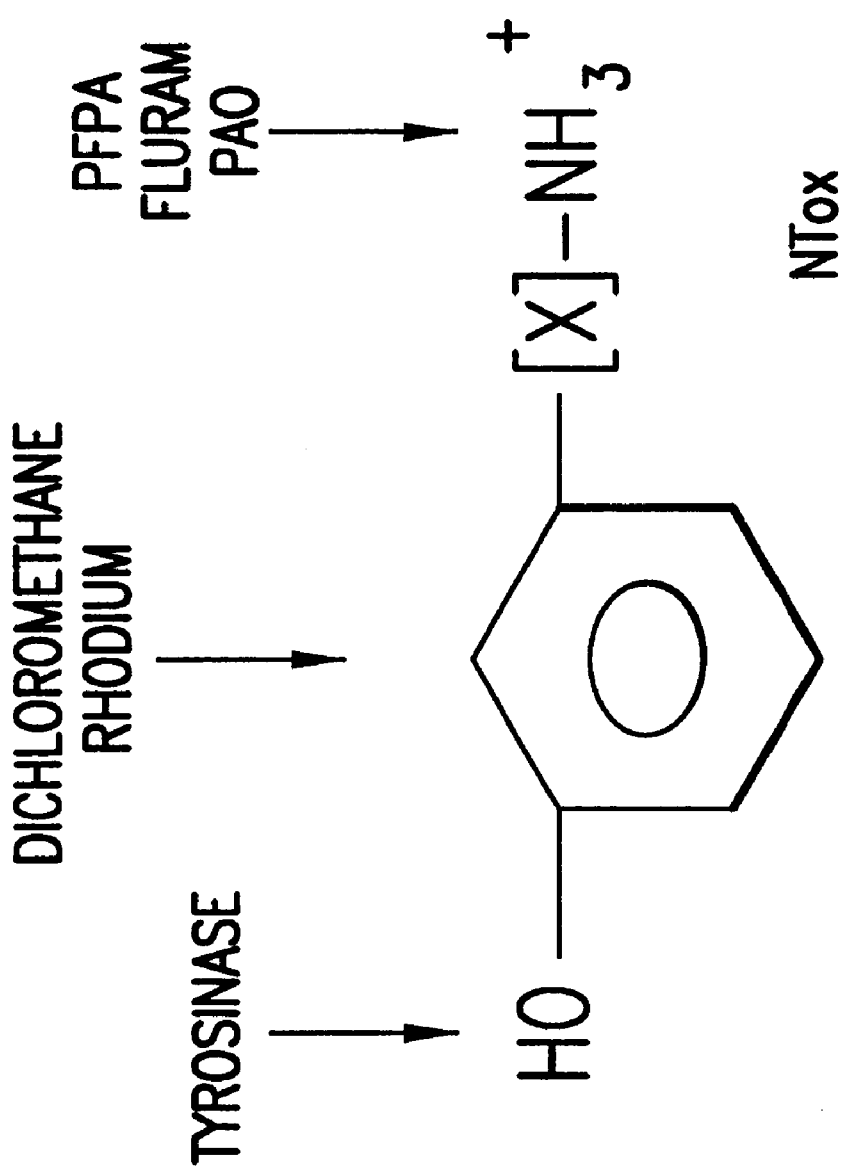
FIG. 1 displays the chemical structure of NTox, a neurotoxin released by microglia and macrophages after exposure to senile plaques in vitro or in vivo. Chemical and enzymatic modifications of the isolated toxin have identified within NTox a phenolic hydroxyl group sensitive to tyrosinase, a ring structure sensitive to reduction by rhodium, and a terminal amine sensitive to fluorescamine (fluram) or plasma amine oxidase (PAO).

Plaque component associated diseases are the result of a cascade of events that occur in the central nervous system. The cascade comprises four events including suppression of mononuclear phagocyte-plaque component complex formation, mononuclear phagocyte activation by a plaque component, mononuclear phagocyte neurotoxicity induced by a plaque component, and the effect of neurotoxins on neurons, which neurotoxins are released from mononuclear phagocytes.

An agent suspected of inhibiting mononuclear phagocyte-plaque component complex formation is referred to herein as a plaque suppressor. Mononuclear phagocyte inactivators are agents suspected of inhibiting mononuclear phagocytes activation by a plaque component in accordance with the present invention. Neurotoxicity of a mononuclear phagocyte by plaque component may be inhibited by an agent referred to herein as a neurotoxic mononuclear phagocyte inactivator. A neurotoxin blocker inhibits the effect of a plaque component activated mononuclear phagocyte or the effect of a plaque component induced neurotoxic mononuclear phagocyte. Plaque is composed of plaque components comprising peptide, protein, and non-protein constituents, including β-amyloid and fragments thereof including and not limited to Aβ1–39, Aβ1–40, Aβ1–42, α-antichymotrypsin, apolipoproteins including and not limited to apolipoproteins A and E, glycoproteins, proteoglycans including and not limited to heparan sulfate, and proteases, found in a mammalian central nervous system as a result of a disease. The sequences of β-amyloid referred to in the present invention are disclosed by Selkoe, 1991.

The present invention reveals that plaque components interact with mononuclear phagocytes to form a mononuclear phagocyte-plaque component complex. For purposes of the present invention, interact, and variations thereof, is used synonymously with associate, combine, attach, interfere, bond, and bind. The phrase "interact" or variations thereof, as used herein in connection with the action of a plaque component includes a covalent bond and an ionic bond or other means of chemical or electrochemical linkage or interaction. While not intending to be bound by any particular theory of operation, it is believed that the interaction involves cell surface compounds of the mononuclear phagocyte, such as and not limited to cell surface receptors for the plaque components identified herein.

Cells of the central nervous system are the cells inhibited by the agent of the present invention. A cell may be a central nervous system cell, such as and not limited to a mononuclear phagocyte and a neuron. Mononuclear phagocyte, as defined in accordance with the present invention, is a target cell of a plaque component and contains specific binding sites required for activation and induction of neurotoxicity. These binding sites include cell surface proteins that contain heparan sulfate. Mononuclear phagocyte is an immune cell, having a single nucleus and the ability to engulf particles, also known as phagocytosis. These cells are found in blood and body tissues including the central nervous system, including the brain, and includes a microglial cell, monocyte, macrophage, precursor cells of microglia, monocytes, and macrophages, microglia-like cell lines, macrophage-like cell lines, or cell lines modified to express microglia-like surface molecules that are active in accordance with the above definition of mononuclear phagocyte. A neuron as defined in accordance with the present invention includes a neuron-like cell line, a cell modified to express a N-methyl-D-aspartate receptor which neuron exhibits neuronal activity under typical normal, non-diseased state, conditions.

Plaque component-mononuclear phagocyte complex formation initiates a process that causes release of neurotoxic agents. Since the formation of Aβ complexes with mononuclear phagocytes induces mononuclear phagocytes to become neurotoxic, blockade of that Aβ-microglia complex formation suppresses neurotoxic mononuclear phagocytes.

Compounds with the ability to block such complex formations have structural features common either to a binding domain of Aβ or to the mononuclear phagocyte binding sites (such as Aβ ligand binding domain and/or sites containing heparan sulfate), for example.

Mononuclear phagocytes may be activated by a plaque component following complex formation. Activation is also referred to herein as immune activation, markers of which are any process that renders a mononuclear phagocyte more dynamic characterized by activities such as and not limited to increased movement, phagocytosis, alterations in morphology, and the biosynthesis, expression, production, or secretion of molecules, such as protein, associated with membranes including complement, scavengers, Aβ, and blood cell antigens, histocompatibility antigens for example. Production of molecules includes enzymes involved in the biosynthesis of bioactive agents such as nitric oxide synthetase, superoxide dismutase, small molecules such as eicosanoids, cytokines, free radicals and nitric oxide. Resease of factors includes proteases, apolipoproteins such as apolipoprotein E, and cytokines such as interleukin-1, tumor necrosis factor as well as other molecules such as NTox and hydrogen peroxide.

Mononuclear phagocyte-plaque component complex formation and mononuclear phagocyte activation induced by a plaque component may be followed by neurotoxicity of a mononuclear phagocyte induced by a plaque component. Neurotoxicity refers to a process that leads to the injury, destruction, or killing of neurons as measured by loss of metabolic function, release of intracellular material, penetration of impermeant dyes, reduction of cell number measured by biochemical or histological methods. For example, changes in biochemical markers such as loss of neurofilament or synaptophysin or release of lactate dehydrogenase, or other evidence of cell injury such as penetration of impermeant dyes including fluoresecent nuclear dyes and trypan blue. These and other strategies for identifying cell injury are known by those familiar in the art and are contemplated by the present invention.

The effect of a neurotoxin from a plaque component activated mononuclear phagocyte or from a plaque component induced neurotoxic mononuclear phagocyte on a neuron may take place following complex formation, activation and neurotoxicity. Neurotoxins are defined herein as substances that injure, damage, kill, or destroy a neuron while sparing other central nervous system cells such as glia, for example. Neurotosin blockers are agents which inhibit the effect of a neurotoxin released from plaque component activated mononulcear phagocytes. Neurotoxic compounds include phenolic amines such as Ntox (FIG. 1), form a complex with molecules of molecules of neurons in such a way as to disrupt neuron function and survival. The possible actions of the neurotoxic compounds include inhibition or disruption of normal cell metabolism including metabolism of glucose, the production of ATP, and maintanance of ion gradients across cell membranes including Na+, Ca++, and K+ ion channels, the synthesis of proteins and nucleic acids, and mitochondrial respiration.

Figure 3:
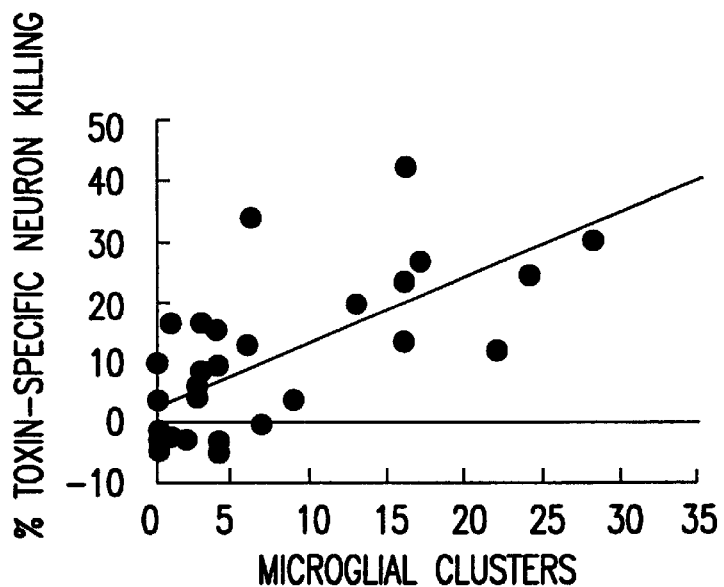
FIG. 3 shows the correlation between microglial clusters found in Alzheimer brain and levels of extracted neurotoxins. NTox was isolated from tissue blocks by aqueous extraction and 2-step ion exchange chromatography (DOWEX and SP-SEPHADEX) while neighboring portions of adjacent tissue stained for HLA-DR(+) microglial clusters (scored as mean number of clusters per $mm^2$ in 50 random field. Spearman rank correlation was highly significant (n=71 tissue regions from 6 brains; $r_s$<0.0005) suggesting that significant amounts of NTox are found in Alzheimer brain within brain structures laden with reactive microglia.
Figures 4A, 4B:
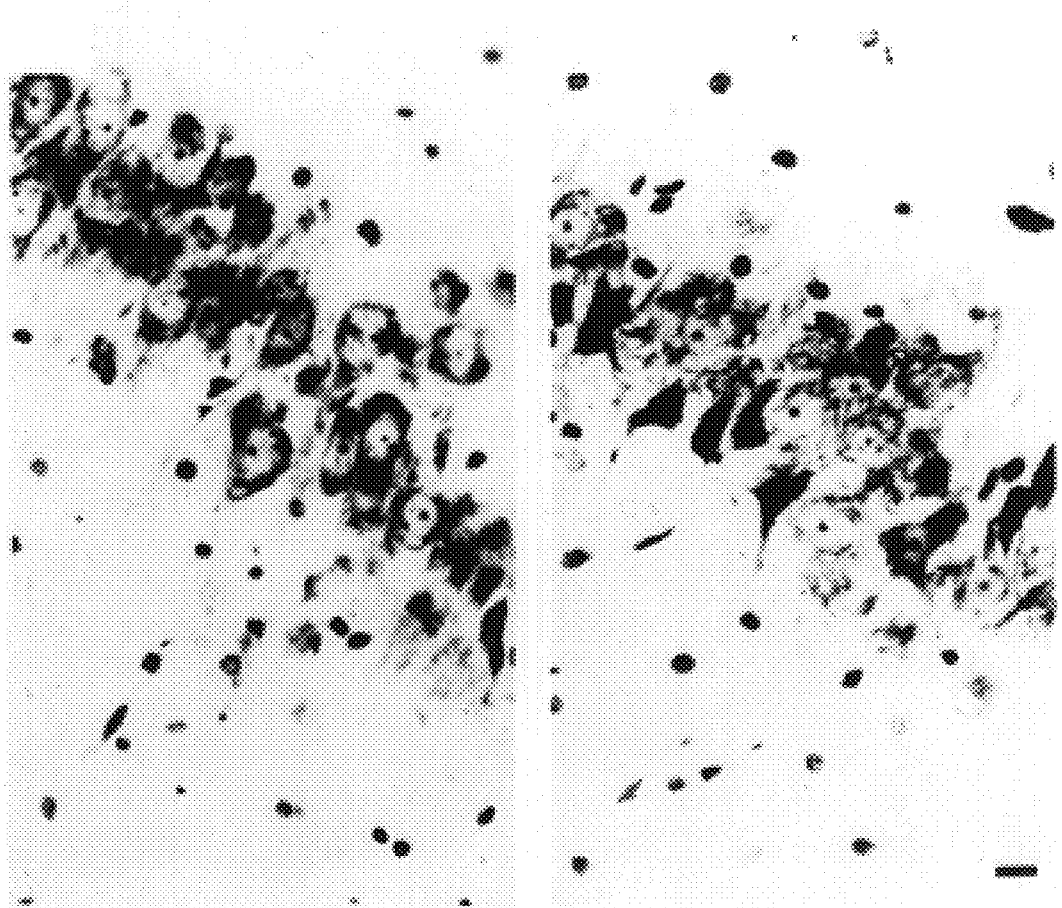
FIGS. 4A and B sets forth the results of neurotoxin infused directly into rat brain kills neurons in vivo. Nissl stained rat hippocampus (CA3 region) 5 days after stereotaxic injection of neurotoxin. Dead and dying, pyknotic neurons are readily apparent as darkly stained, shrunken profiles in the side injected with a neurotoxin recovered from Alzheimer brain (FIG. 4B; Bar=40 micron), compared to the contralateral hippocampus injected with an identical non-toxic fraction from age matched normal brain (FIG. 4A). The inventor estimates about 100 pmoles of purified neurotoxin were contained in the 1.0 $\mu$l fluid volume injected into the hippocampus.

The phenolic amine, NTox, (FIG. 1) has been highly purified from Alzheimer Disease brain at >100,000 fold (FIG. 2). Levels of NTox within brain regions correlate to the number of reactive microglia clusters found in the same brain regions (FIG. 3). Importantly, NTox isolated from Alzheimer Disease brain destroys neurons when infused into the brains of animals (FIG. 4). The concentrations of NTox found in Alzheimer Disease brain are very high and suggest that this particular toxic agent accounts for neurodegeneration which occurs in Alzheimer Disease. Thus, prevention of plaque activation of microglia would suppress production of NTox and reduce or prevent brain damage found in Alzheimer Disease.

The cascade of events may take place as a result of one plaque component binding to a mononuclear phagocyte, or more than one plaque component binding at complex formation or a series of plaque components continuing to bind during any of the cascade events.

Any agent (also referred to herein as a test compound), compound, compounds, mixture, complex, blend, combination of atoms, elements, chemicals, biological materials including and not limited to peptides, proteins, nucleic acids, and nucleotides suspected of having inhibitory activity to one of the events in the cascade may be screened in accordance with the methods of the present invention. An effective amount of a mononuclear phagocyte and a plaque component is the amount of each normally resulting in an event in the cascade, but for the addition of a suspected inhibitory agent. An effective amount is known to skilled artisans once armed with the present disclosure and will vary depending on the use of a mononuclear phagocyte, neuron, plaque component or components, the mammalian origin of the cells. The mammals useful for in vivo screening in accordance with the present invention include and are not limited to primates such as and not limited to monkey, chimpanzee, and ape, rodents, such as and not limited to rat and mouse, guinea pig, dog, cat, rabbit, and pig. In vivo assays performed in accordance with the methods of the invention include human central nervous system tissue, such as brain. The plaque component source useful in the present invention includes plaque of a patient suspected of having Alzheimer Disease, hereditary hemorrhage with amyloidosis-Dutch type, cerebral amyloid angiopathy, cerebral amyloid angiopathy, Down's syndrome, spongiform encephalopathy, Creutzfeld-Jakob disease, HIV, Parkinson's disease, multiple sclerosis, amyotrophic lateral sclerosis, stroke, or trauma.

An effective amount of time for contacting a mononuclear phagocyte with a plaque component and an agent suspected of inhibiting the mononuclear phagocyte-plaque component complex formation is the amount of time in which inhibition of complex formation is observed and includes for example the amount of time the complex forms under conditions in which the suspected inhibitory agent is not present.

For purposes of the present invention, inhibition and variations thereof are used herein synonymously with reduce, suppress, retard, slow, and suspend. Further, agents may be identified that completely inhibit any of the events in the cascade such that the event is arrested, stopped, or blocked. In accordance with the present invention, a cell, such as a mononuclear phagocyte and a neuron, which is inhibited is one which is unable to display the event typically seen in that cell type under typical cascade conditions. Typical cascade conditions are conditions that do not include an agent suspected of inhibiting the cascade event. Accordingly, the present invention includes the identification of agents that substantially inhibit any of the cascade events. Substantial inhibition of events in the cascade refers to less than about 1% to about 100% of the cells of a given population that are inhibited. Preferably a cascade event is inhibited about 10%, more preferably about 20%, more preferably about 50%, even more preferably about 75%, even more preferably about 100%.

Measuring formation of a mononuclear phagocyte-plaque component complex may be achieved by any of the standard methods known in the art. Examples of the typical methods include imaging and detection of amplified nucleic acids. An initial rapid screen of Aβ binding to microglia in vitro, for example is based upon the fact that specific domains of the Aβ peptide are essential for Aβ-microglia interactions. A plaque component, mononuclear phagocyte, agent, or solid support used in any of the detection methods of the present invention, may be tagged by various methods to allow detection. These methods include and are not limited to chemical radiolabeling (such as modifications with $^{125}$Iodine, such as at tyr10), synthetic incorporation of radiolabels during synthesis of peptides (such as amino acid or side chain modifications containing, for example, $^{14}$Carbon, $^3$Hydrogen, or $^{35}$Sulfate), coupling to solid supports which themselves are tagged (such as the use of Aβ coupled to fluorescent microspheres, peptide labeling with fluorescent tags, such as and not limited to rhodamine and fluorescein, modifications of peptides to allow for detection via ligand binding, such as and not limited to biotinylation for biotin-avidin detection methods and anti-digoxigenin antibody detection) and enzymatic methods wherein for example enzymes are coupled to colorometric displays such as and not limited to the peroxidase detection method.

Figure 5:
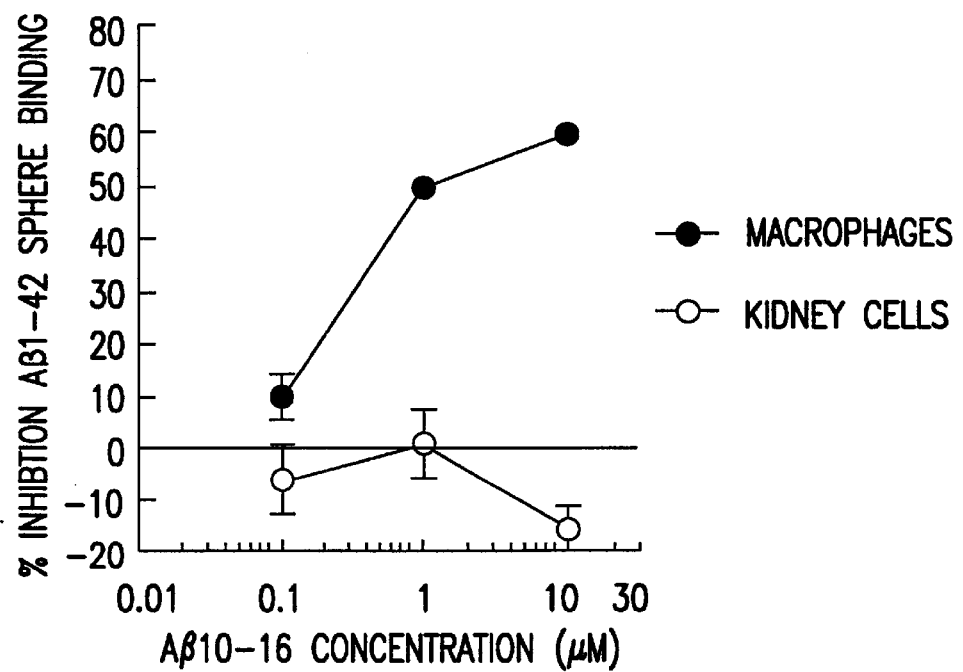
FIG. 5 shows the specificity of A$\beta$1–42 to macrophages is seen by comparison with incubating either macrophages or kidney cells with microspheres coupled to A$\beta$1–42 for 4 hours at 37° C. in the presence of increasing amounts of A$\beta$10–16 mixed with the culture media. As shown, competition occurs with the macrophages in a dose dependent manner while no changes in binding are seen for kidney cells. These and similar data indicate a specificity for A$\beta$ binding to in microglia, macrophages, and other classes of microglia-like cells.

To determine if Aβ peptide selectively bound to microglial surfaces, Aβ peptides were coupled to microspheres and incubated with cultures of microglia. Microspheres coupled to Aβ1–42, but not Aβ17–43, were readily engulfed by microglia. Comparisons among various sequences with the Aβ1–42 peptide revealed that those peptides encompassing residues to 16 were essential for Aβ binding to microglia. Importantly, this binding shows specificity (selective competitive against free Aβ1–42) and demonstrates cellular selectivity to microglia and other classes of mononuclear phagocytes (FIG. 5). The microglial binding sites for Aβ include cell surface associated molecules containing trypsin-sensitive protein component and a heparan sulfatase sensitive component.

Mononuclear phagocyte-derived binding sites may be presented in a screening assay in several ways such as and not limited to culturing of cells (microglia, microglia-like cell lines, macrophages, macrophage-like cell lines, or cell lines modified to express microglia-like surface molecules) in test chambers, adhering or coupling membranes to test chambers, or placement of specifically isolated membrane or chemical fractions from microglia or macrophages which contain the relevant Aβ binding component that a) show a specificity of binding to plaques and/or Aβ peptides which contain the sequence of the HHQK domain, SEQ ID NO: 1 and b) show involvement in complex formation. Mononuclear phagocytes may be labeled biosynthetically or by chemical or enzymatic methods to tag a mononuclear phagocyte-derived element involved in forming a complex with a plaque component. These and other strategies for labeling either plaques, peptides, or cells are known by those familiar in the art and contemplated by the present invention. Examples of assays include and are not limited to:

Cell associated binding assays comprise a test agent mixed with tagged plaque, Aβ, or microglia-derived binding site. Complex formation blocked by a test compound may be indicated by a reduction in recovery of tagged materials within a formed complex when compared to a control.

A tissue slice binding assay comprises mixing an agent suspected of having inhibitory activity to a cascade event with a tagged plaque component and tissue sections of normal and abnormal mammalian brain, for example, a human tissue sample from an Alzheimer Disease patient. Blockade of complex formation by a test compound may be observed by a reduction of tagged materials, (labeled, for example with a radiolabel, fluorescent dye, or enzyme) within formed complexes when compared to a control.

Figure 6A:
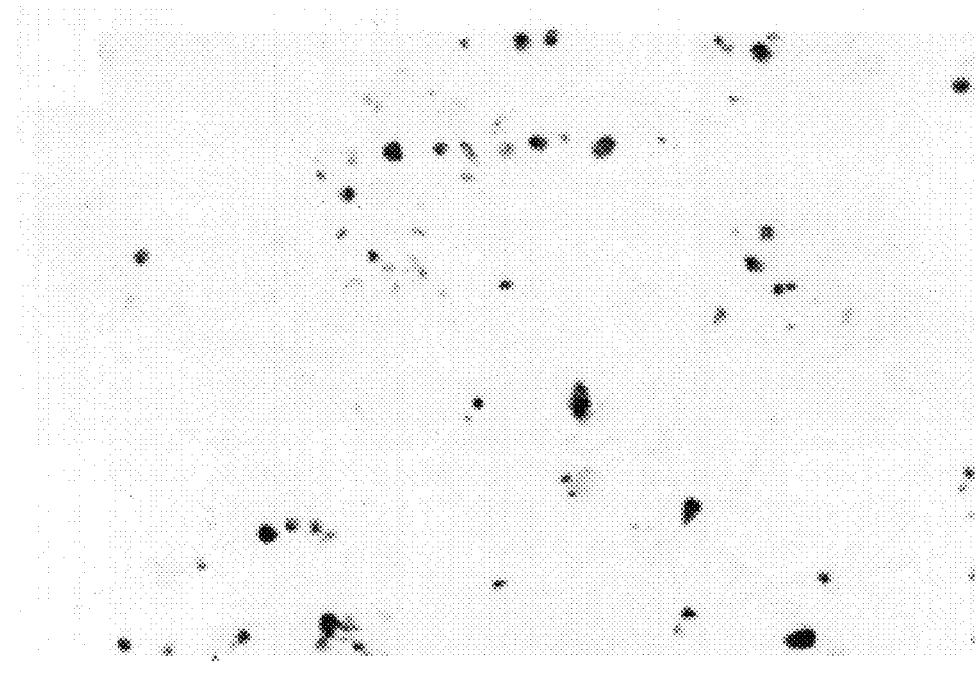
FIGS. 6A and B shows twenty four hour exposure of human embryonic kidney (HEK) cells to 1 nM of NTox resulted in significant cell death as measured by trypan blue staining but only in those cells expressing heteromeric NMDA receptors.
Figure 6B:
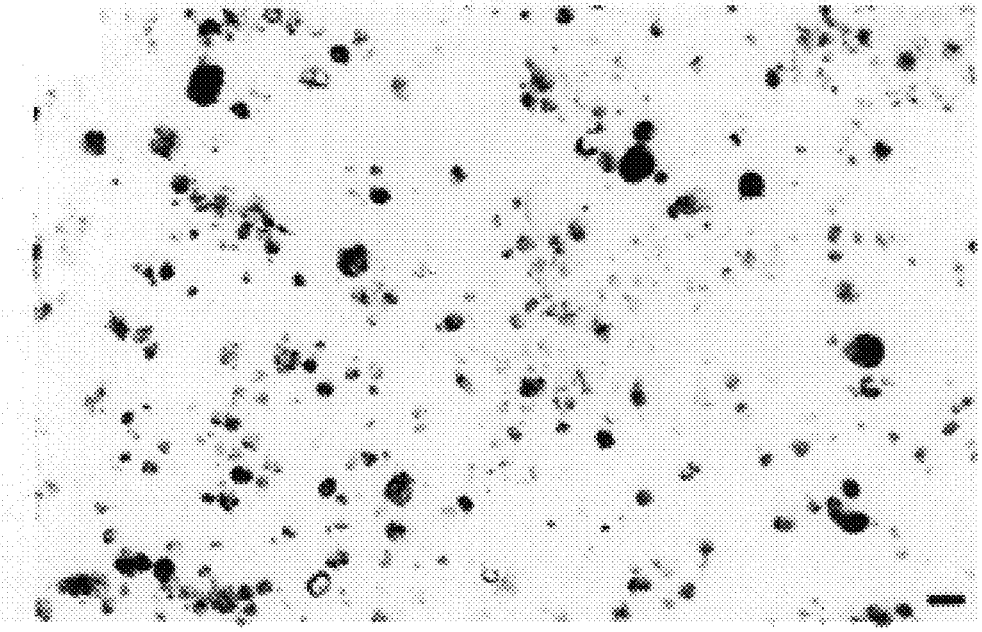
FIG. 6B shows HEK cells expressing NMDA1b/2A were also exposed to NTox for 24 hours. As seen, far larger number of dying cells appear. This NTox killing effect was found in heteromeric expression (R1/R2) and could be blocked by MK-801.

In vitro neurotoxicity assays detect an inactivator of a neurotoxic mononuclear phagocyte and employ cultures of neurons, neuron-like cell lines, or cells which have been modified to express N-methyl-D-aspartate receptors (FIG. 6). Presence of neurotoxic activity will be determined by reduction in cell number, changes in biochemical markers such as loss of cell metabolic function, release of intracellular material, penetration of impermeant dyes, such as and not limited to fluoresecent nuclear dyes and trypan blue (FIG. 6), reduction of the number of neurons, loss of neurofilament or synaptophysin, release of lactate dehydrogenase, or other evidence of cell injury. These and other strategies for identifying cell neurotoxicity, which may be displayed as cell injury, are known by those familiar in the art and contemplated by the present invention.

Figure 7A:
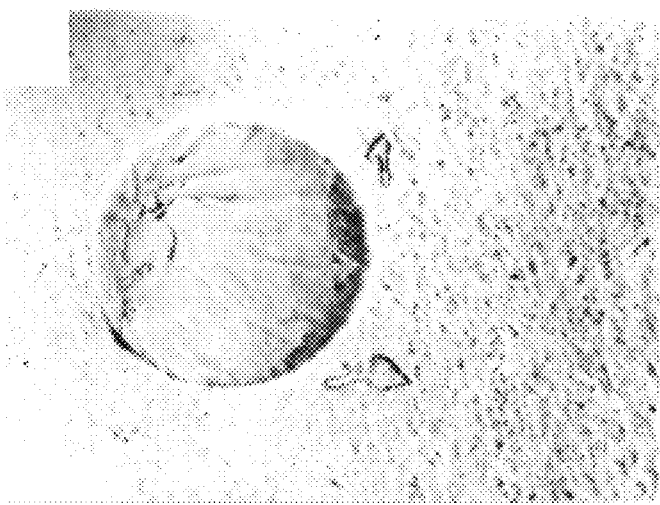
FIGS. 7A, B, and C show Spheres$_{A\beta1-42}$ in vivo. Weeks after implantation of large microspheres (250 micron diameter) remain embedded within brain neocortex (FIG. 7A).
Figure 7B:
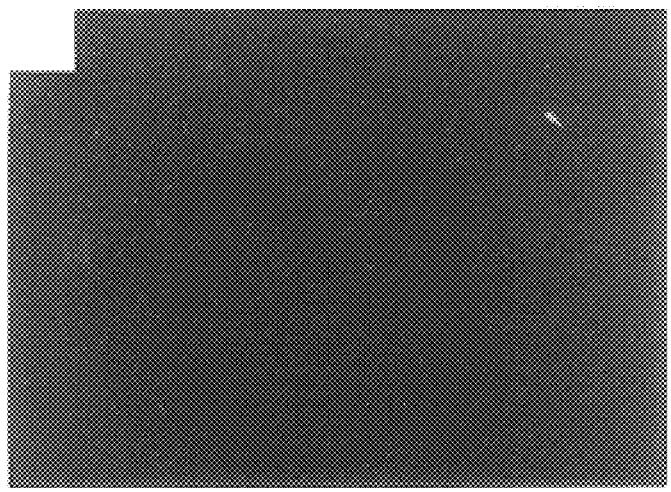
FIG. 7B shows an implanted Sphere$_{BSA}$ with very few scavenger receptor(+) microglia abutting the control microsphere. In contrast, Spheres$_{A\beta1-42}$ chronically stimulate the presence of reactive cells (FIG. 7C). Microglia were visualized by uptake of fluorescent labeled acetylated LDL, DiI-ac-LDL Bar=40 $\mu$m, FIG. 7A; 25 $\mu$m FIGS. 7B and C.
Figure 7C:
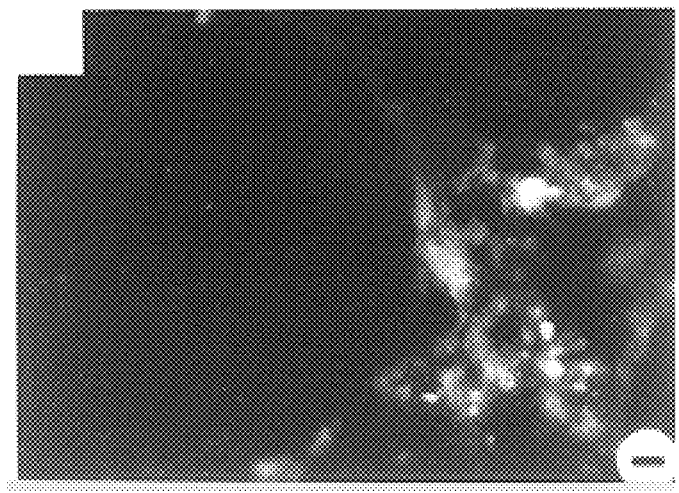
Figure 8A:
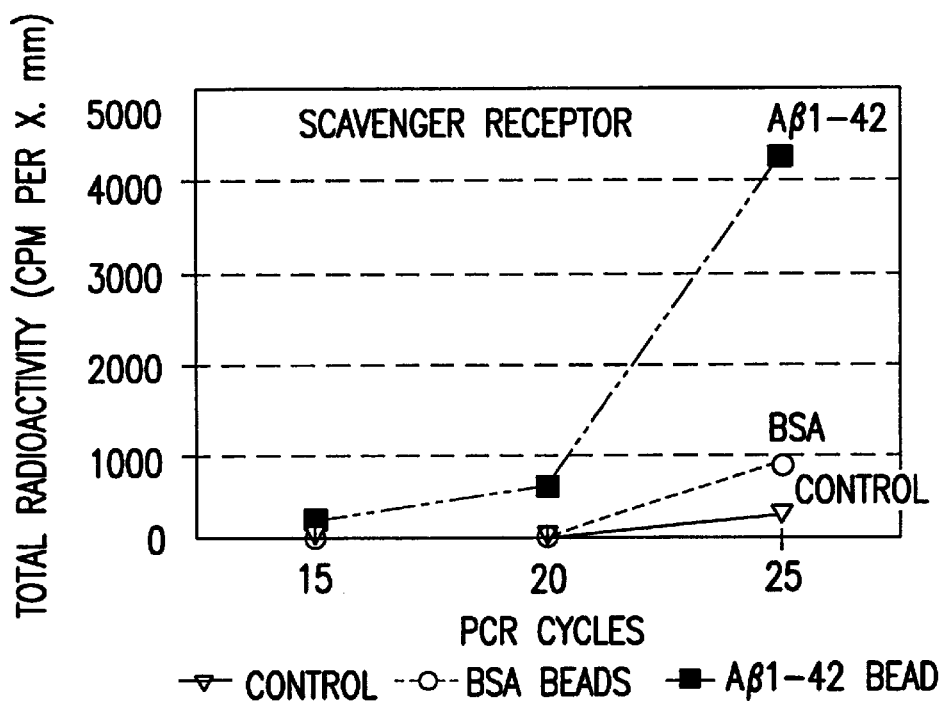
FIGS. 8A and B shows scavenger receptor II mRNA in tissue surrounding sphere implants.
Figure 8B:
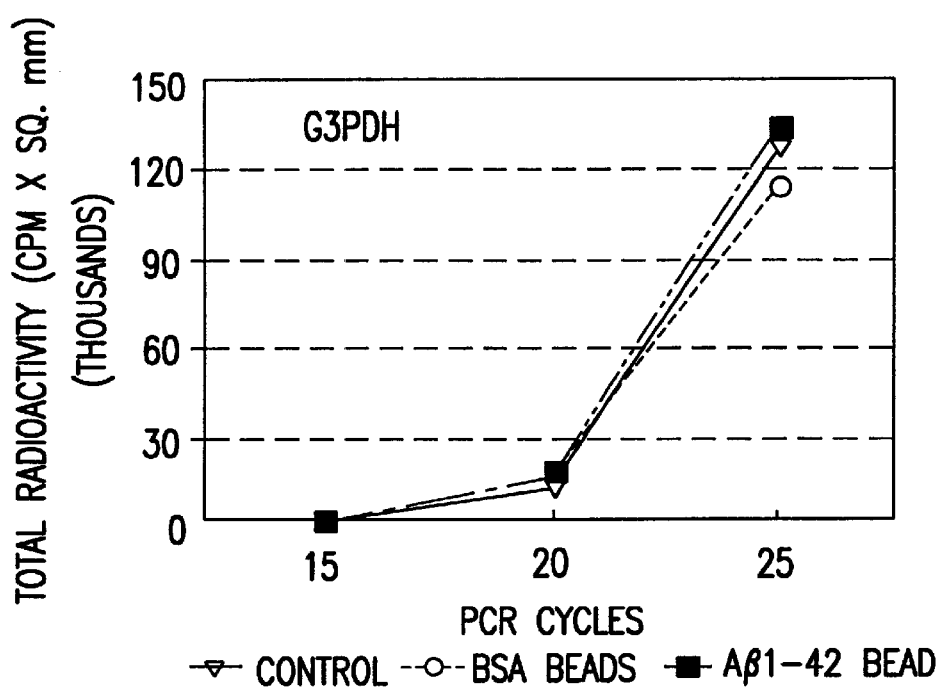
FIG. 8B, in contrast, reveals that all sites had similar levels of the marker mRNA G3PDH. Data support histological changes.

In vivo binding, activation, and neurotoxicity assays involve infusion of a tagged plaque component coupled to a solid support such as microspheres (FIG. 7) into a mammalian brain. Following infusion of materials, a test compound may be co-injected into the brain intraventricularly or intracranially by cannula with delivery systems including syringes or implanted osmotic pumps. A test compound may also be delivered systemically by intraperitoneal, intravenous, intraarterial, nasal, or oral routes. Evidence of immune activation of the brain by a plaque component may be monitored using histological, biochemical, or molecular methods such as quantitative reverse transcriptase polymerase chain reaction method to identify cell markers of immune responses including surface proteins, enzymes, or cytokines (FIG. 8). The production of neurotoxic activity may be assayed by histochemical (FIG. 7) or biochemical to identify cell markers of immune responses including injury or destruction of neurons. Neurotoxicity assays may observe a loss of metabolic function, release of intracellular materials, penetration of impermeant dyes, and reduction in neuronal cell numbers.

Other methods of detecting a neurotoxin blocker include detecting the inhibition of normal cell metabolism include discruption of 1) glucose metabolism, 2) ATP production, 3) ion gradient maintenance across cell membranes, 4) protein synthesis, nucleic acid synthesis, and mitochondrial respiration. Reductions in an inflammatory marker or injury to a neuron by a test compound may be compared to a control.

In addition, methods of detection amplified nucleic acids are known to skilled artisans once armed with the present disclosure. A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., 1990. In addition, other methods known to skilled artisans for amplifying nucleic acids may be used in place of PCR, such as and not limited to LCR disclosed in EPA No. 320,308, Qbeta Replicase, described in PCT Application No. PCT/US87/00880, isothermal amplification methods, disclosed in Walker, G. T., et al., 1992, transcription-based amplification systems (TAS) (Kwoh D., et al., 1989, Gingeras T. R., et al., PCT Application WO 88/10315, including nucleic acid sequence based amplification (NASBA) and 3SR, Davey, C., et al., European Patent Application Publication No. 329,822, disclose a nucleic acid amplification process involving cyclically synthesizing single-stranded RNA ("ssRNA"), ssDNA, and double-stranded DNA ("dsDNA") which may be used in accordance with the present invention. Miller, H. I., et al., PCT application WO 89/06700, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., 1990) and "one-sided PCR" (Ohara, O., et al., 1989).

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

Mononuclear phagocyte specific nucleic acids can also be detected using a cyclic probe reaction (CPR). In CPR, a probe having a 3' and 5' sequences of non-mononuclear phagocyte specific DNA and middle sequence of mononuclear phagocyte specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to an mononuclear phagocyte specific expressed nucleic acid.

Still other amplification methods described in GB Application No. 2 202 328, and in PCT Application No. PCT/US89/01025, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Methods based on ligation of two (or more) oligonucleotides in the presence of nucleic acid having the sequence of the resulting "di-oligonucleotide", thereby amplifying the di-oligonucleotide (Wu, D. Y. et al., 1989), may also be used in the amplification step of the present invention.

The present invention also embodies adhering a plaque component or cell to a solid support. A solid support may be selected from any solid support known to skilled artisans such as and not limited to a microsphere, liposome, sepharose, sephadex, vesicle, microbubble, polymeric bead, and the like.

Agents detected by a process set forth herein for the detection of inhibitor of a mononuclear phagocyte-plaque component complex formation were in fact found to be inhibitory to complex formation. One plaque suppressor agent is identified herein as SEQ ID NO: 1, HHQK. Agents comprising HHQK, HHQK-like agents having HHQK activity such that they are inhibitory to complex formation include agents having a secondary or tertiary structure substantially similar to HHQK. Alternatively, HHQK-like agents or activity may be measured by similar hydrophobicity, hydrophilicity, acidity, and basicicity of the agent or side chains thereof. In addition, minor variations in the measurements identified herein are considered to be substantially similar to HHQK. Another plaque suppressor is heparan sulfate and heparan sulfate-like agents having heparan sulfate activity such that they are inhibitory to complex formation include agents having a secondary or tertiary structure substantially similar to heparan sulfate. Alternatively, heparan sulfate-like agents or activity may be measured by similar hydrophobicity, hydrophilicity, acidity, and basicicity of the agent or side chains thereof. In addition, minor variations in the measurements identified herein are considered to be substantially similar to heparan sulfate. A composition comprising heparan sulfate or a heparan sulfate-like agent is provided herein, such that the composition is provided in a pharmaceutically acceptable carrier in a therapeutically effective amount. Suitable pharmaceutical carriers are well known in the art and described, for example, in Gennaro, Alfonso, ed., Remington's Pharmaceutical Sciences, 18th Edition, 1990, Mack Publishing Co., Easton Pa., a standard reference text in this field. The particular amount of the compositions of the invention that will be administered to the mammal for any particular condition will depend on the type of illness, and other factors such as the weight and age of the patient and route of delivery.

Figure 9A:
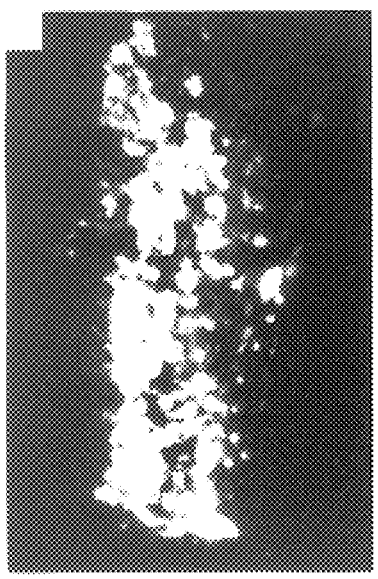
FIGS. 9A, B, and C shows infusion of A$\beta$1–42 into the neocortex of adult rat produces an inflammatory response 5 days later at the site of injection as seen by the presence of reactive microglia and macrophages labeled with DiI-ac-LDL (0.5 nmoles injected.
Figure 9B:
FIG. 9B reveals that co-infusion of 0.5 nmoles of A$\beta$1–42 plus 1.0 nmole of A$\beta$13–16 blocks the interaction of A$\beta$1–42 with microglia in vivo and reduces the local brain inflammatory response while co-infusion with 1.0 nmole A$\beta$1–5 did not alter inflammation (FIG. 9C, Bar=30 microns).
Figure 9C:
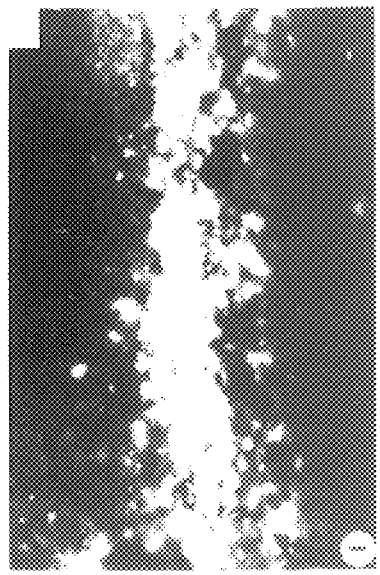

Screening various plaque components shows that the components containing the HHQK (SEQ ID NO: 1) sequence block Aβ binding to neurons and block neuron-killing elicited by plaques or Aβ peptides Dose response curves showed the HHQK peptide as one of the most potent plaque suppressor peptides identified. Similarly, screening of polysaccharides indicate that heparan sulfate (and not similar compounds such as dextran sulfate or chondroitin sulfate) block Aβ binding to microglia. To confirm the ability of HHQK to activation of microglia in vivo, Aβ1–42 was injected into the neocortex of rats in the presence or absence of Aβ13–16. As shown in FIG. 9, inflammation induced by Aβ1–42 in the brain was markedly reduced if Aβ13–16 were present. Thus, by a series of screening methods, two very different compounds, the peptide HHQK and polysaccharide heparan sulfate, have been identified as potential plaque suppressor agents for use as therapy for Alzheimer Disease.

Agents which inhibit plaque component induced neurotoxicity of a mononuclear phagocyte are referred to as inactivators of neurotoxic mononuclear phagocytes. One inactivator agent is identified herein as chloroquine. Agents comprising chloroquine, and chloroquine-like agents having chloroquine activity such that they are inhibitory to neurotoxic mononuclear phagocytes, include agents having a secondary or tertiary structure substantially similar to chloroquine. Alternatively, chloroquine-like agents or activity may be measured by similar hydrophobicity, hydrophilicity, acidity, and basicicity of the agent or side chains thereof. In addition, minor variations in the measurements identified herein are considered to be substantially similar to chloroquine. A composition comprising chloroquine or a chloroquine-like agent may be used in a similar therapeutic and pharmaceutic manner as set forth above for the plaque suppressor agents.

Figure 10:
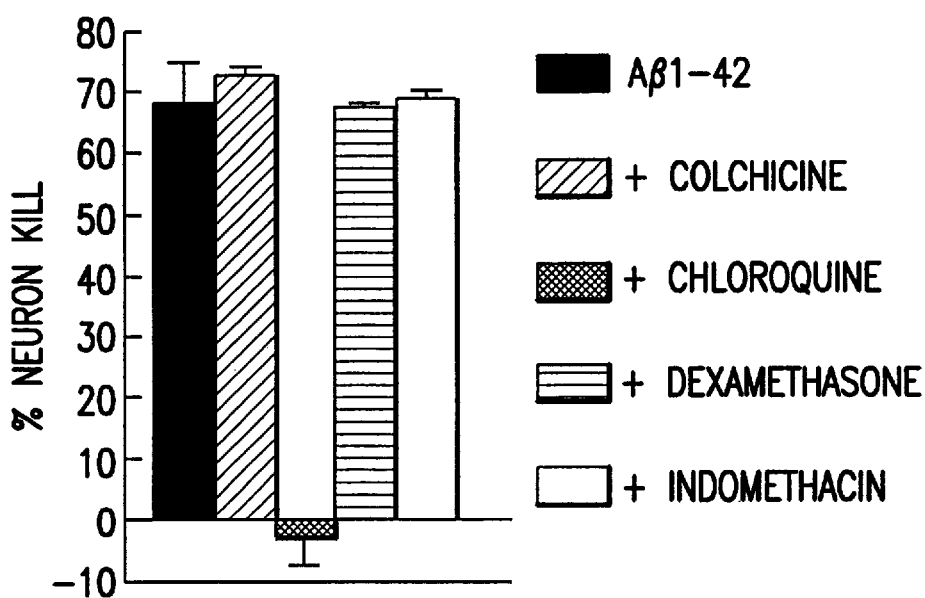
FIG. 10 shows in vitro screening of drugs which inactivate microglia stimulated by A$\beta$1–42. Test concentrations of immuno-suppressive drugs (0.1 to 10 $\mu$M) showed that only chloroquine had a protective effect and prevented appearance of neurotoxic microglia when mixed with A$\beta$ peptides. Such in vitro assays permit rapid screening of drugs with therapeutic potential for Alzheimer Disease.
Figure 11:
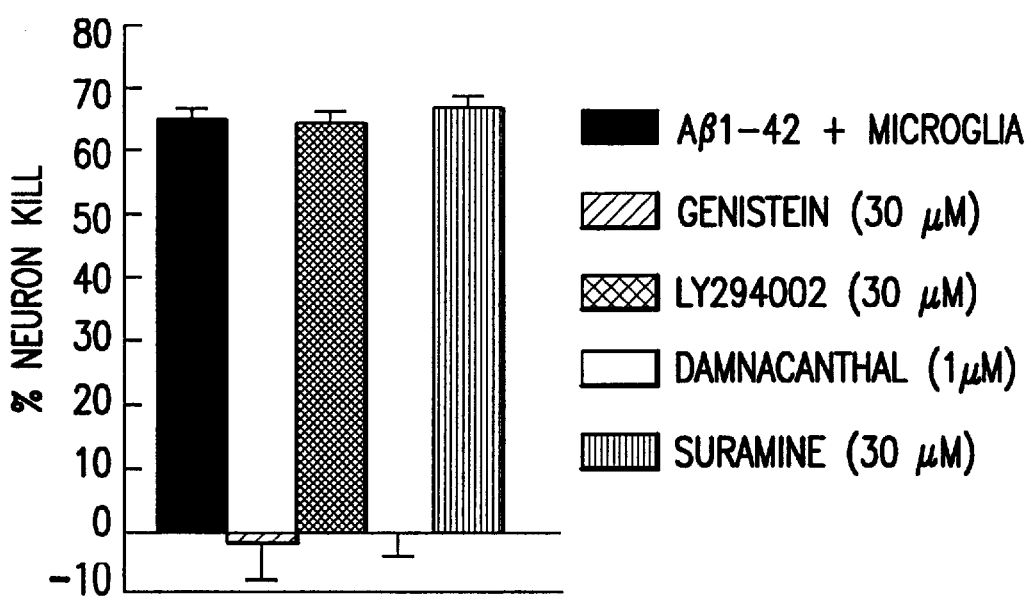
FIG. 11 shows in vitro screening of drugs which inactivate microglia stimulated by A$\beta$1–42. Test concentrations of signal transduction inhibitors (0.01 to 100 $\mu$M) showed that only compounds that block the tyrosine kinases (damacanthal and genistein) chloroquine had a protective effect and prevented appearance of neurotoxic microglia when mixed with A$\beta$ peptides. Such in vitro assays permit rapid screening of drugs which serve as lead compounds for development of therapeutics for Alzheimer Disease.

Once activated by plaque components, microglia release neurotoxic agents. Although many drugs are known to suppress the immune system outside the brain, it is not known which drugs actually have the ability to inactivative plaque-stimulated microglia within the brain and thus prevent the immune-mediated damage caused by Alzheimer Disease. Using the assay systems noted above, it is possible to screen for therapeutic agents that inactive neuron-killing microglia. As shown in FIG. 10, microglia incubated with chloroquine, unlike other immune suppressants such as dexamethasone, colchicine, or indomethacin, block neuron killing brought on by the presence of a plaque component or Aβ peptides. Activated microglia also require intracellular events signaled by signal transducers, to convert the plaque or Aβ complex formation with microglia into cellular events which lead to the production and release of neurotoxins including NTox. As shown in FIG. 11, agents that block tyrosine kinases (as opposed to other transduction pathways involving molecules such as GTP binding-proteins, protein kinase A, protein kinase C, phospholipases) prevent neuron killing. Thus, the use of the microglia-neuron assay systems allowed identification of specific drug families with value in the treatment of Alzheimer Disease.

Agents which inhibit plaque component induced neurotoxicity of a mononuclear phagocyte are referred to as a neurotoxic blocker. One blocker agent is identified herein as tyramine. Agents comprising tyramine and tyramine-like agents having tyramine activity such that they are inhibitory to neurotoxin effects on neurons, include agents having a secondary or tertiary structure substantially similar to tyramine. Alternatively, tyramine-like agents or activity may be measured by similar hydrophobicity, hydrophilicity, acidity, and basicicity of the agent or side chains thereof. In addition, minor variations in the measurements identified herein are considered to be substantially similar to tyramine. A composition comprising tyramine or a tyramine-like agent may be used in a similar therapeutic and pharmaceutic manner as set forth above for the plaque suppressor agents.

Figure 12:
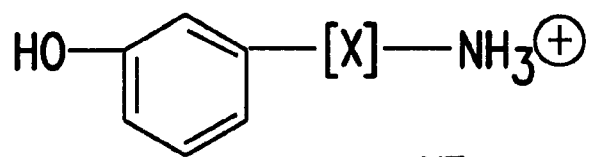
FIG. 12 shows a comparison of NTox with other brain-derived compounds which contain a phenolic and terminal amine group. Tyramine appears to significant structural similarity with NTox. Tyramine, however, has no known neurotoxic or neuroprotective properties.
Figure 12:
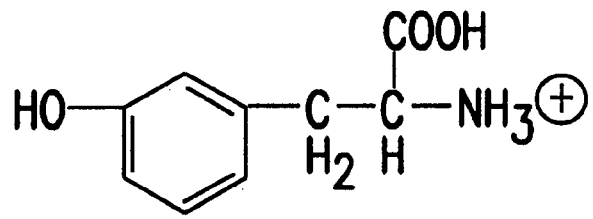
Figure 12:
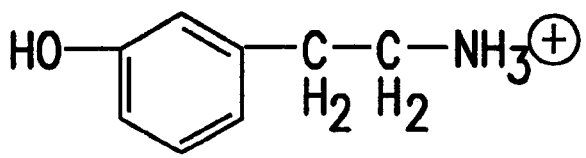
Figure 12:
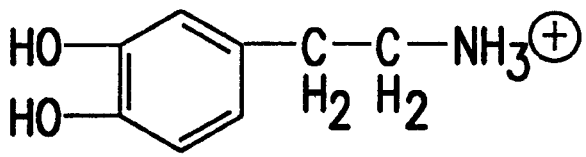
Figure 13:
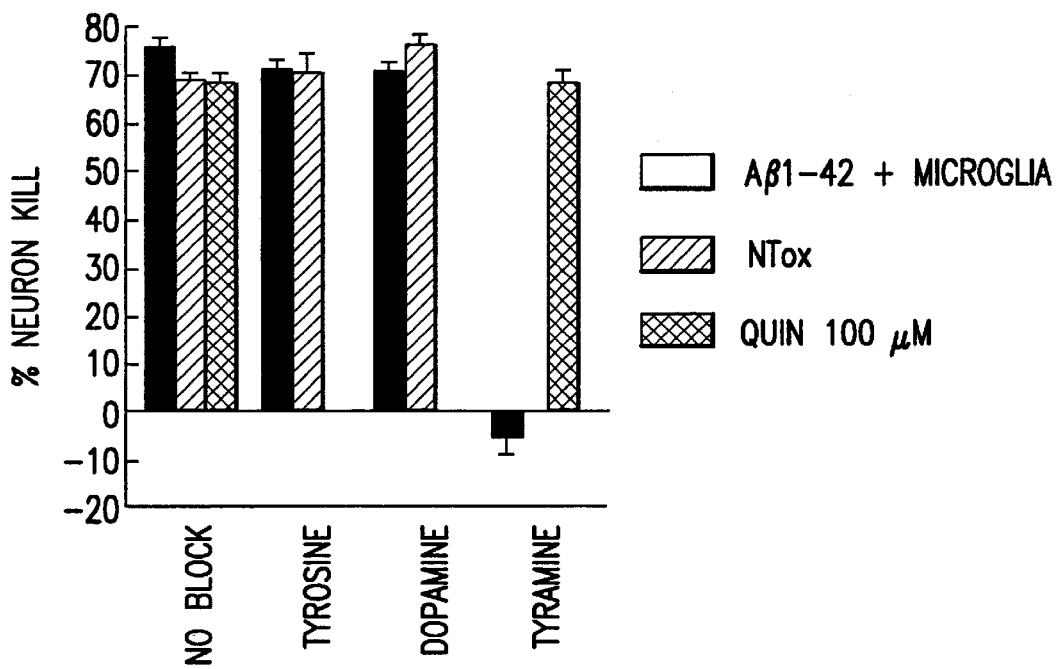
FIG. 13 reveals neuroprotective effects of NTox-like compounds. Test conditions include microglia stimulated with A$\beta$1–42, isolated NTox applied to neurons directly, or neurons mixed with 100 $\mu$M of the toxin quinolinic acid (QUIN). As shown, only tyramine prevented neuronal injury. Importantly, this protective effect did not occur with quinolinic acid which points to existence of families of molecules which could prevent microglia-mediated neuron injury.

Plaques and Aβ peptides stimulate microglia to release toxic phenolic amines referred to as Ntox. As shown in FIG. 12, NTox has structural similarities with a number of other compounds which contain a phenolic group and a terminal amine. As shown in FIG. 13, NTox released by Aβ1–42-stimulated microglia did not damage neurons in the presence of tyramine. Importantly, tyramine did not block other known neurotoxins such as quinolinic acid (FIG. 13) but appears specific for NTox and has, therefore, not been previously identified as a potential therapeutic compound for Alzheimer Disease.

As set forth herein, the primary signal for plaque induction of microglial neurotoxicity is the Aβ peptide. Plaque fragments from AD brain induce microglia to become neurotoxic, however only those solubilized plaque fractions which contained Aβ1–42 (or Aβ1–40) stimulate both rat and human microglia to take on reactive morphologies and become neurotoxic. Testing with synthetic peptides confirmed that the Aβ1–40 and Aβ1–42 peptides were inducers of neuron-killing microglia. Other forms of Aβ, including the peptides Aβ1–28, Aβ12–28, and Aβ17–43, were inactive. The physical state of the amyloid is not related to toxicity induction since rodent Aβ1–42, which does not induce toxicity, forms the same β-pleated sheets as does human Aβ1–42 (Fraser et al., 1992). In addition, Aβ17–42, which is even more prone to aggregation than is Aβ1–42 (Pike et al., 1995; TABLE 2), is also unable to induce toxicity. In fact, testing a variety of peptide fragments shows that the N-terminal and C-terminal regions appear to play separate and necessary roles in microglial activation. The interactions of microglia with peptide-coupled beads reveal that the N-terminus region is necessary, for anchoring of the peptide to the cells. This finding may account for the inability of rodent Aβ to induce neurotoxicity, since the first 16 amino acids of rodent Aβ are unlike the human Aβ domain. Interestingly, residues 1–16 compose the hydrophilic portion of the molecule and thus may be accessible for microglial attachment to the plaque. Without this attachment domain, Aβ is unable to induce toxicity and, in this way, prevented Aβ17–42 from activating microglia. The C-terminal portion of Aβ remains necessary to toxicity induction, however, since the N-terminus (1–16) alone was unable to induce microglial neurotoxicity.

It is important to note that the Aβ effects on microglial neurotoxicity set forth in the present invention are distinct from the direct neuron killing effects of Aβ described by other laboratories (Yankner, 1990; Pike et al., 1991, 1993; Cotman et al., 1992). Most laboratories exploring a direct toxicity carefully describe those specific cell culture conditions, or particular protocols for Aβ peptide preparation, which have been essential to create an environment for cell killing (Pike et al., 1991, 1993; Mattson et al., 1992; Howlett et al., 1995; Pollack et al., 1995). For example, low cell numbers appear to be necessary to demonstrate direct killing by Aβ, with cell densities typically <100 per mm$^2$ (Mattson and Rydel, 1992). In addition, toxic effects were only seen by other skilled artisans if cultures are exposed to the peptide after a defined period of incubation in vitro (Yankner et al., 1990), if glia are poisoned (Pike et al., 1995), if batch to batch variability among synthetic peptides is considered (May et al., 1992), if synthetic peptides are "aged" (Pike et al., 1991, 1993), or if glutamate or other glutamate receptor agonists are present (Koh et al., 1990; Mattson et al., 1992). Unfortunately, specific labeling for microglia (which may compose 5% to 10% of cells in embryonic rat hippocampal cultures) is seldom used, so the contribution of neurotoxic microglia to these other culture systems cannot be assessed.

The in vitro preparations useful in the present invention were optimized to maintain healthy and long-lived neuron/astroglia cultures, that were controlled to examine the role of microglial interactions with neurons. These cultures differed in several important ways from assays described by other investigators. First, the neurotoxicity assays employ high density cultures, an order of magnitude greater than the low density systems used by others. This condition is in agreement with Mattson and Rydel (1992), where no directly toxic effects of Aβ are observed. Secondly, the culture system is very supportive of neuronal growth as shown by extensive neuritic projections and viability for several weeks beyond the test period. In culture preparations poisoned with mitotic inhibitors or in very low density cultures, neuronal survival drops by at least 50% spontaneously, as observed by Mattson and Rydel, 1992, making it very difficult to monitor and interpret the effects of any cytotoxic agent. Thirdly, microglial content of the culture system must be clearly demonstrated, since the endogenous population of microglia present in primary hippocampal cultures is fully capable of arousal to neurotoxicity by Aβ1–42. Finally, a combination of neuron specific markers (MAP-2 and neurofilament) are employed to allow accurate monitoring of neurons among a mixed population of cells. In contrast, phase microscopy (which is very difficult to interpret in developing brain cell cultures), release of lactate dehydrogenase into culture media (which occurs after any cell damage), or a decline in neuron specific enolase (+) cells (which includes both neurons and glia in embryonic cultures) cannot differentiate the survival of neuronal and nonneuronal cells. While both the direct and indirect neurotoxic effects of Aβ may play roles in the neuronal pathology of AD, the striking potency of Aβ to induce neurotoxic microglia suggests that indirect, immune-mediated pathways may be substantial.

The present invention offers strategies for intervention in the pathology resulting from neurotoxic microglia in AD including (1) suppression of signaling steps as neuritic/core plaques turn quiescent microglia into reactive ones, (2) inhibition of microglial synthesis and secretion of neurotoxins, and (3) the blockade of neurotoxin attack upon neurons. In pursuit of the first of these strategies, specific domains of Aβ responsible for the various steps in the Aβ induced cascade of cellular response leading to neurotoxic microglia may be manipulated. Since the cell attachment domain in the N-terminal portion of Aβ is not itself toxic, induction of neurotoxic microglia by competition with small AD peptides may be blocked. Indeed, while anti-inflammatory drugs have been recommended as beneficial for AD (Breitner et al., 1990; McGeer et al., 1990; Schnabel, 1993; Eikelenboom et al., 1994; Lucca et al., 1994), the recommended drugs could not be properly assayed until the invention of the screening methods provided herein. In addition, microglial suppressants such as chloroquine are also indicated as a likely candidate (Giulian et al., 1989; Giulian and Robertson, 1990), since commonly used immuno-suppressants (including glucocorticoids) do not reduce neurotoxic activities of brain mononuclear phagocytes (Giulian, 1992). Finally, the neurotoxin secreted by plaque-activated microglia can be blocked by antagonists of the NMDA receptor. NMDA receptor antagonists useful for stroke, trauma, and epilepsy might now be screened for AD and may ultimately offer benefit to the AD patient. Inhibiting the Aβ activation of microglia offers a number of therapeutic interventions, all of which may slow neuronal loss in conditions associated with brain inflammation, including diseases such as Alzheimer Disease.

The following examples are illustrative but are not meant to be limiting of the invention.

EXAMPLES

A Tetrapeptide Domain within β-Amyloid Binds to Microglia and Suppresses Induction of Neurotoxicity by Alzheiiner Plaques In order to delineate the mechanisms by which Aβ plaques elicit neuron-killing microglia, the capacity of synthetic human and rodent forms of Aβ to act as microglial activators was monitored.

Rat microglia were isolated from newborn animals using the method of Giulian and Baker, 1986, with recovery of >98 % homogenous population monitored by binding the fluorescent probe acetylated low density lipoprotein labeled with 1,1'-dioctadecyl-3,3,3',3'-tetramethyl-indoarbocyanine [DiIac-LDL]). Amyloid proteins were isolated from AD neocortical gray matter laden with neuritic and core plaques with final separations involving a discontinuous sucrose gradient. Amyloid cores recovered from the 1.4/1.7 M sucrose interface as fragments (15 to 25 micron diameters) were solubilized in 80% formic acid and fractionated by Superose 12 FPLC to yield native Aβ (>99% in the Aβ1–42 form) in accordance with the methods of Lucca, U., et al., 1994. Cultured neurons prepared from rat hippocampus consisted of process-bearing neurons (10–20% of total cell population) atop a bed of astroglia (>70%) mixed with microglia (10%). In order to eliminate microglia, cultures were exposed saporin (a ribosome-inactivating protein) coupled to acetylated LDL (ac-LDL) for 10 pg/ml for 18 hours. Saporin-ac-LDL selectively bound to scavenger receptors and reduced microglial numbers to <0.1% of the total population, with no effect on numbers or viability of either neurons or astroglia. After 14 days in vitro, cultures (with a final concentration of 0.6% serum) were exposed to test substances in the presence or absence of exogenous microglia for 72 hours. At the end of this time, the cultures were fixed in 3% paraformaldehyde at room temperature for 6 hours and immuno-stained by overnight incubation with a mixture of anti-neurofilament antibodies (SMI-311, 1:150; RT-97, 1:150; Stemberger Monoclonals, Inc.) plus anti-MAP-2 (Boehringer Mannheim, 184959; 1:200) at 4° C. in the presence of 2% horse serum and 0.3% triton X-100. Data were expressed as % mean survival expressed in terms of parallel untreated control cultures after scoring at least 8 randomly selected fields for each of 3 coverslips from at least 3 independent experiments. Chemical modifications of Aβ1–42 (10 μmoles/1) were carried out at room temperature for 1 to 2 hrs with 5 mM CHD in 50 mm sodium borate buffer (pH 8.9); with 1 mm TNM in 50 mm Tris buffer (pH 8.0); with 10 mm EAM in 200 mm triethylamine HCl buffer (pH 10.0); and with 1 mm DEPC in 100 mm potassium phosphate buffer (pH 6.8). Decarbethoxylation involved the addition of 1.5 M hydroxylamine (pH 7.0) at room temperature overnight. Glutamine residues were enzymatically modified with 10 μg TNG in 100 mm Tris buffer (pH 7.4) containing 200 mm ethylamine at 37° C. for 2 hr. In all cases, samples were washed using ultrafiltration with Centricon 3 and added directly to cultures.

Figure 14C:
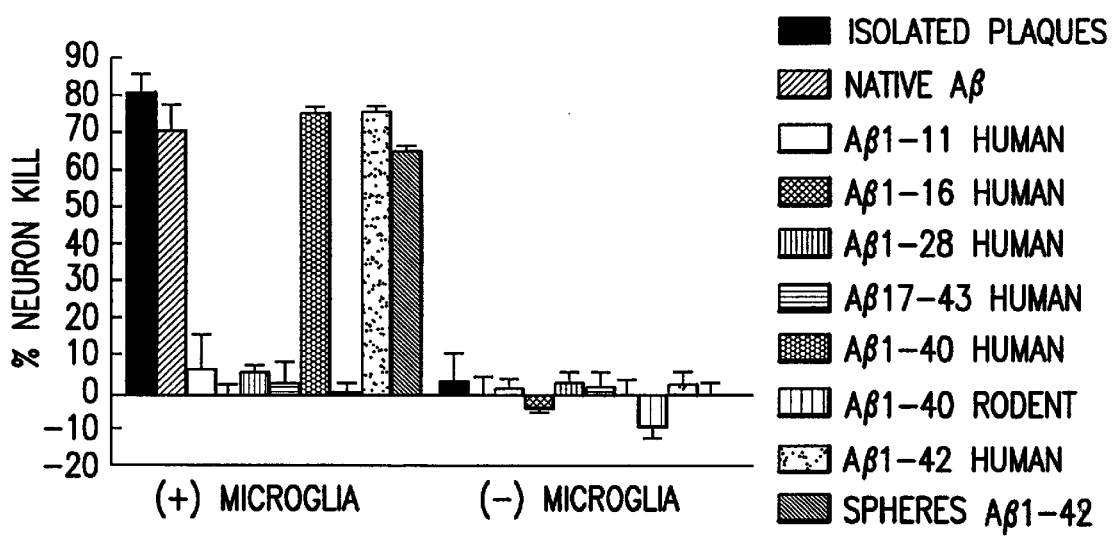
FIGS. 14A–D displays neurotoxic microglia activated by $\beta$-amyloid peptide.
Figure 14A:
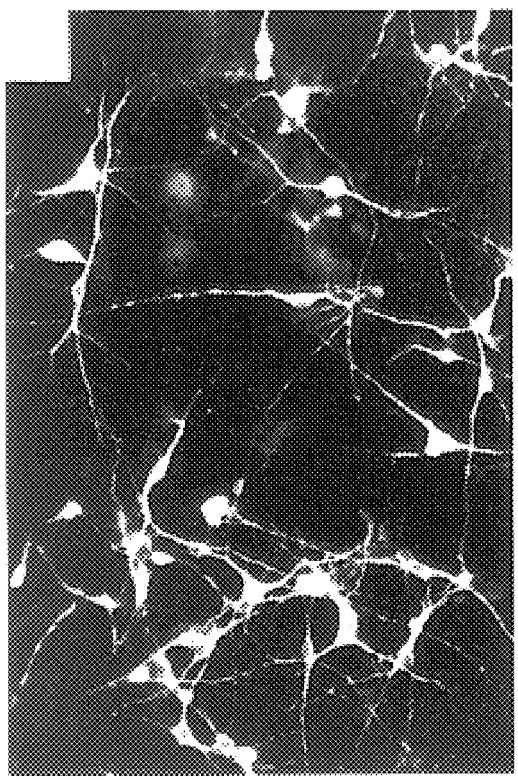
Figure 14B:
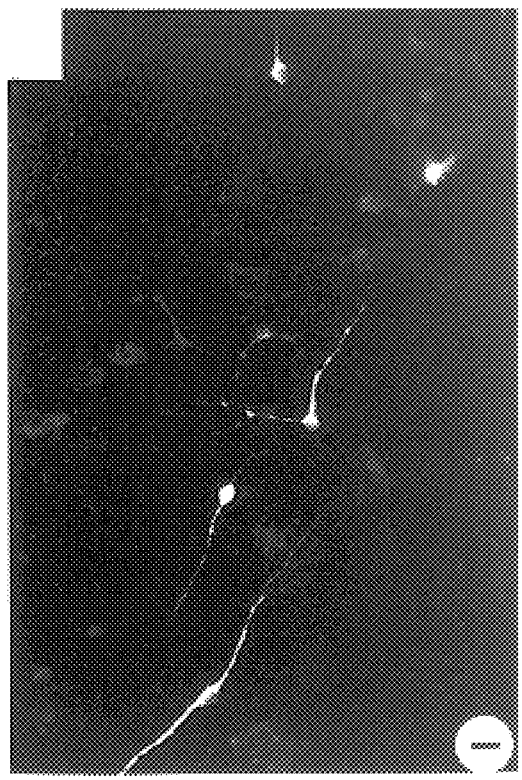
Figure 14D:
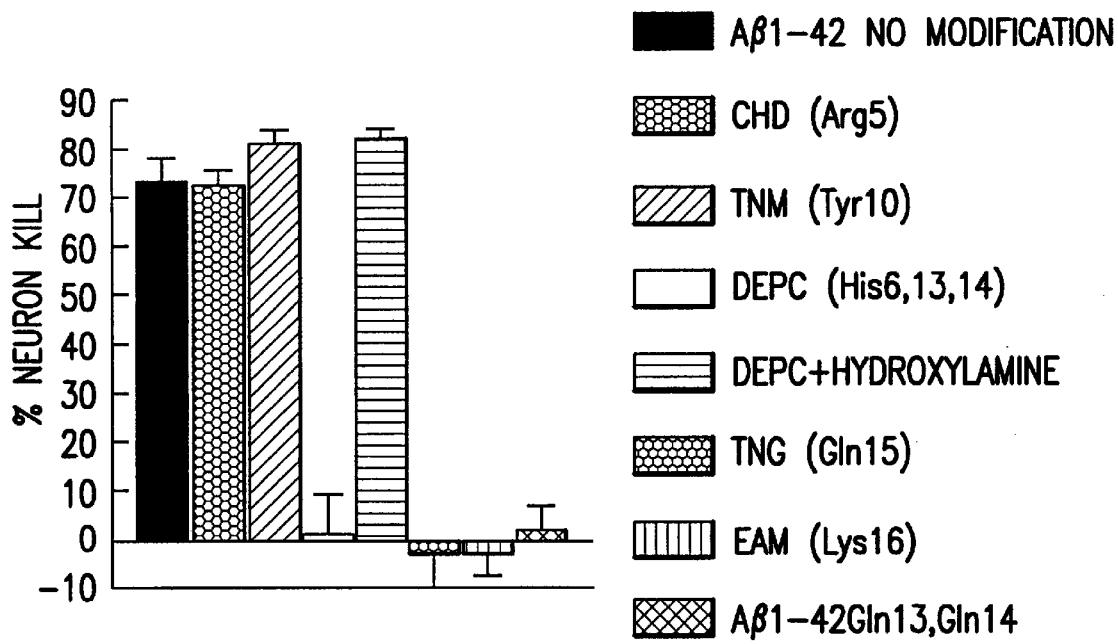

When applied at 1 μmole/1, human Aβ1–40 or 1–42 induced toxic effects upon dense hippocampal neuron cultures (1,200 cells per mm$^2$) that had been supplemented with microglia (500 cells per mm$^2$; FIGS. 14A, 14B, and 14C). Rodent Aβ1–40, which differs from human Aβ at residues 5, 10, and 13, did not activate microglia (FIG. 14C). Since these residues appeared to be necessary for induction of neuron killing, next human Aβ1–42 was chemically or enzymatically modified to mimic the rodent form. Cyclohexanedione (CHD) modification of the residue Arg5 or tetranitromethane (TNM) modification of Tyr10 had no effect upon AP activation of microglia (FIG. 27D). In contrast, diethylpyrocarbonate (DEPC) treatment of His6, His13, and His14 eliminated neuron killing. Reversal of the DEPC modifications by hydroxylamine restored Aβ as a stimulus and confirmed to the role of His residues. Exploring further the involvement of residues neighboring His13 and His14, both transglutaminase (TNG) cross-linking of Gln15 to ethylamine, and acetimidination of Lys16 by ethyl acetimidate (EAM) also blocked Aβ1–42 induction of neurotoxic microglia (FIG. 14D). The need for the 13–16 Aβ domain was confirmed by the synthetic peptide Aβ1–42$_{Gln13Gln14}$ which was unable to elicit neurotoxic responses (FIG. 14d). Thus, a combination of techniques indicate that residues His13, His14, Gln15, and Lys16 (the HHQK domain within Aβ) are required or induction of neurotoxic microglia. This domain by itself, however, is not able to induce neuron killing (see below).

Figure 15A:
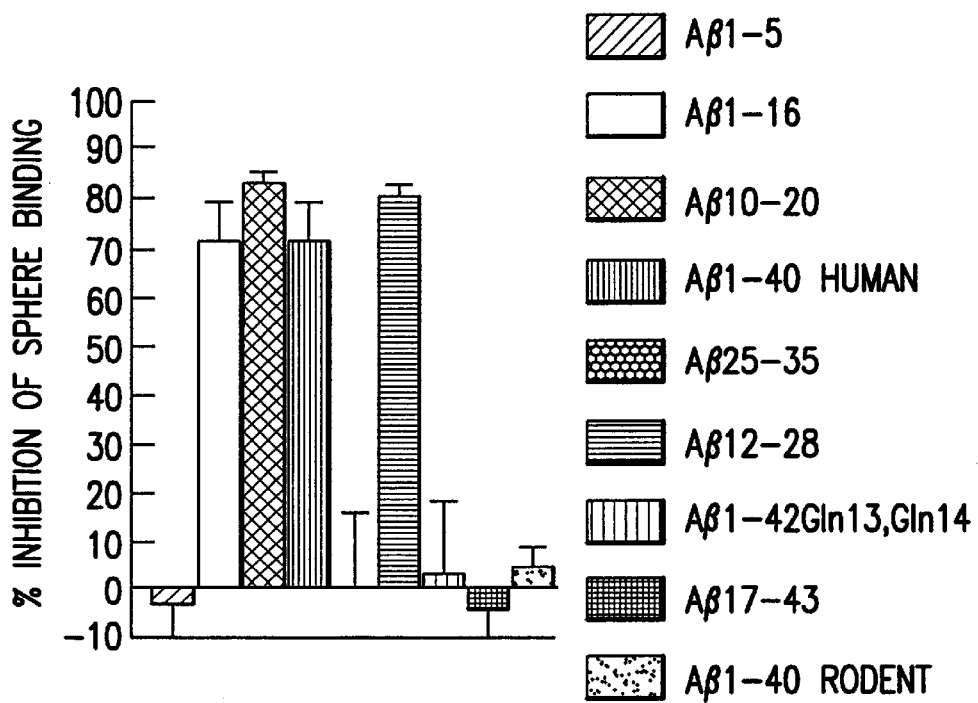
FIGS. 15A–D depicts inhibition of Aβ binding to microglia.

Previous studies on the conformation and solubility of synthetic Aβ peptides suggest that residues 1–16 make up a hydrophilic region which extend along the surfaces of Aβ fibrils. This hydrophilic region, moreover, is thought to provide binding sites for various plaque associated molecules. To determine whether the HHQK domain serves as a binding site to mediate Aβ interactions with reactive microglia, Aβ1–42 was coupled to fluorescent microspheres (1 μm diameters). The Spheres$_{Aβ1-42}$ were rapidly engulfed by cultured microglia and induced neuron killing in a manner similar to that of plaques or native Aβ (FIG. 14D). All peptides (10 μmoles/1) which contained the HHQK domain (Aβ1–16, 10–16, 1–28, or 10–20) effectively prevented microglial binding to Spheres$_{aβ1-42}$ while peptides lacking the HHQK domain (Aβ1–5, 1–11, 17–43, and 36–42) did not (FIG. 15A). Significantly, both rodent Aβ1–40 (containing His13-Arg) and human Aβ1–42 $_{Gln13, Gln14}$ were unable to block microglial adherence to Spheres$_{Aβ1-42}$. Together, these data point to the participation of the HHQK sequence during plaque contact with microglia.

Isolated microglia (1000 per mm$^2$) were placed atop 16 mm glass coverslips in 24-well culture plates. Each well then received 250,000 Spheres A$_{Aβ1-42}$ or Spheres$_{mal-BSA}$ in the presence or absence of Aβ peptides, GAGs, or scavenger receptor ligands. Binding assays were carried out at 37° C. for 4 hours after which coverslips were dipped 10 times in phosphate buffer and fixed with 4% buffered paraformaldehyde. Microsphere adherence to cells was scored at 200 magnification with phase/fluorescence microscopy. Data, expressed as % inhibition of sphere binding, was calculated from total number of spheres per field noted for control cultures receiving spheres only. Values are based upon at least 3 coverslips from 2 independent experiments. Fluoresbrite carboxylate YG microspheres (1.0 micron diameters; 0.5 ml of a 2.5% suspension) were activated with 1% carbodiimide for 4 hr at room temperature. Washed spheres were resuspended in 0.2 M borate buffer (pH 8.5) in the presence of 300 μg Aβ or 400 μg BSA in 6% DMSO. After overnight mixing at room temperature, the spheres were washed extensively and blocked by 1 M glycine (pH 8.0) for 30 minutes. Maleylation of coupled BSA was carried out at room temperature by adding 1 M maleic anhdyride in acetonitrile at pH 9.0.

Figure 15B:
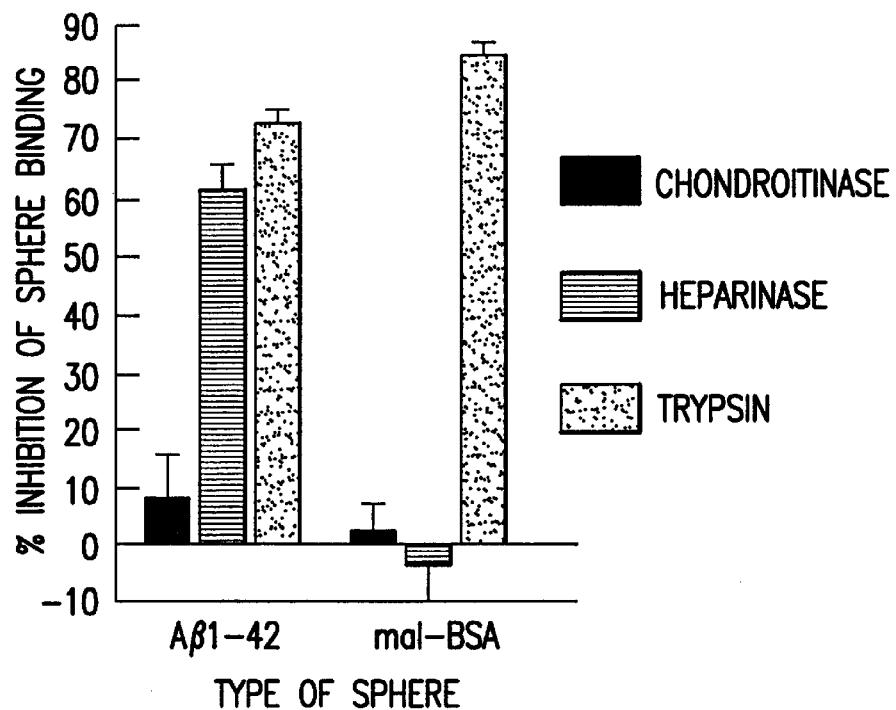
Figure 15C:
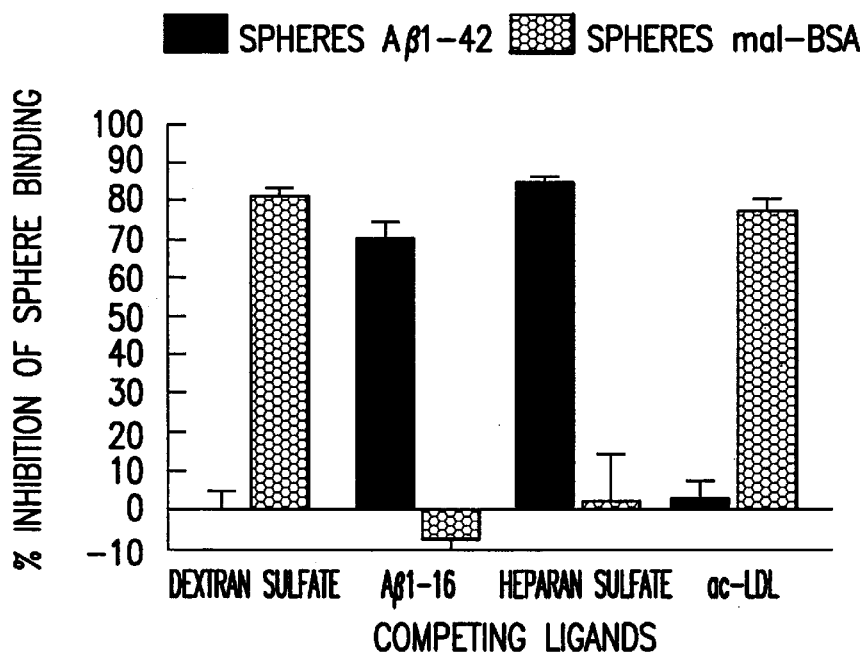

Spheres$_{Aβ1-42}$ binding to microglia was markedly reduced by trypsinization of intact cells (FIG. 15B), suggesting that peptide-cell interactions were mediated by microglial surface proteins. Potential microglial binding sites include a variety of cell surface proteins which are expressed as microglia become reactive. One example is the dramatic appearance of scavenger receptors within hours after traumatic or ischemic CNS injury. Christie et al have, moreover, found an increased expression of scavenger receptors among reactive microglia associated with plaques in AD brain. To assess the role of the scavenger receptor in Aβ-microglia interactions, BSA was coupled to microspheres and then modified the coupled protein to produce maleylated-BSA (Mal-BSA), a known scavenger receptor ligand. By monitoring microglial binding to Spheres$_{Aβ1-42}$ or Spheres$_{mal-BSA}$ in the presence of scavenger receptor ligands, it was, possible to determine whether this receptor provided a recognition site for Aβ. When microglia were incubated with Spheres$_{Aβ1-42}$ and heparin sulfate, chondroitin sulfate, acetylated low density lipoprotein (ac-LDL), or dextrn sulfate, only heparin sulfate blocked Spheres$_{A\beta1-42}$ binding to microglia. In contrast, scavenger receptor ligands such as ac-LDL and dextran sulfate blocked Spheres$_{mal-BSA}$ binding (FIG. 15C). Moreover, Aβ1–16 selectively suppressed Spheres$_{A\beta1-42}$ binding but did not affect microglial interactions with Spheres$_{mal-BSA}$. Trypsinization of cells reduced binding of either type of coupled microsphere while pretreatment of microglia with heparinase selectively eliminated Spheres$_{A\beta1-42}$ binding (FIG. 15B). Chrondroitin sulfatase did not alter the microglia binding to either Spheres$_{A\beta1-42}$ or Spheres$_{mal-BSA}$. These data suggest that heparin sulfate on the surface of microglia provides an anchoring site for human Aβ which is independent of the scavenger receptor.

Figure 15D:
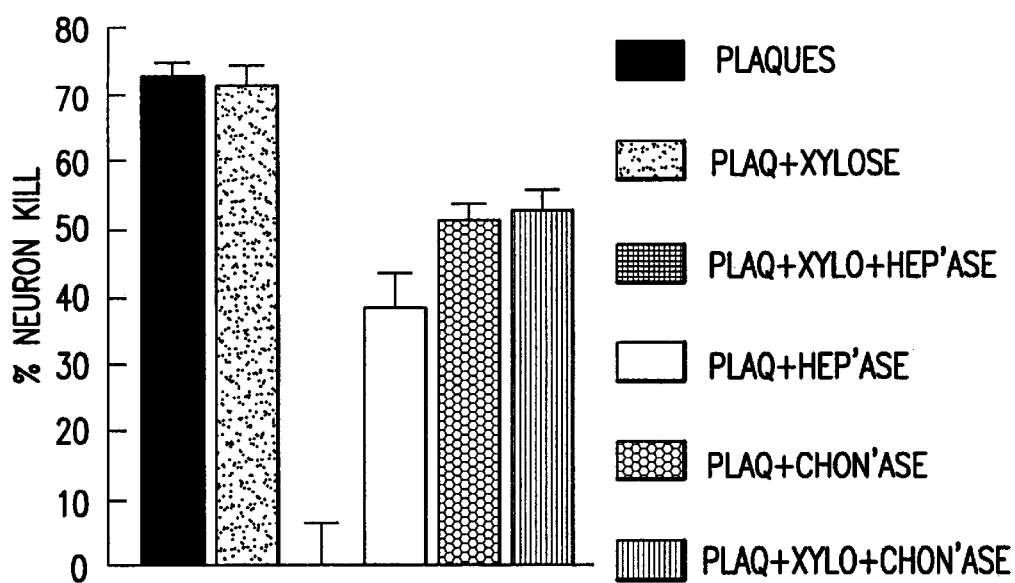

To determine if the heparin-containing site was actually involved in the activation of neurotoxic microglia, next the levels of glycosaminoglycans (GAGs) in hippocampal cultures was reduced by enzymatic degradation or by blockade of synthesis. Removal of the heparin sulfate from microglial surfaces by heparinase caused a small reduction in neurotoxicity during the 72 hour neuron survival assay (FIG. 15D), while heparinase treatment plus a biosynthetic blockade of GAGS, including heparin sulfate, by 4-methylumbelliferyl-p-D-xyloside (β-D-xyloside) totally eliminated induction of neuron killing. In contrast, chondroitin sulfatase with or without β-D-xyloside showed only a small effect upon plaque activation of microglia. The examples provided herein provide evidence for protein-associated heparin sulfate participation in plaque activation of microglia through the HHQK domain of Aβ. It is striking that residues 12 to 17 of Aβ has been previously identified as a GAG binding site and that several laboratories have found GAGs to alter Aβ accessibility to cell metabolism. The observations reported here add another role for GAGs, implicating a membrane-associated heparin sulfate the immune activation of AD brain.

Figure 16A:
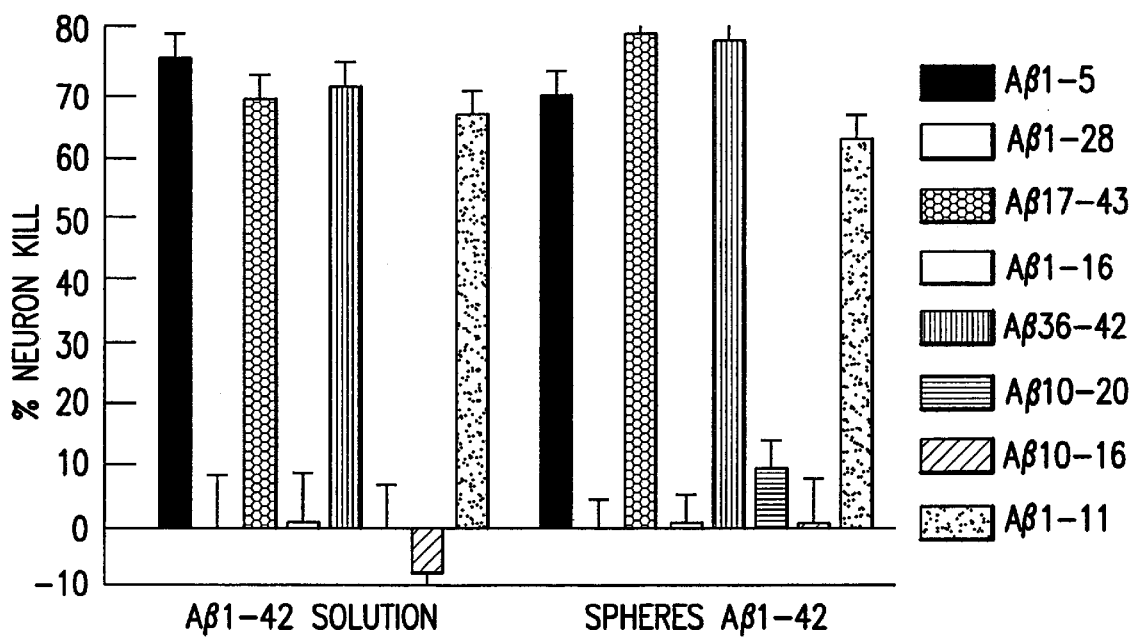
FIGS. 16A–C displays neurotoxic microglia blocked by Aβ peptides.
Figure 16B:
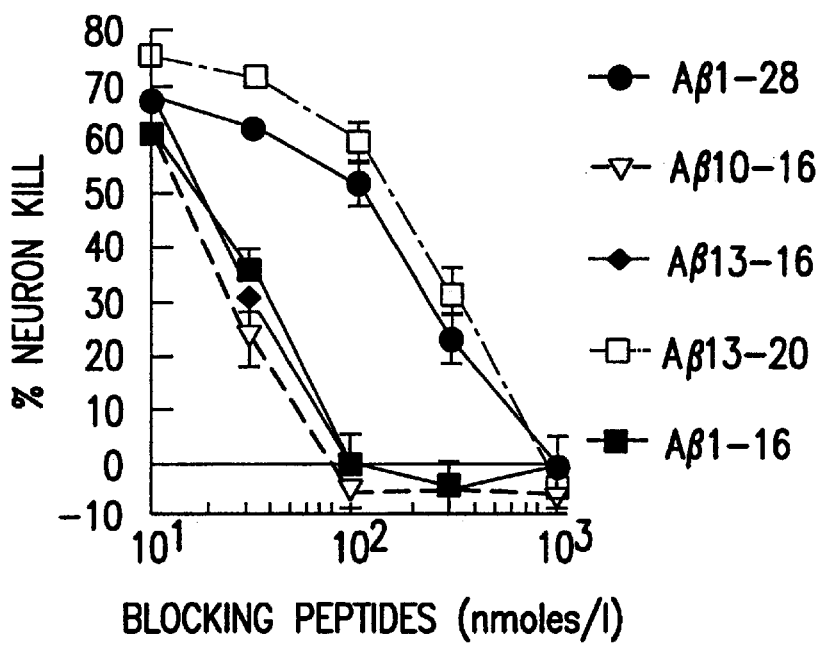
Figure 16C:
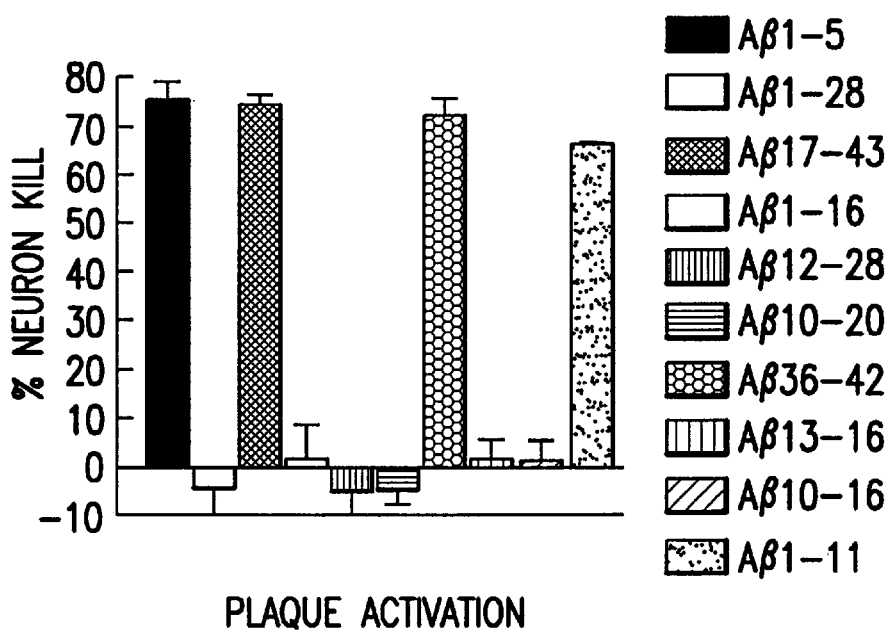

Peptides which contain the HHQK domain block Aβ1–42 adherence to microglia and, thus, might also prevent Aβ1–42 induction of neurotoxic glia. To test this possibility, various peptides (each at 10 1moles/liter) were added together with human Aβ1–42 (1 μmole/liter) to neuron cultures containing microglia. Only peptides with residues 13 to 16, namely Aβ1–28, 1–16, 10–20, 10–16, and Aβ13–16 blocked neurotoxin production while peptides Aβ1–5, 1–11, 17–43, and 36–42 did not (FIG. 16A, FIG. 17). Similar protective effects were found when using Spheres Aβ1–42 as the inducer signal. Dose response curves (FIG. 16B) showed two distinct patterns with the more potent blocking peptides (Aβ1–16, 10–16, and 13–16; ED$_{50}$ about 30 nmoles/1) restricted to the hydrophilic region of Aβ; the less potent blockers (Aβ13–20 and 1–28; ED$_{50}$ of 250 nmoles/1) included more hydrophobic regions of Aβ thought to be less accessible in the fibrillar aggregates. In contrast to Aβ1–40 or Aβ1–42, none of the blocking peptides elicited neuron killing (FIG. 14C). Since peptides Aβ1–16, 13–20, 10–16, and 13–16 also blocked plaque-induced toxicity in vitro (FIG. 16C), residues 13 to 16 of Aβ are essential not only for induction of neurotoxic microglia in culture but also for plaque activation of microglia in situ. Although the N-terminal domain of Aβ alone is responsible for amyloid binding to microglia, the C-terminal portion of Aβ must be present to activate neurotoxic pathways.

Specific Domains of β-Amyloid from Alzheimer Plaque Elicit Neuron Killing in Human Microglia Isolation of Microglia Rat microglia were isolated from newborn animals using the method of Giulian and Baker (1986) with recovery of about 0.5×106 ameboid microglia per brain with >99% purity. Criteria used to identify mononuclear phagocytes included the presence of scavenger receptors as shown by binding a fluorescent probe (acetylated low density lipoprotein labeled with 1,1'-dioctadecyl-1,3,3,3',3-tetramethyl-indo-carbocyanine [DiI-ac-LDL]), the presence of CR3 complement receptor (labeling with OX-42 antibody), characteristic spine bearing cell surface morphology seen by scanning electron microscopy, and the ability to engulf fluorescent polystyrene microspheres (1 micron, Covaspheres Particles). Hunan microglia were isolated from 50 to 100 g of normal adult cortical gray matter within a 6 hour post-mortem interval as described in accordance with the procedure set forth by Giulian et al., 1995b. Cells of a high degree of purity (>98%, about 0.5×10$^6$ cells per gram wet weight of tissue) were obtained, that were active phagocytes, and that show the presence of CD4, spine bearing surface morphology, scavenger receptors, and the class II marker HLA-DR.

Isolation, Purification, and Characterization of Plaque Proteins

AD brains were obtained from patients with both clinical history and pathologic features to meet diagnostic criteria of CERAD as defined by Mirra and Heyman, 1993. Amyloid proteins were isolated from AD cerebral cortex laden with neuritic and core plaques using discontinuous sucrose gradients of 1.2 M, 1.3 M, 1.4 M, 1.7 M, and 2.0 M. Amyloid cores were recovered from the 1.4/1.7 M sucrose interface as discrete, dense particles (15 to 25 micron diameters) and found to be thioflavine S(+) and 6E10 anti-amyloid antibody (+) (from Institute of Basic Research, Staten Island, N.Y.). These purified cores were solubilized in 80% formic acid, fractionated by Superose 12 FPLC and dialyzed (1000 dalton cutoff) against 20 mM ammonium bicarbonate containing 0.7% zwitterion betaine in accordance with the procedures of Roher et al., 1993a. The protein content of each fraction prior to dialysis was determined by amino acid analysis (Roher et al., 1993a) and morphology was examined by transition electron microscopy (TEM) in accordance with the techniques of Roher et al., 1988. The resulting five fractions obtained from pooled brain samples were highly reproducible both in content and quantity as described by Roher et al., 1988, 1993a,b. Estimates of Aβ1–40 and Aβ1–42 content in plaque fractions were determined by employing techniques described by Kuo et al. (1996). Briefly, total Aβ determinations were carried out with an ELISA method (capture monoclonal antibody 266; biotinylated reporter monoclonal antibody C6C) and measurement of Aβ1–42 by a reporter antibody 277.2 (which recognized Aβ residues 36–42) against standard curves of synthetic peptides. Estimates of Aβ1–40 were calculated as [μg total Aβ)-(μg Aβ1–42)]. The amyloid components of the plaque fractions were also characterized by tris-tricine PAGE and by western blots. The presence of (α-1-antichymotrypsin and apolipoprotein E in fractions was confirmed by immuno-staining with TEM, utilizing a colloidal gold technique as described above in accordance with the techniques set forth in Roher et al., 1993b.

Diffuse plaque proteins were isolated from postmortem brains rich in diffuse plaques (>85% diffuse deposits as viewed by thioflavine S stained sections) from patients with no clinical history of dementia. Diffuse plaque aggregates were recovered using the same methods for obtaining neuritic/core plaque fragments, but appeared as fine, thioflavine S(+), 6E10 antibody(+) threads (1 to 5 micron diameters) from the 1.4M/1.7M sucrose gradient interface. This material was then solubilized in 80% formic acid at room temperature for 30 min., centrifuged at 250,000×g for 30 min., and sequentially dialyzed (1,000 dalton cut off) against 40 mM ammonium bicarbonate, 6% betaine, pH 7.8; against 40 mM ammonium bicarbonate, 2% betaine, pH 7.8; and against 20 mM ammonium bicarbonate, 0.7% betaine, pH 7.8. Protein content prior to dialysis was estimated by measuring total amine content using the fluorescamine assay upon acid hydrolyzates (6 N HCl; 24 hours; 105° C.). Solubilized proteins from diffuse or neuritic/core plaques were added to cultures at a concentration of 400 μmoles/l total amine. All synthetic peptides were purchased from California Peptide (Napa, Calif.) or Bachem (King of Prussia, Pa.).

Aβ Coupling to Beads and Cell Adherence Assays

Synthetic Aβ peptides were linked to Sepharose beads (Pharmacia) in coupling buffer (0.1M $NaHCO_3$, 0.5M NaCl, pH 8.3) containing 20% DMSO. This solution was combined with an appropriate volume of CNBr-activated Sepharose 4B (10 mg protein per ml of bead; Pharmacia protocol) and mixed overnight on a platform mixer at room temperature. Remaining active groups on the beads were blocked by 1.0 M glycine and excess uncoupled peptides removed from this bead-peptide complex by washing with three cycles of alternating pH (0.1 M acetate buffer, pH 4.0, followed by 0.1 M Tris-HCl buffer, pH 8.0, each buffer containing 0.5 M NaCl). Coupled beads ($10^4$ per ml) were placed in 35 mm culture dishes covered with 250,000 adhering microglia at 37° C. in 1.5 ml N2 medium in accordance with the procedure of Giulian et al., 1995a. The numbers of microglia which S detached from the plate and bound to coupled beads were determined at the end of a 6 hour incubation period by inverted phase microscopy with 100 beads scored from each of three sister cultures. Glycine and bovine serum albumin (BSA) coupled beads were used as controls.

Fluoresbrite carboxylate microspheres (YG 1.0 μm, Polysciences; 0.5 ml of a 2.5% suspension) were washed twice in 0.1 M carbonate buffer (pH 9.6) and three times in 0.02 M sodium phosphate (pH 4.5). Carbodiimide was then added dropwise to a final concentration of 1% and the suspension mixed for 4 hours at room temperature. Following 3 more washes in 0.02M sodium phosphate, the pellet was resuspended in 1.2 ml of 0.2 M borate buffer (pH 8.5) and 300 μg Aβ (or control peptide) and 5% DMSO added. After overnight mixing at room temperature, the microspheres were blocked by 1 M glycine (pH 8.0) for 30 minutes and washed in 10 mg/ml BSA in phosphate buffer.

Neuron Cultures and Toxicity Assays: Establishing Cultures to Study Microglia-Neuron Interactions Cultured neurons prepared from rat hippocampus were used to assay for neurotoxins in accordance with the methods of Giulian et al., 1995a. Briefly, hippocampal cells obtained from embryonic stage 18 rat fetuses were dispersed mechanically in the presence of 0.125% trypsin and plated onto poly-L-lysine coated glass coverslips in 24 well plates at 250,000 cells per well (resulting in adhering cell densities of about 1250 cells per $mm^2$) in chemically-defined N2 culture media containing 5% fetal bovine serum. Gradual reduction of serum began on day 10 in vitro with daily 1:1 volume replacements with chemically-defined media, until a final concentration of 0.6% serum was achieved. Mature cultures consisted of process-bearing neurons (15% to 20% of total cell population) atop a bed of astroglia (>75%) mixed with microglia (from 3% to 8%; see FIG. 18). In order to eliminate microglia, cultures were exposed to saporin (sap; a ribosome-inactivating protein; Davis and Wiley, 1989) coupled to acetylated LDL (ac-LDL) at a concentration of 10 μg/ml for 12 hours. Saporin-ac-LDL selectively bound to scavenger receptors and reduced microglial numbers to <0.1% of the total population, but had no effect on numbers or viability of either neurons or astroglia (FIG. 18). Cultures depleted of microglia were then exposed to test substances in the presence or absence of exogenous microglia (100,000 cells per culture). Typically, the microglia:neuron ratio at the time of assay was about 3:1 and the astroglia:neuron ratio about 6:1. Controls included cultures without saporin-treatment, cultures without test substances, and cultures with test substances but lacking microglia.

On day 14 of culture, immediately following saporin treatment, test substances were added to the hippocampal cultures. Synthetic peptides were supplied as 1 mM stock solutions in 0.1 M phosphate buffered saline, pH 7.2, stored for at least 1 week at 4° C. before use. After 72 hours incubation, the cultures were fixed in 4% paraformaldehyde at room temperature for 18 hours and immuno-stained by overnight incubation with a mixture of anti-neurofilament antibodies (NF; SMI-311, 1:600; Stemberger Monoclonals, Inc.) plus anti-MAP-2 (Boehringer Mannheim, 184959; 1:600) at 4° C. in the presence of 2% horse serum and 0.3% triton X-100 to delineate both neuronal cell bodies and neurites. Astroglia were visualized using sheep anti-glial fibrillary acidic protein (GFAP, Sigma) as described by Giulian et al., 1989. Finally, to label all cell nuclei, the coverslips were exposed to 0.01% bisbenzimide (Hoechst 33258; Sigma) in PBS, pH 6.9, and rinsed in distilled water and mounted in glycerin. Immuno-labeled cells per field and nuclei per field were scored at 200× magnification using fluorescence microscopy. Data were expressed as % mean survival expressed in terms of parallel untreated control cultures after scoring at least 20 randomly selected fields for each of 3 coverslips.

Neuron free cultures were prepared from postnatal day 7 rat optic nerve. After 3 days in N2 culture media supplemented with 5% fetal bovine serum, cells were maintained an additional 4 days in serum free N2 medium. Cultures were then fixed and immunostained for neuronal and astroglia markers as described for hippocampal cells. Additionally, oligodendroglia containing galactocerebroside were immunostained with the monoclonal antibody 01 in accordance with the methods of Sommer and Schachner, 1981; Bansal et al., 1989; provided by Pamela Knapp, University of Kentucky, and prepared in accordance with standard methods of preparing monoclonal antibodies, such as that of Kohler & Milstein, 1975). Immuno-staining of neuron specific enolase was carried out in a 1:2000 dilution of rabbit anti-rat polyclonal antibody (Polysciences, Inc.) overnight at 4° C., after rinsing in 50 mM glycine, 0.3% triton X-100, and 10% horse serum.

Ciliary neurons from embryonic day 9 chick embryos were plated onto poly-L-lysine coated coverslips in 24 well plates at 2 ganglia per well in N2 media (diluted to 90%) and supplemented with 30 mM KCl plus 0.6% horse serum (modified from Giulian et al., 1993b). Cultures consisted of about 50% neurofilament(+) neurons mixed with Schwann cells and were free of mononuclear phagocytes and astroglia. Ciliary neurons were sensitive to the toxic effects of NMDA and quinolinic acid (Giulian et al., 1993a,b). Neurotoxic activity was measured after 48 hour as described in detail previously (Giulian et al., 1993a). The percent neuron kill score was calculated as [1-(neurons per field in treated group/neurons per field in the untreated control group))× 100%. Data were expressed as mean values ± standard error, with each value obtained from 18 fields per coverslip using at least 6 coverslips per group.

Biochemical Studies of Toxic Agents

Purification of neuron killing activity from culture media conditioned by activated microglia was performed in accordance with the methods of Giulian et al., 1995a and ultrafiltrated through a YM-30 membrane followed by a YM-1 membrane. The ultrafiltrates were then washed with equal volumes of ethyl acetate under acidic conditions (pH 4.0) and then extracted into ethyl acetate under alkaline conditions (pH 10.5). All neurotoxic activity was recovered into this basic organic phase. Material was re-extracted into an acidic aqueous phase (pH 2.0), dried under vacuum, flushed with nitrogen gas, and subjected to acid hydrolysis (in 6 N HCl for 24 hours at 105° C.). Hydrolysates were then extracted into basic ethyl acetate and eluted twice from C18 Rβ-HPLC (3.9×150 mm Nova-Pak, Waters) with a 0% to 20% acetonitrile gradient developed over 35 minutes (solvent A, 0.1% trifluoroacetic acid in $dH_2O$; solvent B, 0.1% trifluoroacetic acid in $dH_2O$:acetonitrile 5:95, v/v). Purification of neurotoxic activity from AD neocortex involved an aqueous extract (10 vols sterile distilled water per tissue weight) from 1 kg of minced gray matter of frozen human brain which was subjected to an identical fractionation as described above, using ultrafiltration, organic extraction, acid hydrolysis, and RP-HPLC in accordance with the methods of Giulian et al., 1995a. Phenolyic and arnine contents were used to estimate concentrations of neurotoxin found within highly purified HPLC fractions. Assigning a $Uv_{max}$ of 265 nm (0.1% trifluoroacetic acid in 14% acetonitrile in $dH_2O$), peaks of activity eluted from C18-HPLC were compared to a standard curve of tyramine eluted under identical conditions measured with a multiple wavelength detector (Rainin Dynamax UV-M). Amine content was determined by the fluorescamine method using tyramine as a standard. These detection methods gave similar values for a given toxin preparation; the estimates of toxin concentration assumed one amine and one phenolic ring per molecule as described by Giulian et al., 1995a.

Acid-catalyzed esterification of neurotoxin was carried out with 3 N HCl in n-butanol (Regis Chemical Co., Morton Grove, Ill.) for 60 min at 80° C., short acetylation in acetic anhydride in methanol (1:3 vol:vol; Sigma) for 1 min at 25° C. and the reaction was terminated by addition of excess glycine at room temperature. Neurotoxin was also modified by excess pentafluoropropionic anhydride (PFPa.; Fluka Chemie AG, Switzerland) at 60° C. for 60 min, with 100 units/ml of plasma amine oxidase (amine:oxygenoxidoreductase; 1.4.3.6; Worthington Biochemical Corp., Freehold, N.J.) at 25° C. in 1 ml of 10 mM phosphate buffered saline (pH 7.0) for 4 hours or with 390 units of polyphenol oxidase (monophenol, dihydroxypheny-lalanine:oxgenoxidoreductase; 1.14.18.1, Worthington) at 25 ° C. in 2 ml of 10 mM phosphate buffered saline (pH 7.0) for hours. In all cases, enzymatic reactions were terminated by boiling for 15 min. Inactivated-enzyme controls were prepared by boiling prior to incubation with neurotoxins.

Nitrites and nitrates, stable byproducts of nitric oxide synthetase (NOS) served as markers for nitric oxide (NO) synthesis (Ignarro, 1990). Nitrite/nitrate concentrations in media conditioned by isolated human microglia ($10^6$ cells per ml; for 24 to 72 hours incubated in the presence of neuritic/core plaques or Aβ peptides) were measured by the Griess method set forth by Beckman et al., 1990 against a standard curve ranging from 0.1 to 50.0 μM nitrate.

Establishing Cultures to Study Microglia-Neuron Interactions

Figure 18A:
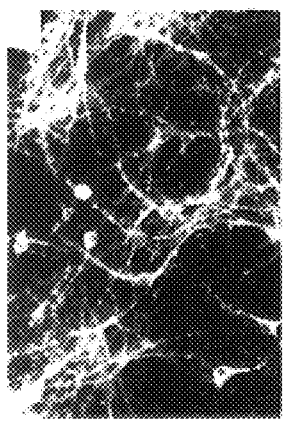
FIGS. 18A–G show selective elimination of microglia from mixed hippocampal cultures. Control cultures (FIGS. 18A, 18C, 18E) show complex neuronal networks revealed by MAP-2/neurofilament immunostaining (FIG. 18A), the presence of DiI-ac-LDL(+) microglia (FIG. 18B), and near confluent feeder layer of GFAP (+) astrocytes (FIG. 18C). After treatment of cultures with saporin coupled to acetylated LDL (FIGS. 18B, 18D, 18F), there was an elimination of microglia (FIG. 18D) without effect on survival of either neurons (FIG. 18B) or astroglia (FIG. 18F). Bar=25 μm.
Figure 18B:
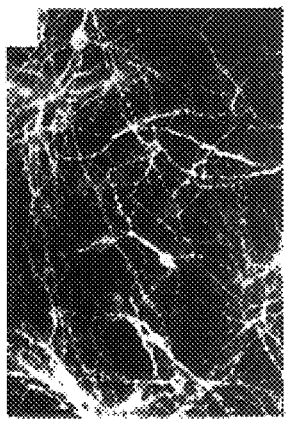
Figure 18C:
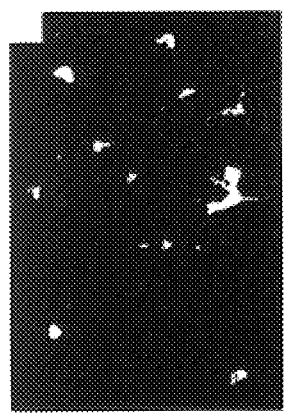
Figure 18D:
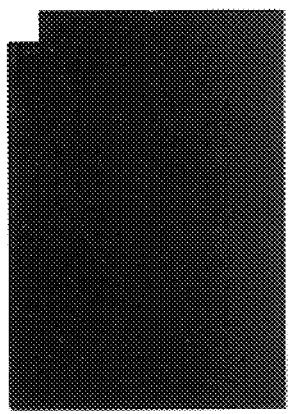
Figure 18E:
Figure 18F:
Figure 18G:
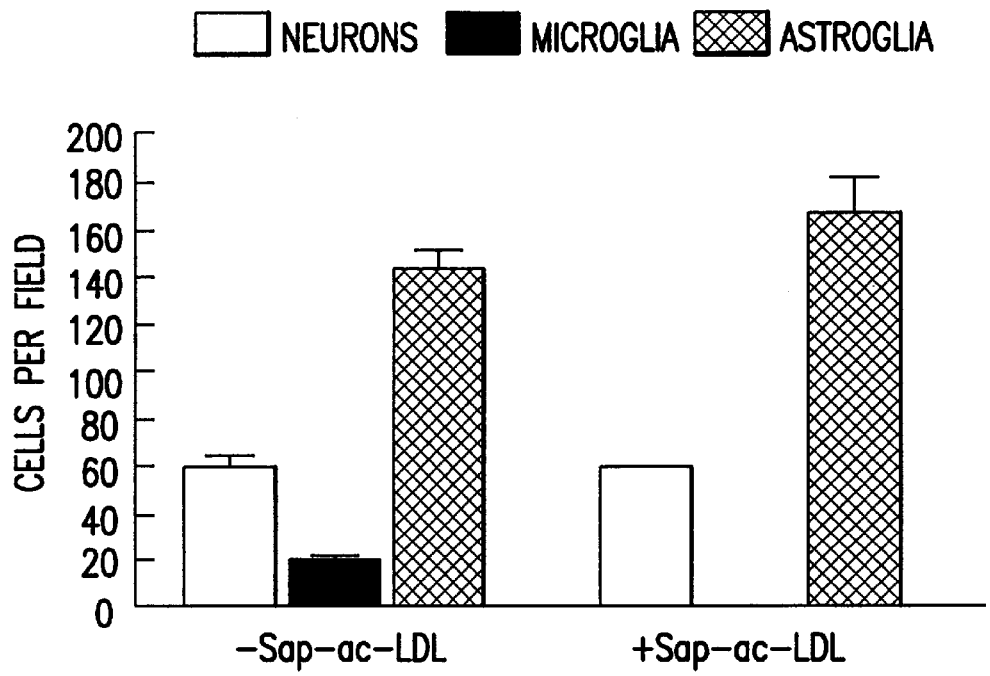

Reactive microglia in AD brain cluster around neuritic and core plaques, but do not interact with diffuse ones (Perlmutter et al., 1992; Giulian et al., 1995a). Recent studies have indicted that such reactive microglia are a source of neurotoxic factors and may injure neurons in a variety of disorders (Giulian, 1992; Giulian et al., 1995a). Study of such putative glia-neuron interactions requires suitable in vitro methods. Current models of AD pathogenesis have relied heavily upon brain cell cultures, particularly those prepared from dissociated embryonic rat hippocampus. In order to examine microglia-neuron interactions, it was necessary to develop long term in vitro systems that both contained robust hippocampal neurons and allowed control of microglial populations. Dissociated E18 hippocampal cells grew well at >1,000 cells per $mm^2$ in N2 media supplemented with 5% fetal bovine serum. To more closely approach a chemically defined media for study of cellular interactions, the serum supplement was reduced to a minimal level by serial dilution. Although neurons anchored themselves atop a feeder layer of astroglia within 5 days, rapid reductions in serum concentrations caused astroglia to form thin processes which, in turn, dislodged adhering neurons. To preserve the neuron-astroglia relationships, sera levels were reduced gradually beginning on day 10 in vitro by partial media changes. Under such conditions, hippocampal populations contained about, 15% neurofilament(+), MAβ2(+) neurons (FIG. 18A), about 5% scavenger receptor (+) microglia (FIG. 18C), and >75% GFAβ(+) astroglia (FIG. 18E). The microglia present in these cultures have been previously shown to be a significant source of cytokines and cytotoxins (Giulian et al., 1989; Giulian et al., 1994; Giulian et al., 1995a). In order to eliminate microglia from these hippocampal preparations, saporin, a ribosomal inactivating protein, was coupled to ac-LDL. As shown in FIG. 18D, saporin-ac-LDL (10 μ/ml for 12 hours) essentially destroyed all scavenger receptor(+) microglia while sparing neurons (FIG. 18B) and astroglia (FIG. 18F). Monitoring each of the cell populations (FIG. 18G) confirm that this treatment brought about a selective elimination of microglia in embryonic hippocampal cultures.

Thus, saporin-ac-LDL provided a selective agent to deplete microglia; alternatively, the addition of isolated microglia (>99/homogeneity) to the neuron/astroglia cultures offered a means to selectively reestablish this glial population. By controlling mononuclear phagocyte populations, it was possible to determine if AD plaque proteins influenced microglia-neuron interactions.

Senile Plaques and Microglial Killing of Neurons

Figure 19A:
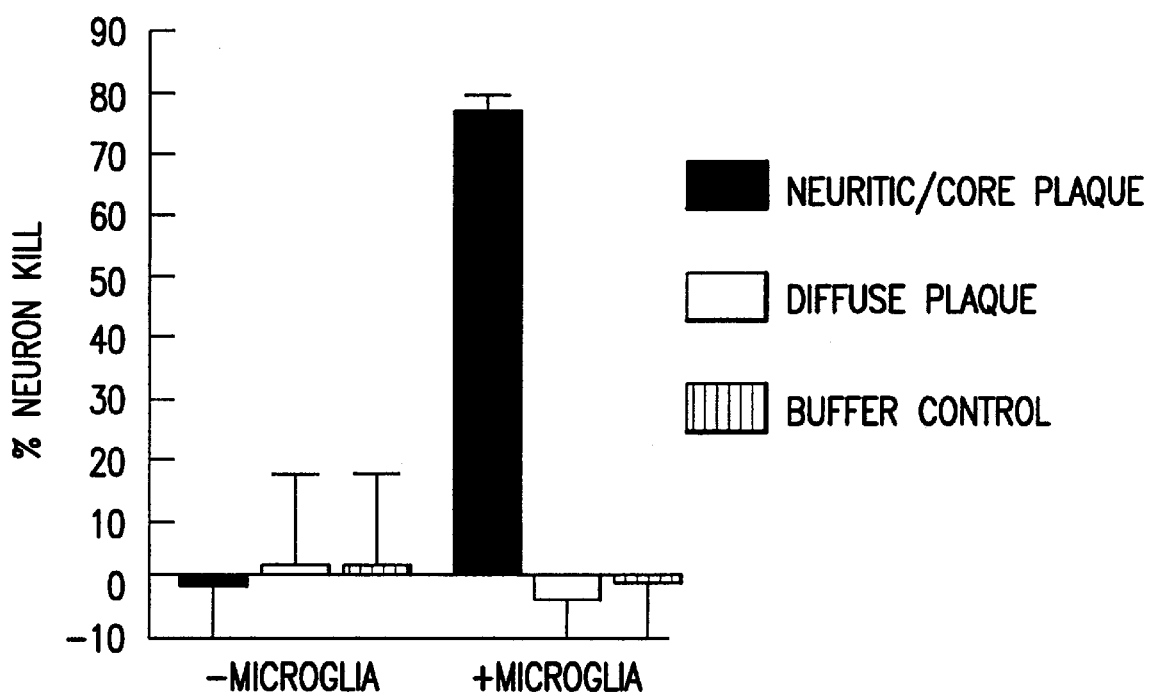
FIGS. 19A–D displays constituents of solubilized native senile plaques elicit neuron killing.
Figure 19B:
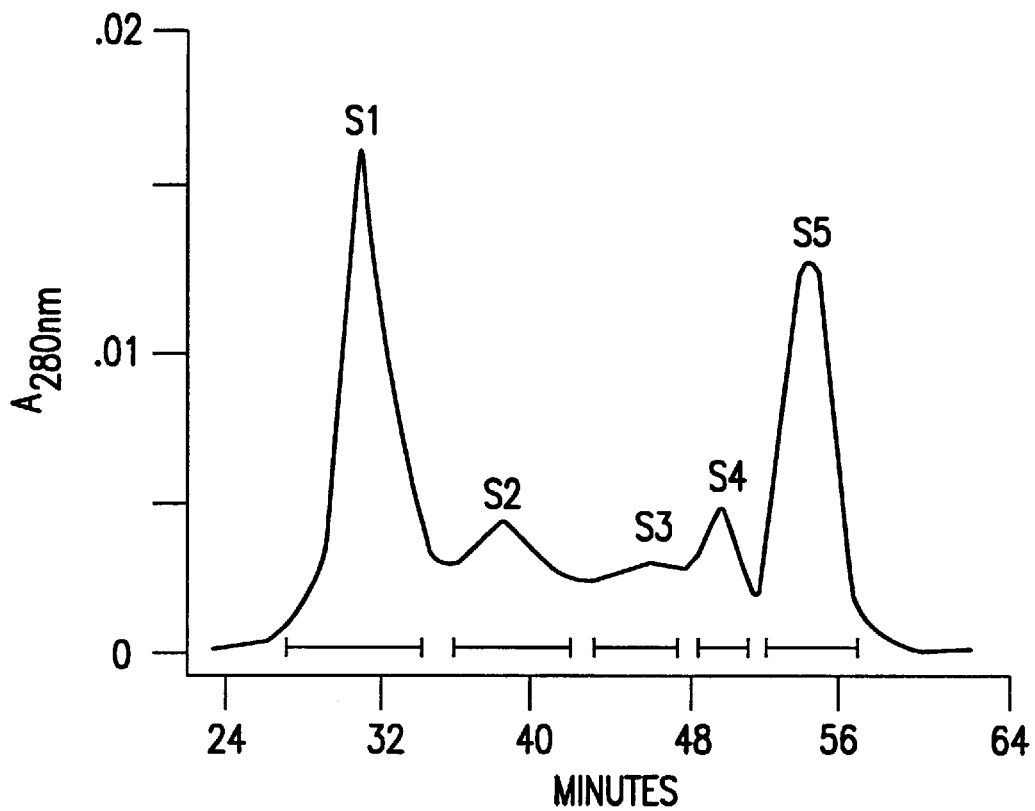
Figure 19C:
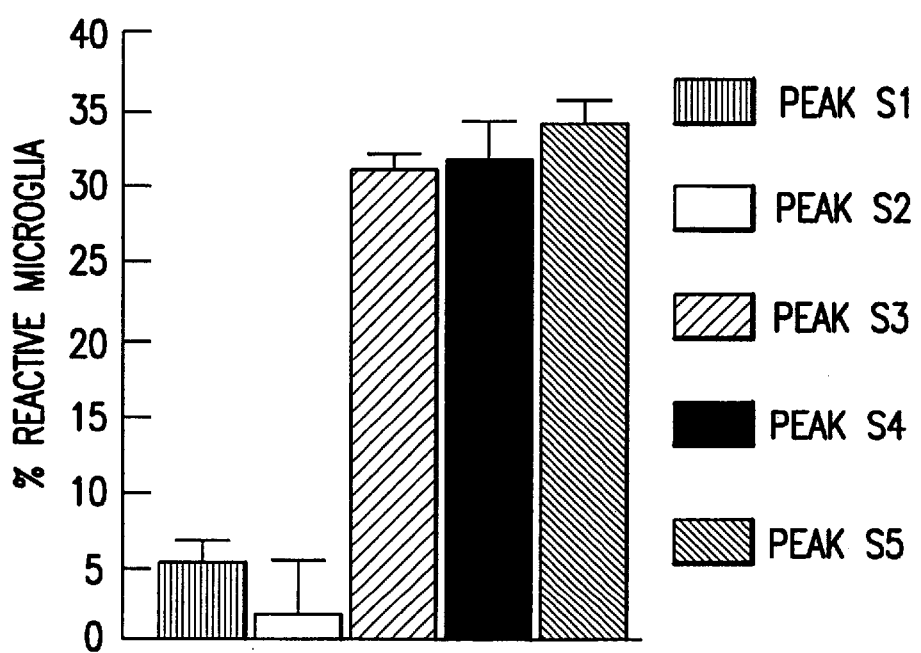
Figure 19D:
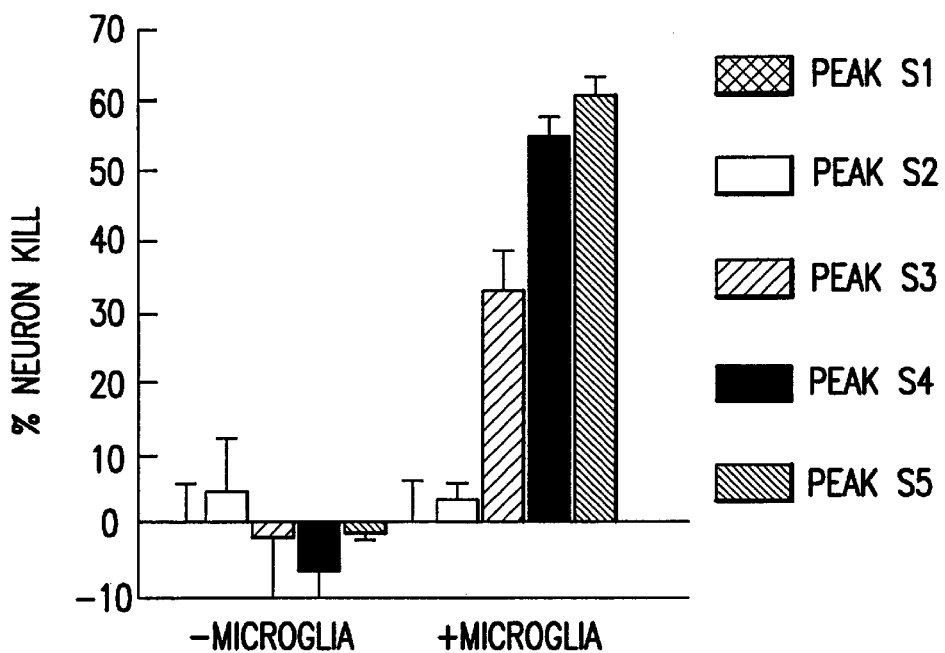
Figure 20A:
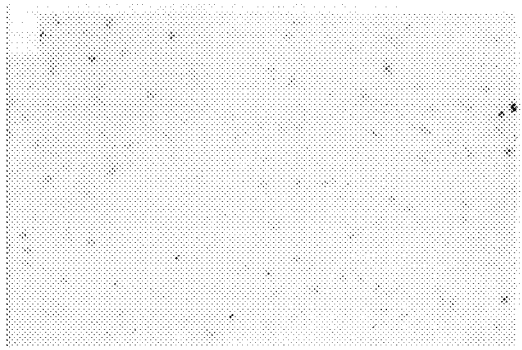
FIGS. 20A–D displays soluble fractions of native plaques induce microglial reactivity. Bright field photomicrographs of rat microglia cultures exposed to peak S1 (FIG. 20A) or peak S5 (FIG. 20B) and immuno-stained for the presence of Aβ. As shown, aggregates of Aβ are found throughout the cultures incubated with peak S5 (Bar=25 microns). Phase photomicrographs show cultured microglia as process bearing cells with spinous surfaces typical of non-reactive cells despite exposure to peak S4 (FIG. 20C). In contrast, microglia exposed to peak S5 retract processes and take on a reactive cell morphology similar to that found in AD brain (FIG. 20D; Bar=5 microns).
Figure 20B:
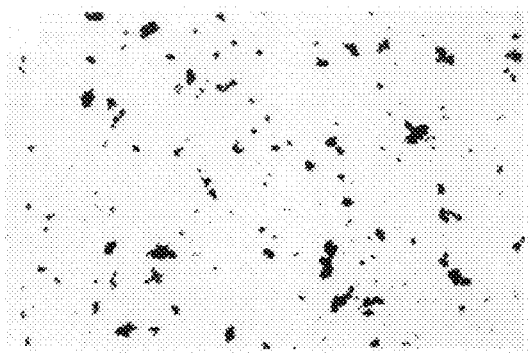
Figure 20C:
Figure 20D:
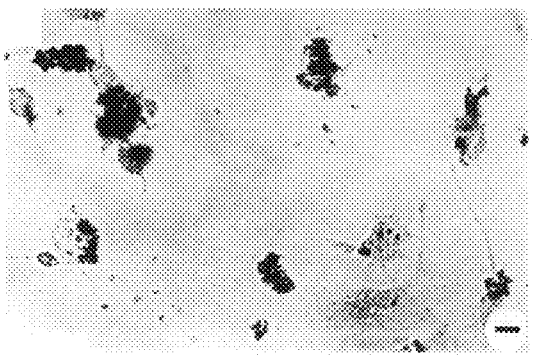

As reported earlier, cultured microglia incubated with neuritic/core plaque fragments released neuron killing factors (Giulian et al., 1995a). To investigate the specificity of this plaque-microglia interaction, neuritic/core plaques from AD brains and diffuse plaques from normal, aged brains were isolated, solubilized, and applied to cultured hippocampal neurons in the presence or absence of microglia. As shown in FIG. 19A, solubilized neuritic/core plaque proteins stimulated microglial release of neurotoxins, while the solubilized constituents of diffuse plaques did not. To elucidate the signaling mechanism, solubilized neuritic/core plaque material was next fractionated into 5 major peaks by sizing chromatography (FIG. 19B) as described previously by Roher et al. (1993a,b). Dominant constituents found in these plaque fractions ]Included glycoproteins and cc-1-antichymotrypsin in peak-SI, apolipoprotein E (apoE) in S2, and significant amounts of Aβ-amyloid (predominately Aβ1–42) in peaks S3, S4, and S5, as trimers, dimers, and monomers respectively (TABLE 1). Plaque fractions S3, S4, or S5 added to microglial cultures led to dramatic retraction of cellular processes and engulfment of amyloid (FIGS. 20B and 20D), while fractions SI and S2 had little effect upon nmicroglial (FIGS. 19C, 20A, and 20C). The addition of plaque fractions S3, S4, and S5 to hippocampal cultures led to a severe loss of neurons, but only in the presence of microglia (FIG. 19D). These data suggested that plaque-derived fractions S3, S4, and S5 contained f actors capable of inducing neurotoxic microglia. As shown in TABLE 1, A$\beta$1–40 or A$\beta$1–42 peptides are common to these 3 fractions and were, therefore, likely candidates as microglial activators.

B-Amyloid Peptides and Microglial Killing of Neurons

Figure 21A:
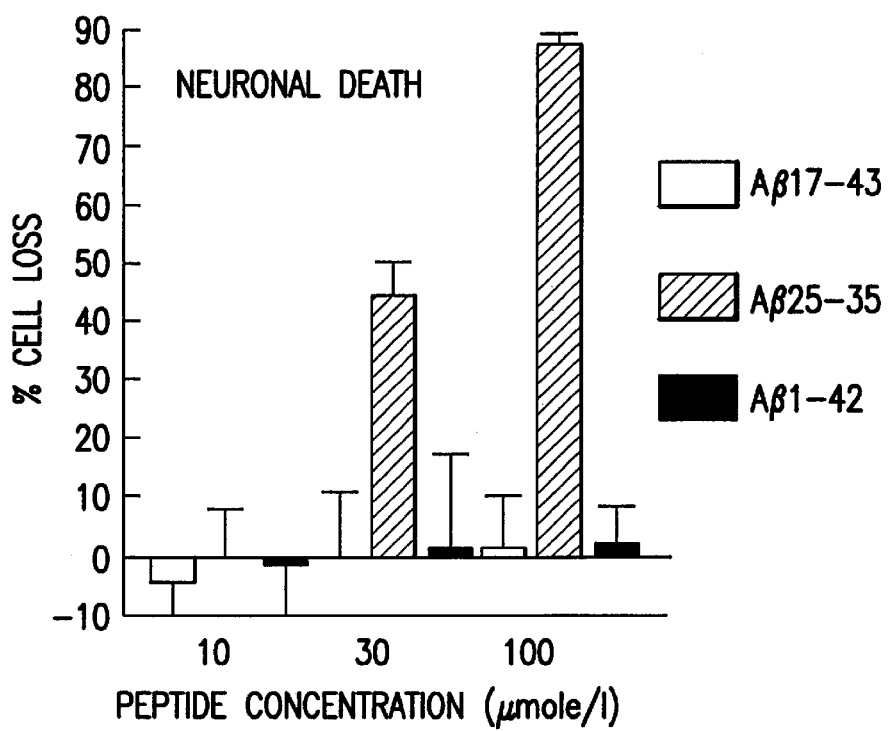
FIGS. 21A–E displays toxic actions of synthetic Aβ peptides upon neurons.
Figure 21B:
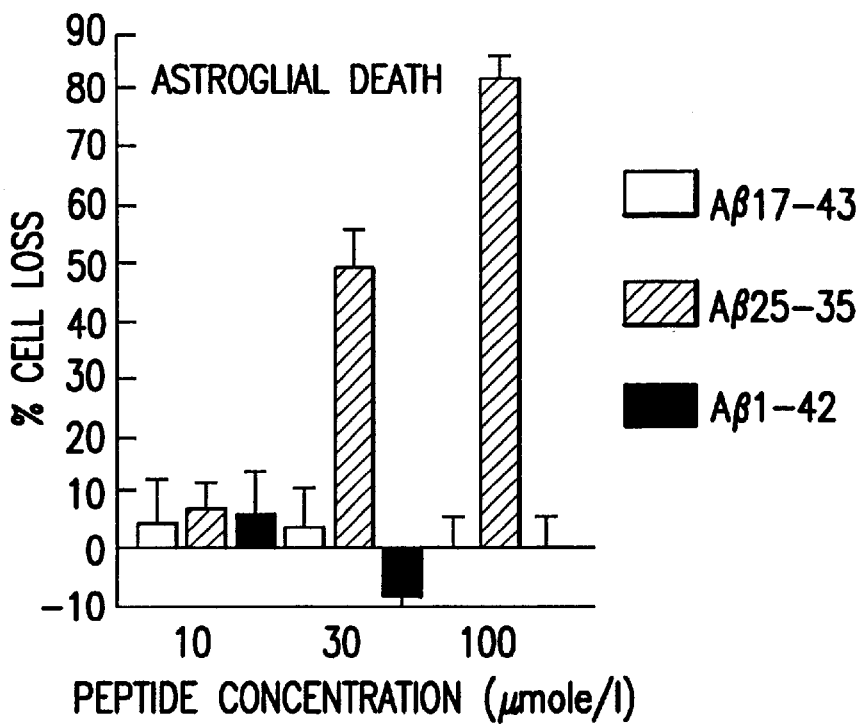
Figure 21C:
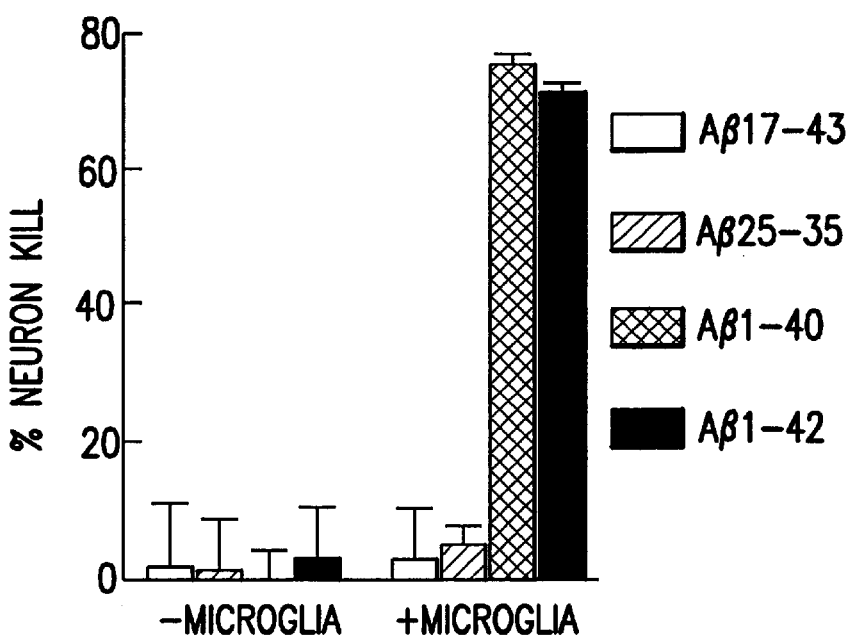
Figure 21D:
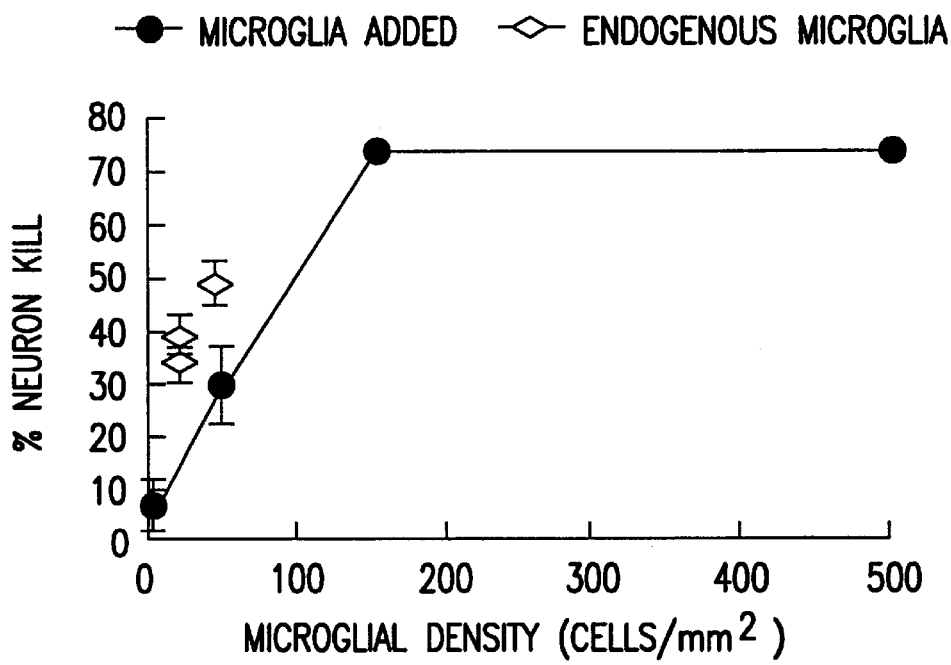

To test whether A$\beta$ alone could drive neurotoxic microglia, the actions of synthetic peptides were next examined (TABLE 2). Generally, A$\beta$ peptides applied in PM concentrations had no damaging effects upon neurons grown in microglia-free cultures (FIGS. 21A and 21C). When, however, microglia were added to this culture system and incubated with either human A$\beta$1–40 or A$\beta$1–42, there was widespread neuronal loss (FIG. 21C; FIG. 22). In the presence of 1 $\mu$mole/liter A$\beta$1–42, the microglial density required for maximum neuron killing was about 150 cells per mm$^2$ (microglia:neuron ratio of 0.8:1; FIG. 21D), although neuron killing in the presence of <50 microglia per mm$^2$ was noted. Without saporin-ac-LDL pretreatment, the endogenous microglia population normally found in these cultures ranged from 40 to 80 cells per mm$^2$. The levels of neuron killing in preparations containing endogenous microglia (incubated with 1 $\mu$mole/liter A$\beta$1–42) were above values predicted by cell density curves constructed from the addition of exogenous glia (FIG. 21D), indicating that native microglia seeded with the original E18 cultures were particularly efficient as neuron killing cells. Clearly, depletion of microglia from mixed neuron-glia cultures was necessary to demonstrate-killing by inflammatory cells brought about by A$\beta$.

Figure 21E:
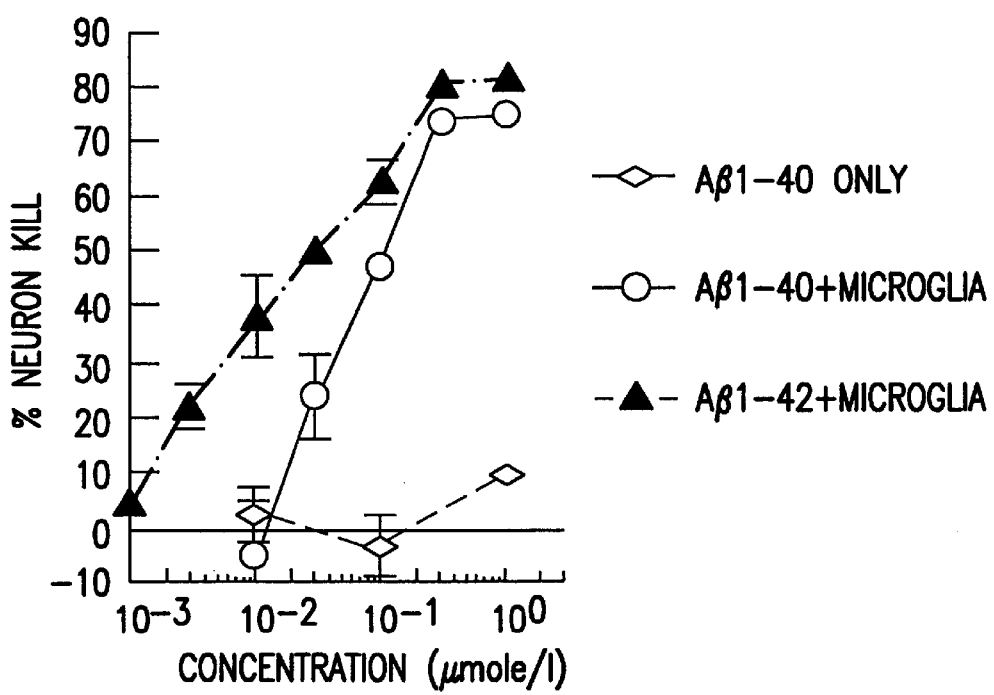

When 500 microglia per mm$^2$ were added to neuron cultures, A$\beta$1–42 and A$\beta$1–40 showed ED$_{50}$s of about 10 and 80 nmoles/1 respectively (FIG. 21E). The amount of A$\beta$1–42, therefore, found in plaque fractions S3, S4, and S5 (TABLE 1), as well as the amounts of A$\beta$1–42 estimated to exist in AD brain (in the range of ng/gm tissue; Kuo et al., 1996), would be sufficient to elicit neurotoxic glia. For the most part, small A$\beta$ peptides (A$\beta$1–16, A$\beta$1–28, A$\beta$1–43; TABLE 2) did not produce neurotoxicity in the presence or absence of microglia. An exception, however, was A$\beta$25–35 which was generally cytotoxic at high concentrations (2:30 4moles/1) with destruction of nearly 90% of both neurons and glia when given at 100 $\mu$moles/1 (FIGS. 21A and 21B). This lack of neuronal specificity for high concentrations of A$\beta$25–35 was consistent with its damaging effects noted by others on such non-neuronal cell lines as HeLa (Pollack et al., 1995) or upon primary cultures of astrocytes (Harris et al., 1995). However, since $\beta$25–35 is not a naturally occurring biological product, it is unlikely to participate in the pathology of AD (Roher et al., 1993a,b).

Figure 23A:
FIGS. 23A-E displays Aβ3 activation of microglia after coupling to microspheres. Fluorescently labeled microspheres were covalently coupled to Aβ1–42 and placed in hippocampal cultures containing rat microglia (500 cells per $mm^2$) After 72 hours, A,β1–42-spheres (FIG. 23A) were localized specifically within DiI-ac-LDL(+) microglia (FIG. 23B, co-localization noted by arrows). In contrast, Aβ17–43-microspheres (FIG. 23C) showed no consistent association with microglia (FIG. 23D; Bar =20 micron).
Figure 23B:
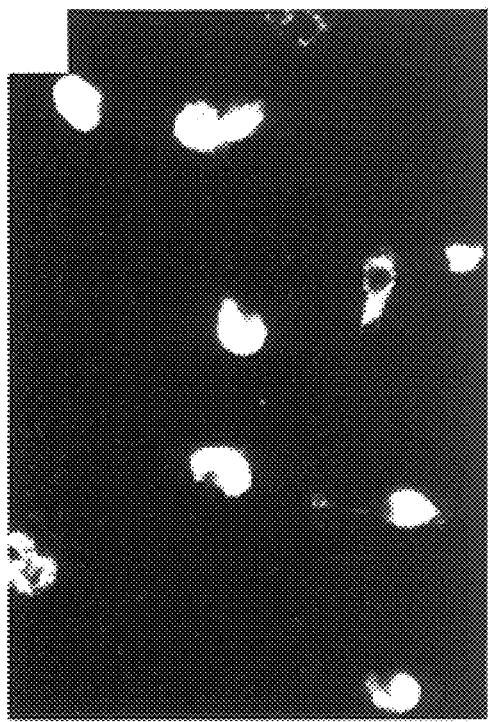
Figure 23C:
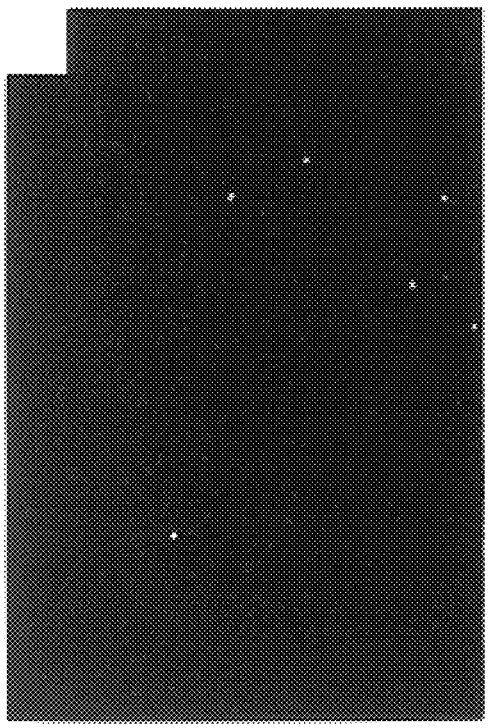
Figure 23D:
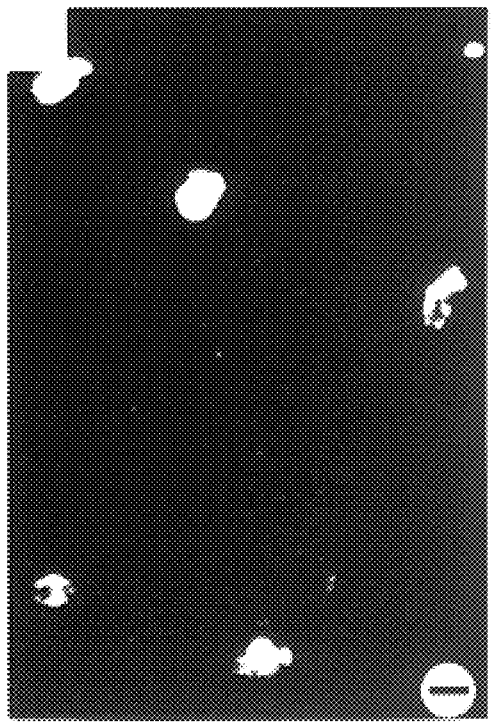
Figure 23E:
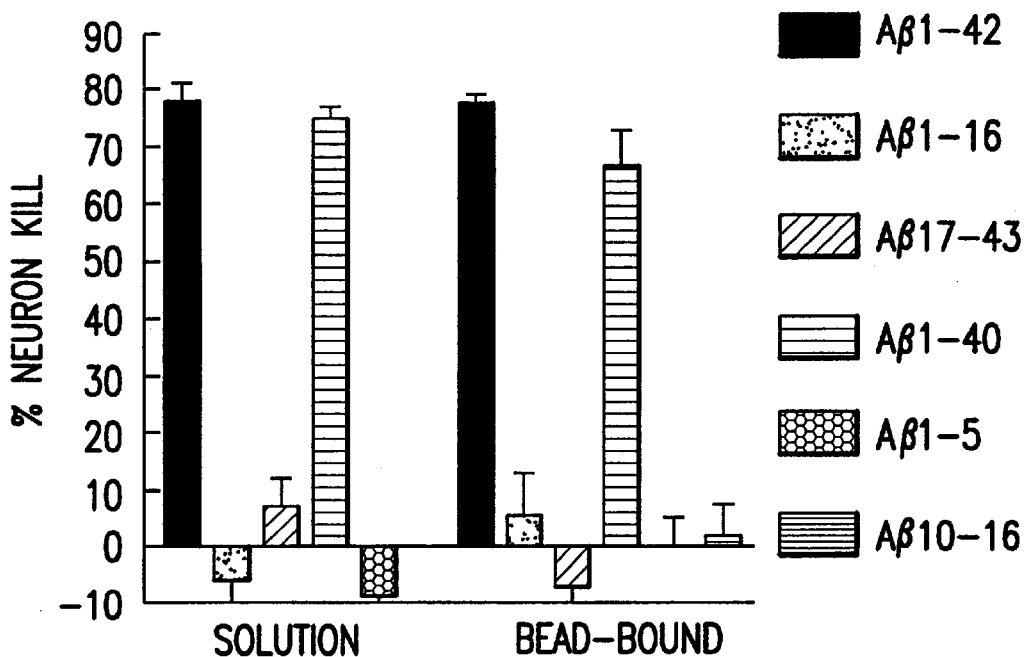

A number of reports have suggested that the neurotoxic capacity of A$\beta$ is associated with specific structural features such as aggregation or fibril formation (Pike et al., 1991, 1993). For example, Pike et al (1991) described greater neuron loss after A$\beta$1–42 was stored at 37° C. or several days to increase the appearance of aggregates in distilled water. Both fresh and "aged" A$\beta$1–42 peptides prepared as described by Pike et al. (1993) were found to be equally effective in stimulating neurotoxic microglia (75.1% +–5.8% vs. 77.5% ±2.6% neuron kill respectively). It has been suggested that fibril formation occurring with A$\beta$1–42 in solution was a critical feature for its neurotoxicity (Lorenz and Yankner, 1994; Simmons et al., 1994; Howlett et al., 1995). To determine whether conformational states such as aggregation were pertinent to microglia-dependent neuron killing, various A$\beta$ forms were covalently coupled to 1 micron fluorescent microspheres. A$\beta$1–42 coupled-microspheres were readily taken up by microglia in E18 cultures (FIGS. 23A and 23B), similar to the rapid cell recognition of neuritic/core plaque fragments (Giulian et al., 1995a) and native A$\beta$ aggregates (FIG. 20). In contrast, A$\beta$17–43 coupled microspheres were not engulfed by microglia (FIGS. 23C and 23D). Importantly, microsphere-coupled A$\beta$1–42 and A$\beta$1–40, as well as unbound forms in solution, activated neurotoxic microglia, while A$\beta$1–16 or A$\beta$17–43 were not effective when tested either in solution or linked to microspheres (FIG. 23E). These observations suggested that the primary structure of the A$\beta$1–42 peptide, and not such complex features as aggregation or $\beta$-sheet formation, was sufficient to induce neurotoxic glia.

How Potent is A$\beta$ as a Direct Neurotoxin?

Figure 24H:
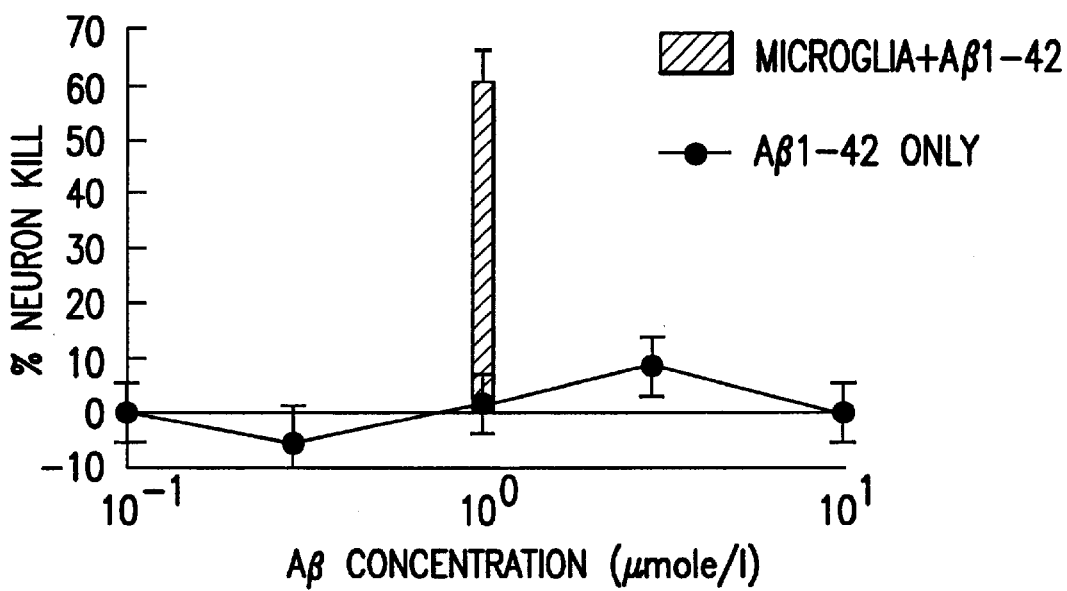
FIGS. 24A–H depicts fluorescent photomicrographs of hippocampal cultures after exposure to Aβ1–42.
Figure 24A:
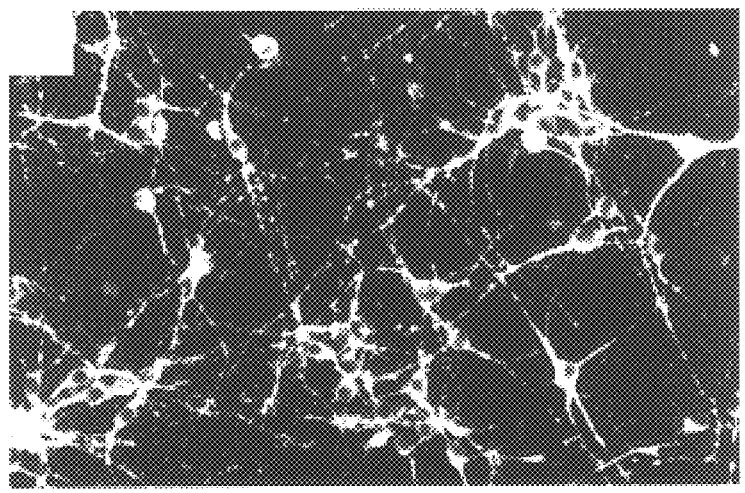
Figure 24B:
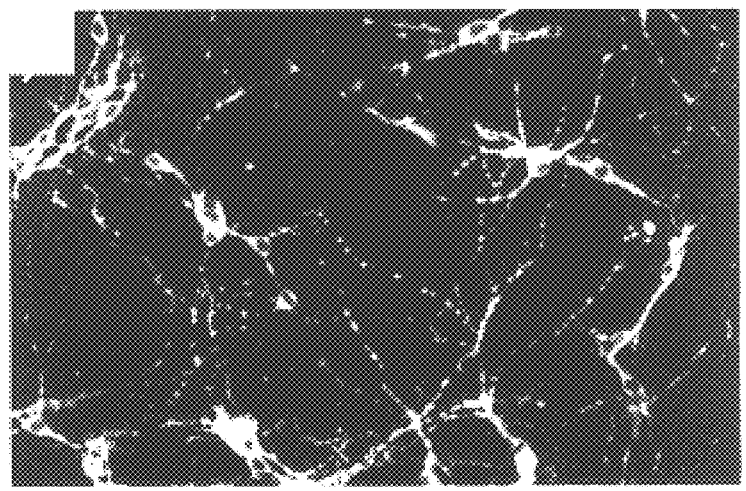
Figure 24C:
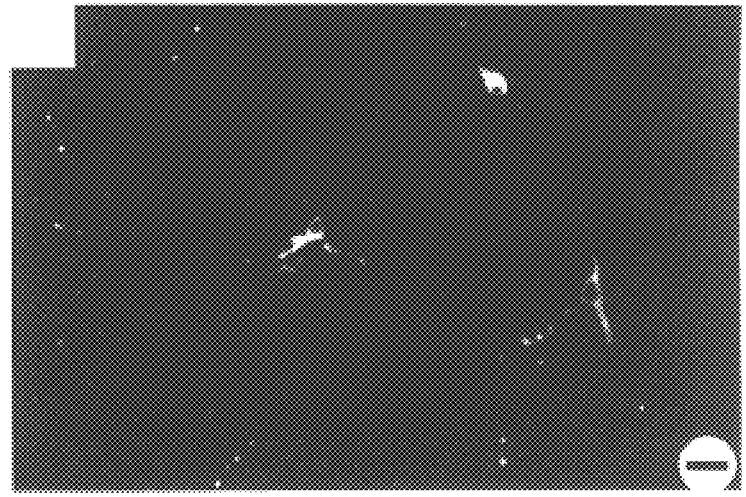

As noted above, A$\beta$1–42 did not directly kill neurons when applied at 100 $\mu$moles/liter in cultures free of microglia (FIG. 24B) while 100 $\mu$moles/liter AD in the presence of microglia brought about significant neuron loss (FIG. 24C). Because previous reports (Pike et al. 1991, 1993; Cotman et al., 1992) described direct effects of A$\beta$1–42 upon neurons in vitro, culture conditions, other than the presence of microglia, were sought which might lead to neuron killing. Since astroglia might participate in AD mechanisms of neuronal injury, whether astroglia-free cultures of ciliary ganglia (approximately 50% neurons and 50% Schwann cells) were examined for sensitivity to A$\beta$. Direct application of A$\beta$1–42 again had no apparent effect upon survival of ciliary cells, while A$\beta$1–42 stimulated microglia secreted toxin to destroy ciliary neurons (FIG. 24H). Similarly, plaque-stimulated microglia have been found to destroy ciliary neurons (Giulian et al., 1995a).

Figure 24D:
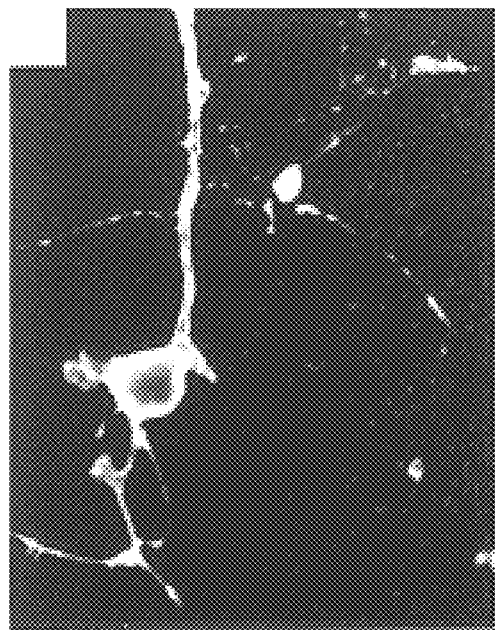
Figure 24E:
Figure 24F:
Figure 24G:
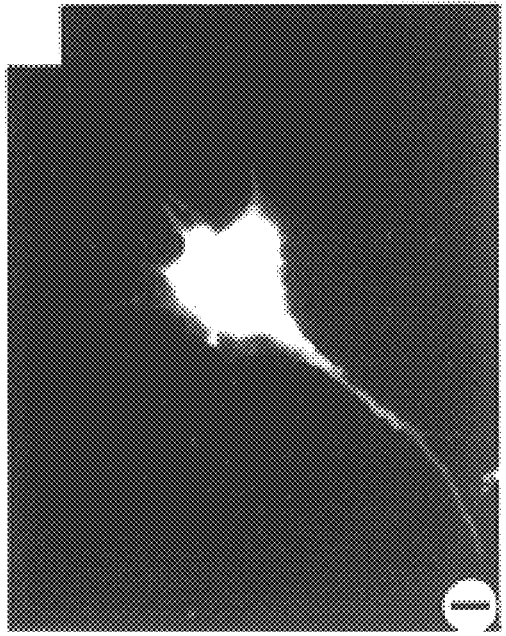

As an alternative strategy to assess the role of astroglia in A$\beta$ interactions with microglia, glia were eliminated from dissociated E18 hippocampal cells using mitotic inhibitors as described by Koh et al. (1990) and Pike et al. (1993). Such culture systems, however, did not provide a reliable assay for monitoring neuron killing, for these cell preparations were inherently unstable with neuron survival dropping to <80% within 48 hours. Moreover, the use of chemically-defined media or mitotic inhibitors did not actually eliminate non-neuronal cells [such as glial precursors, scavenger receptor(+) microglia, or GFAP(+) astroglia] but simply slowed glial differentiation and the degree of antigen expression. In addition, astrocytes grown under such marginal culture conditions take on a reactive morphology with long, thin processes similar to neurons. Despite reports by others (Whitson et al., 1989; Koh et al., 1990; Pike et al., 1991, 1993; Cotman et al., 1992), a reliable neuron count in such preparations was not obtained by phase microscopy. Introduction of fetal calf sera to poisoned cultures stimulated cells with neuron-like morphology to develop into GFA$\beta$(+) astroglia. Although NF(+) MAP2(+) neurons made up less than 20% of the hippocampal cell population, >90% of the cells were found to be neuron specific enolase(+). However, neuron-free cultures of developing optic nerve also contained >85% neuron specific enolase(+) cells, including process-bearing galactocerebroside(+) oligodendroglia (FIGS. 24D and 24E) and GFAP(+) astroglia (FIGS. 24F and 24G). Overall, healthy cultures of highly enriched hippocampal neurons could not be established using methods known to skilled artisans, nor was AD toxicity within such preparations reliably interpreted. The direct action of A$\beta$ upon primary cultures of glia-free brain neurons was not assessed.

Specific Plaque Proteins Activate Human Microglia

Figure 25A:
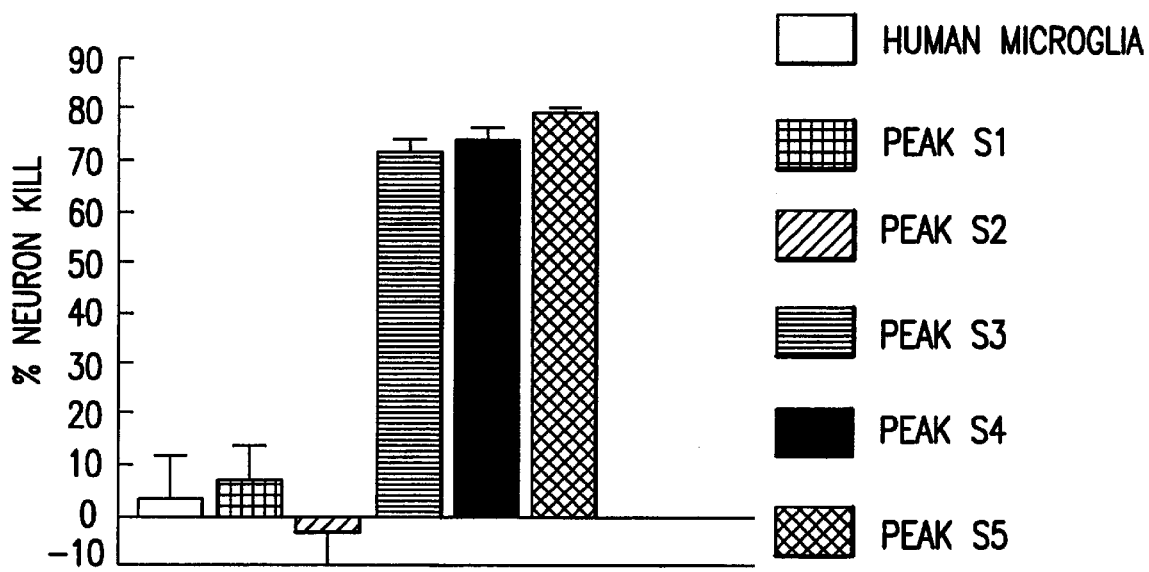
FIGS. 25A–E displays human microglia and neuron killing.
Figure 25B:
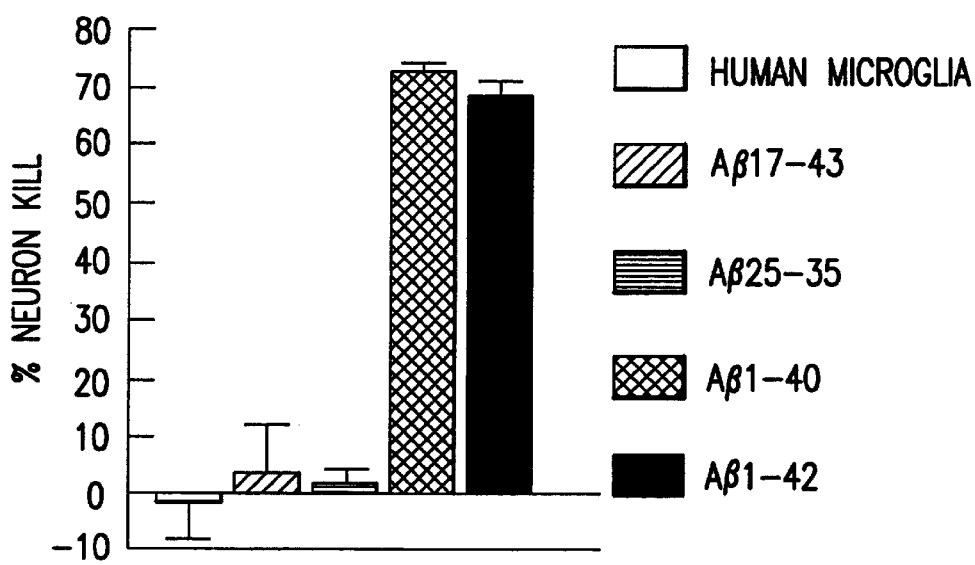
Figure 25C:
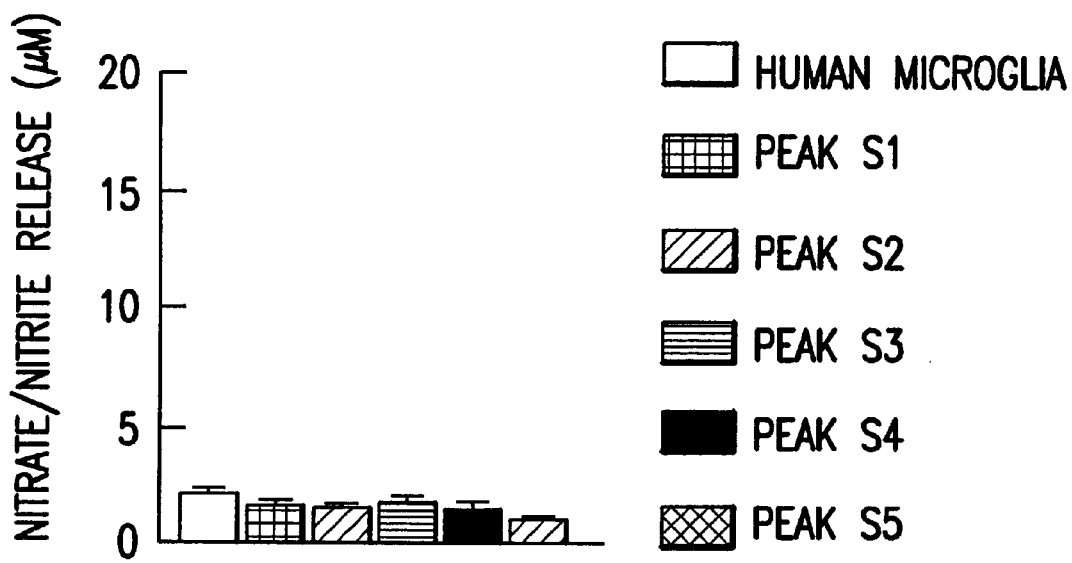
Figure 25D:
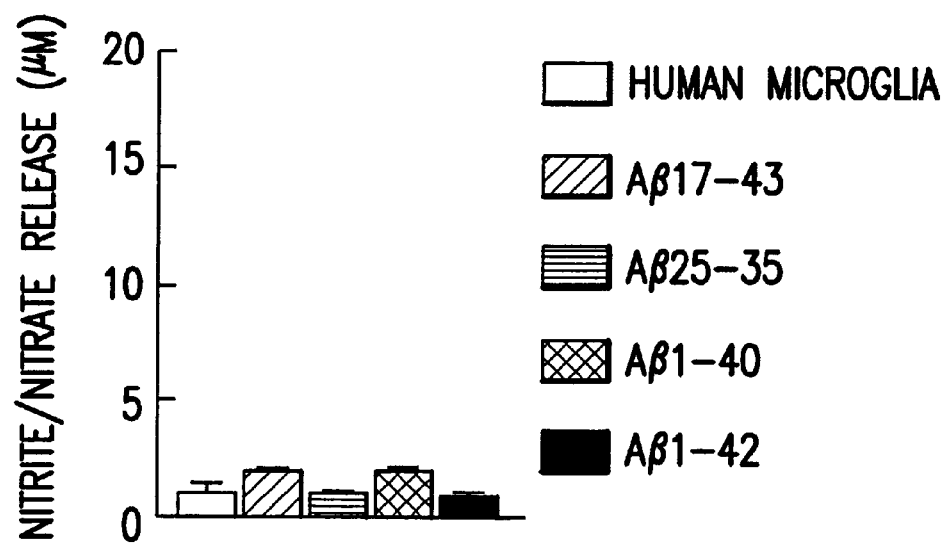
Figure 25E:
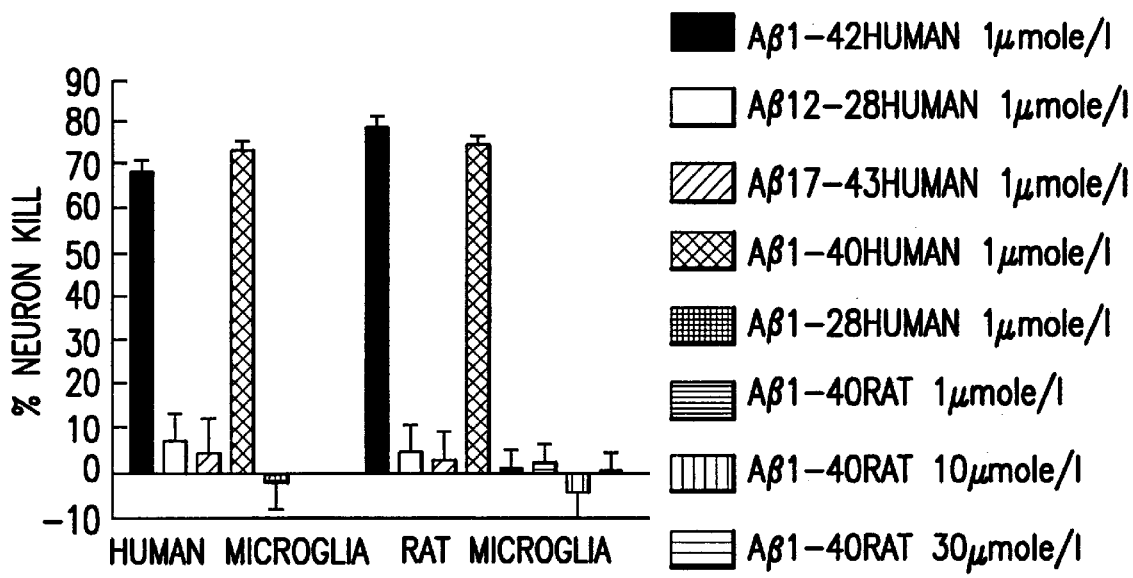

Responses of human microglia to AD, as well as to other stimulants, might differ from the responses of rodent microglia. Activated rodent macrophages, for example, are richly supplied with inducible nitric oxide synthetase (iNOS) and produce cytotoxic levels of nitric oxide (NO; Lees, 1993). In the hippocampal culture system, lipopolysacchraride (2:100 $\mu$/ml) induces rat microglial iNOS which resulted in NO-dependent killing of neurons. In this culture system, there was a dose dependent relation of nitrate/nitrite levels of the media and neuronal loss, with loss apparent at 15 $\mu$M nitrate/nitrite and above (data not shown). Human macrophages, on the other hand, are thought to contain little iNOS and produce negligible amounts of NO (Denis, 1994). For this reason, iNOS involvement in AD pathology, as recently proposed by Meda et al. (1995), remains uncertain. In order to compare responses of human cells to those of rat, human microglia was isolated from normal adult brains recovered rapidly at autopsy, (Giulian et al., 1995a,b). These human brain mononuclear cells behaved as did the rat microglia, engulfing neuritic/core plaques and retracting processes (Giulian et al., 1995a). Both the synthetic A$\beta$ peptides and native plaque fractions S3, S4, and S5 induced human microglia to become neurotoxic (FIGS. 25A and 25B) in patterns identical to those of rat microglia Although A$\beta$1–40 and A$\beta$1–42 were very potent inducers of neurotoxic human microglia, these peptides did not bring about release of nitrate or nitrites (FIGS. 25C and 25D). Neither A$\beta$ exposure to rat microglia nor LPS exposure to human microglia elicited nitrate or nitrite levels above 1.5 $\mu$M. Such observations argue against involvement of microglial iNOS in the neuronal pathology of AD. Overall, human and rat microglia responded identically to A$\beta$, both exhibiting neurotoxicity when in culture with intact human A$\beta$1–42 or A$\beta$1–40 peptide (FIG. 25E).

A$\beta$ as an Indirect Neurotoxin

Figure 26A:
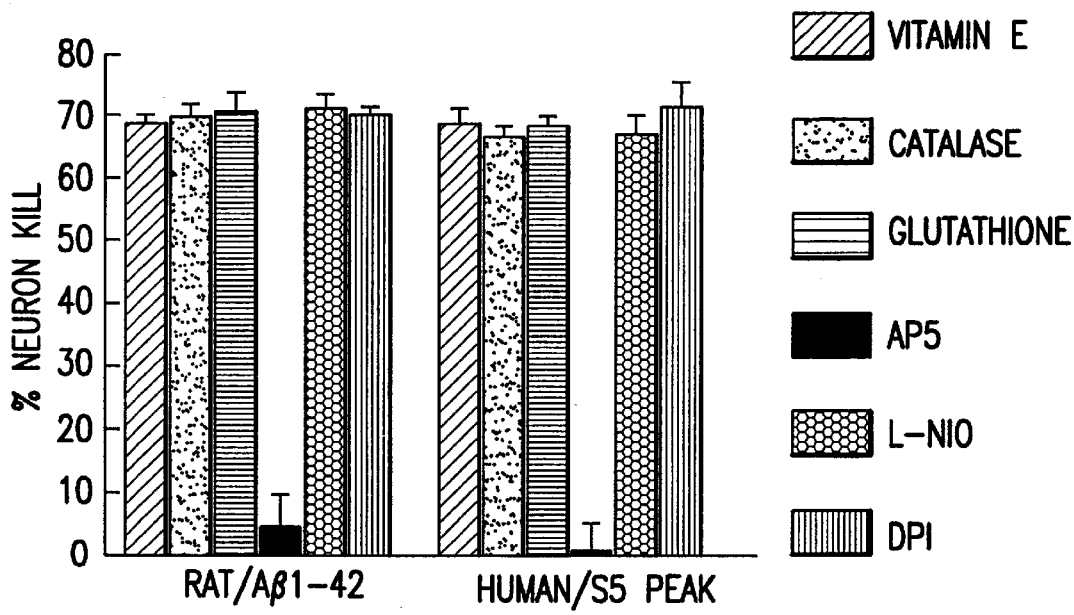
FIGS. 26A–C displays drug blockade of Aβ induced neuron killing by rat and human microglia. To investigate mechanisms of cell killing, rat microglia were stimulated with 1 μmole/1 Aβ1–42 (Rat/Aβ1–42) and human cells with fraction S5 (containing 250 nmole/1 of native Aβ1–42) from solubilized neuritic/core plaques (Human/S5 Peak).
Figure 26B:
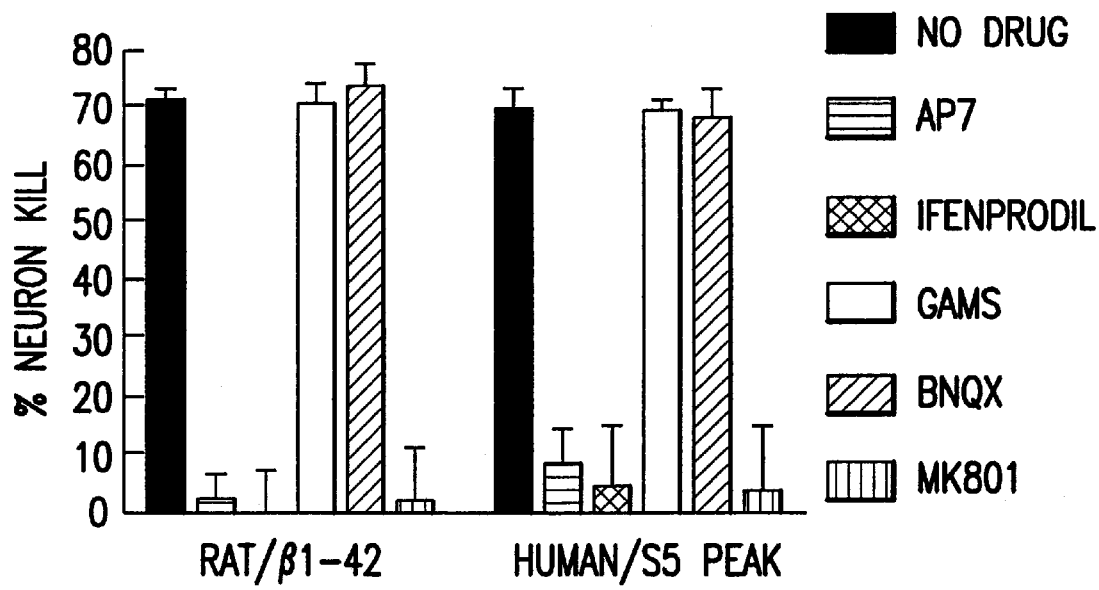

A number of cytotoxic factors have been reported to participate in A$\beta$ neurotoxicity, including radicals (Behl et al., 1994), nitric oxide (Meda et al., 1995), cytokines (Mrak et al., 1995), and NMDA-like molecules (Giulian et al., 1995a). To determine if short-lived factors play a role in A$\beta$ induced neuron killing microglia, neuronal loss was compared when microglia were either mixed among neurons (contact) or separated from neurons by placement in filter bottomed Millex-cell chambers (no contact). A$\beta$1–40 and 1–42, as well as the native plaque fractions, stimulated microglia to destroy neurons despite segregation of microglia and neurons. These observations rule out involvement of short-lived free radical intermediates, since such agents required close proximity between secretory and target cells. Moreover, there was no reduction of microglia-mediated neuron killing after exposure of either human or rodent cells to A$\beta$ upon incubation with such free radical scavengers as vitamin E, catalase, or glutathione or with such potent inhibitors of INOS as diphenyl iodonium (DPI) or L-N-5-(1-imino-ethyl)-ornithine hydrochloride (L-NIO; FIG. 26A). Although glutamate antagonists acting upon non-NMDA receptor sites did not protect neurons, NMDA receptor antagonists (FIG. 26B) including A$\beta$5, AP7, MK-801, and ifenprodil prevented neuronal loss when applied at low concentrations (10 $\mu$M).

Figure 26C:
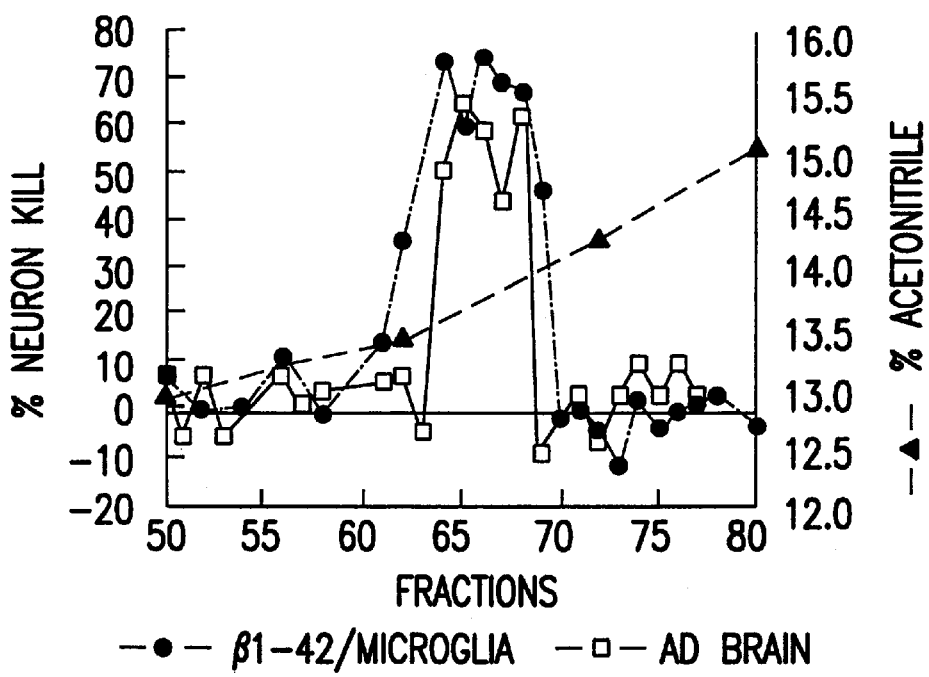

The neurotoxin recovered from A$\beta$1–40 or A$\beta$1–42 stimulated human microglia withstood boiling, showed a low molecular mass (<1000 daltons), extracted into ethyl acetate at pH 10.5, and bound to cationic exchangers such as SP-Sephadex C25, as described for plaque exposed microglial toxin in previous work (Giulian et al., 1995a). Each of these properties is shared by the neurotoxic phenolic amine which can be extracted from AD brain. Inactivation of both the microglia-derived and brain-derived neurotoxin by PFPA, fluorescamine, and plasma amine oxidase suggested the presence of a terminal amine group at the active site while insensitivity to acidified butanol esterification indicated a lack of carboxy groups (Giulian et al., 1995a). Overall, the active principal derived from A$\beta$-stimulated microglia exhibited properties identical to those of the neurotoxin recovered from AD gray matter or from culture media of plaque-stimulated microglia (Giulian et al., 1995a). Protease insensitivity and resistance to acid hydrolysis (6 N HCl, 105° C., 24 hrs) of the neurotoxin ruled out peptide factors, including cytokines and A$\beta$. Co-elution on tandem ion exchange columns confirmed the identical character of microglia-derived and AD brain-derived lipophilic killing factor. As shown in FIG. 26C, a single peak of biologic activity from A$\beta$-stimulated microglia co-eluted with the toxin extracted from AD brain by RP-HPLC. Previous study has shown that this purified agent was an effective toxin against hippocampal neurons in vitro or in vivo in the picomolar range (Giulian et al., 1995a).

Specific a Domains Bind to Microglia

Figure 27A:
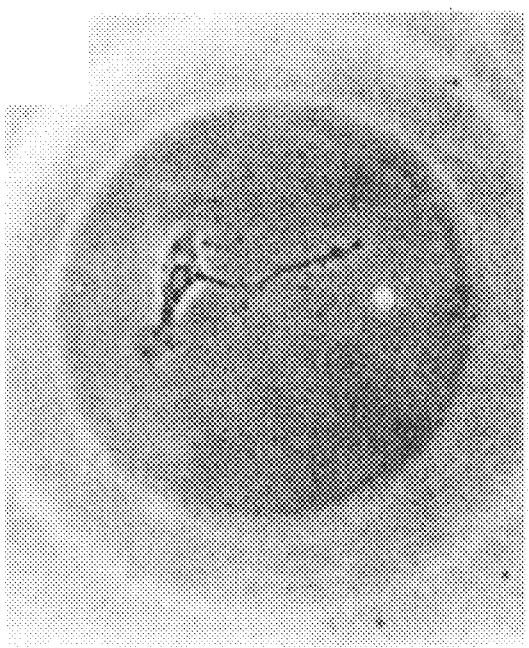
FIGS. 27A–27C depicts Aβ domains and interactions with microglia.
Figure 27B:
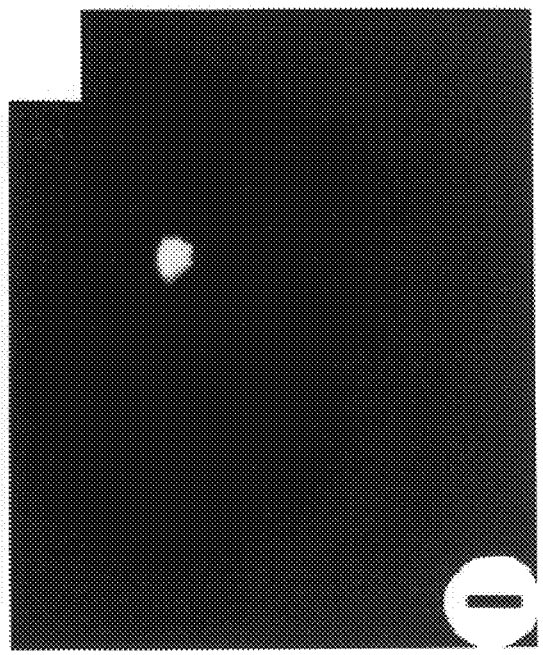
Figure 27C:
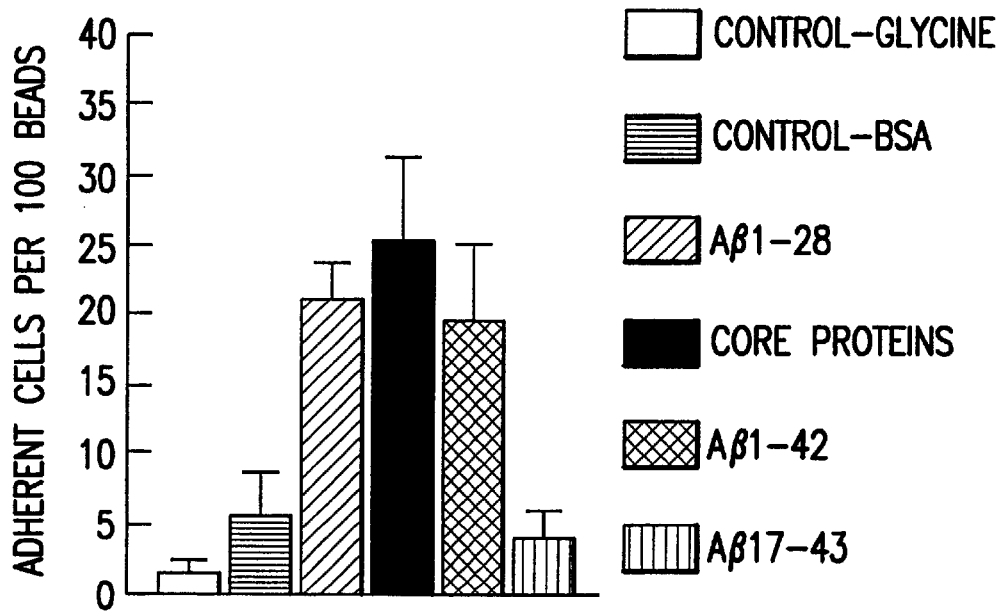

How A$\beta$ peptides might activate microglia is addressed herein. Because adherence to plaques might serve as an important first step in the recruitment of reactive glia, it was reasonable to consider A$\beta$ as a potential anchoring site for microglia upon plaque surfaces. To test this hypothesis, synthetic A$\beta$ peptides or native plaque-derived proteins were covalently coupled to 90 micron Sepharose beads. These beads were then floated atop cultured dishes. Within 30 min, microglia began to detach from the culture dish and anchored to beads which were covalently coupled to native plaque proteins or synthetic A$\beta$1–42 (FIGS. 27A and 27B). Within 6 hours, the number of microglia adhering to plaque-protein-coated beads had increased by 5-fold when compared to cells adhering to control beads coupled to glycine or BSA (FIG. 27C). Interestingly, A$\beta$ peptides which contained N-terminal residues, such as A$\beta$1–28, also promoted cell binding, while the C-terminal portion (A$\beta$17–43) did not (FIG. 27C).

Figure 28G:
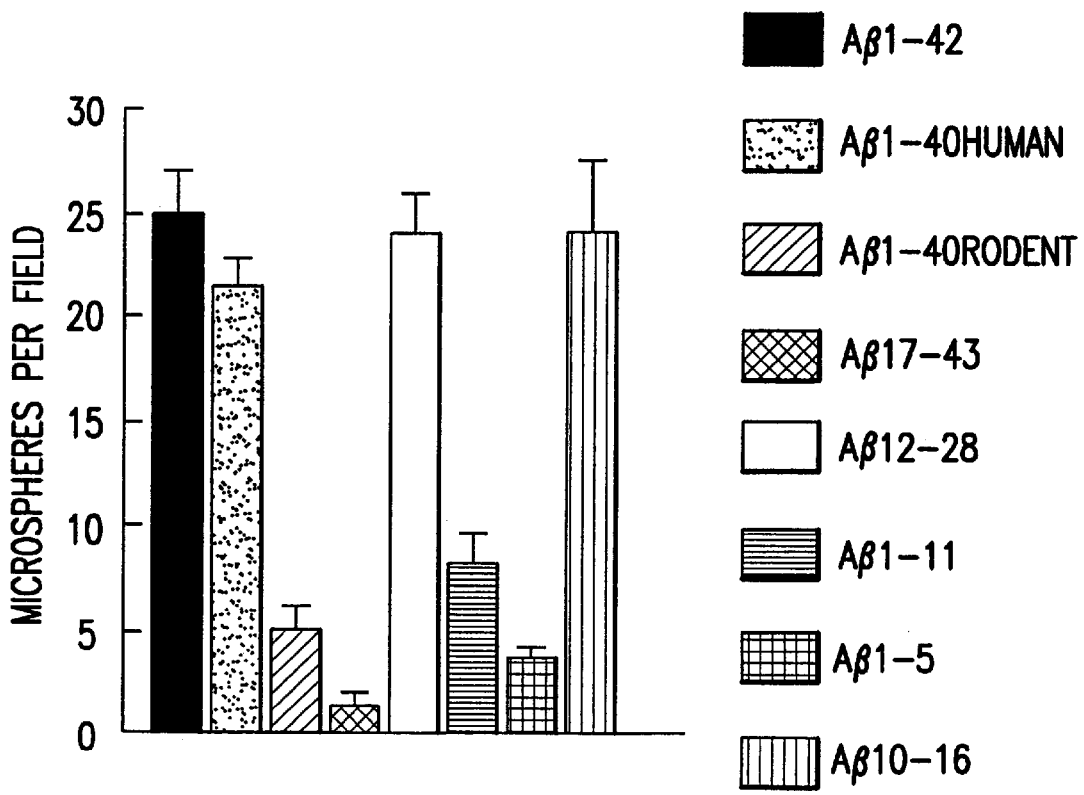

To delineate further which portions of the A$\beta$ peptide served as a microglial binding site, a variety of synthetic peptides coupled to 1 micron diameter microspheres was next compared. Within 4 hours of incubation, marked glial binding to microspheres coupled to A$\beta$1–42, A$\beta$1–40, A$\beta$1–16, or A$\beta$12–28 occurred (FIGS. 28A through 28F), with little cell binding of spheres coupled to A$\beta$17–43, A$\beta$25–35, A$\beta$36–42, or to rodent A$\beta$1–40 ($5_{Arg-Gly}$, $10_{Tyr-Phe}$, $13_{His-Arg}$) was observed. Since structural differences between the human and rodent forms of A$\beta$ occur between residues 5 and 13 of the N-terminus, properties of this specific domain were focused upon. As shown in FIG. 28G, A$\beta$12–28-microspheres provided an anchoring substrate for cells whereas A$\beta$1–11 did not. Examination of a heptapeptide confirmed a microglial binding domain between residues I 0 to 16 (FIG. 28G).

Figure 29A:
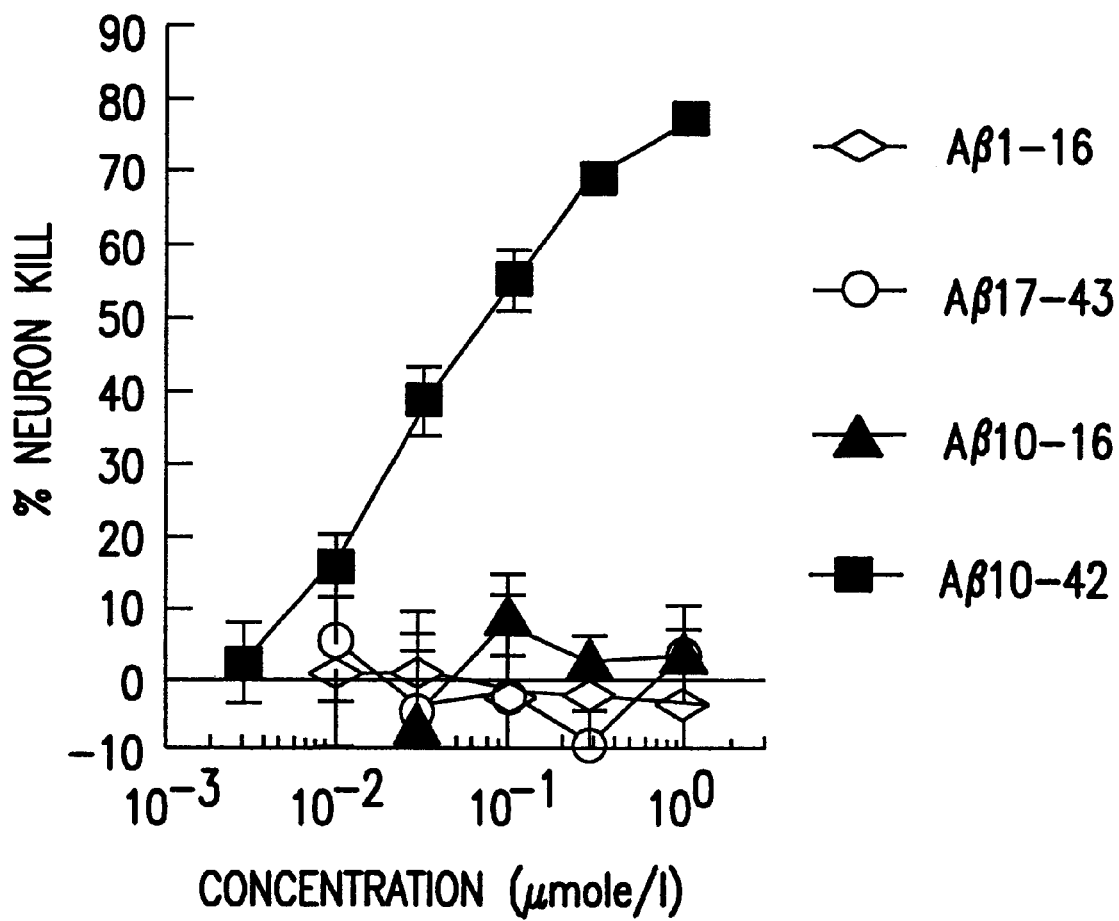
Figure 29B:
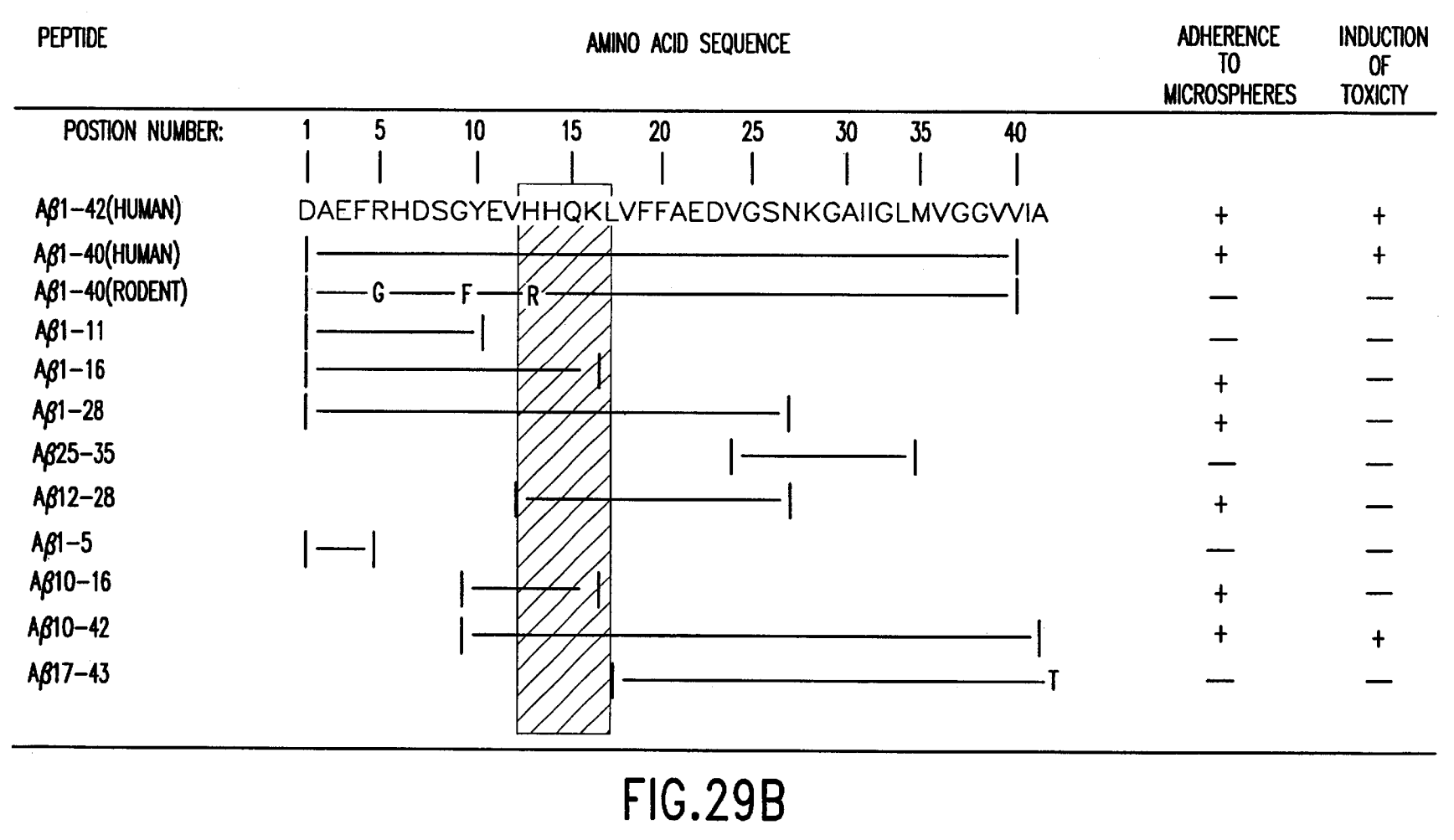

The importance of the N-terminal cell binding domain for A$\beta$-microglial interactions was supported by the fact that neither A$\beta$17–43 nor A$\beta$1–40$_{rodent}$ induced neurotoxic cells despite test concentrations 100-fold above that required for human AP 1–40 (FIGS. 21E and 25E). The patterns of binding and toxicity predicted that the 10 to 16 binding region would be necessary component for activation of neuron-killing microglia. To test this hypothesis, A$\beta$1O-42 was next incubated at increasing concentrations and found it to be nearly as potent as A$\beta$1–42 in eliciting microglia-dependent killing of cells (FIGS. 21E and 29A). However, the Aβ10-16 binding domain or the 17–43 region by themselves did not injure neurons (FIG. 29A). Thus, the N terminus of human Aβ (particularly residues 10–16) was necessary, though not sufficient, for eliciting neurotoxic microglia (FIG. 29B).

The disclosure of each patent, patent application and publication cited or described in this document is hereby incorporated herein by reference, in its entirety.

Various modifications of the invention in addition to those shown and described herein will be apparent to those skilled in the art from the foregoing description. Such modifications are also intended to fall within the scope of the appended claims.

TABLE 1

Characterization of Protein Fractions Derived From Neuritic/Core Plaques

| Fraction | Major constituents | Aβ Concentrations Added to Culture (nmoles/liter; Aβ1-40, Aβ1-42) |
|---|---|---|
| S1 | ACT[1], apoE, glycoproteins | 0.1, 0.1 |
| S2 | apoE, glycoproteins | 0.1, 3.2 |
| S3 | Aβ trimers[1], glycoproteins | 2.0, 54.5 |
| S4 | Aβ dimers[1] | 1.4, 220 * |
| S5 | Aβ monomers1 | 1.0, 250 * |

[1]Roher et al., 1993b.

Major components are estimated to be ≧ 30% of protein. Final Aβ concentrations used in neuron culture assays were based upon ELISA mesurements as described in METHODS. Due to the aggregation of material in the S4 and S5 peaks, Aβ concentrations* were estimated using both amino acid analysis and ELISA for the Aβ1–40 and Aβ1–42 peptides. ACT = β-1- antichymotrypsin; apoE = apolipoprotein E;

TABLE 2

Properties of Aβ Peptides

| | Principal Location | Solubility | Elicits Neurotoxic Microglia |
|---|---|---|---|
| Aβ1-28 | synthetic | soluble | — |
| Aβ12-28 | synthetic | soluble | — |
| Aβ17-42 | diffuse deposits | very insoluble | — |
| Aβ25-35 | synthetic | soluble | — |
| Aβ1-40 | normal brain normal CSF vascular deposits neuritic/core plaques | moderately soluble | + |
| Aβ1-42 | neuritic/core plaques | very insoluble | + |

Properties and sources of amyloid peptides. Three major Aβ forms are known to occur in brain tissue, Aβ17–42, 1–40, and Aβ1–42. Solubility of peptides is described for chemically-defined culture media at 37° C. Aβ1–42 is the most potent stimulus for neurotoxic microglia (see FIG. 17E) and represents the major insoluble component of neuritic and core plaques.

REFERENCES

U.S. Pat. No. 4,683,195
U.S. Pat. No. 4,683,202
U.S. Pat. No. 4,800,159
GB Application No. 2 202 328
EPa. No. 320,308
European Pat. Application Publication No. 329,822
PCT Application No. PCT/US87/00880
PCT Application WO 88/10315
PCT Application No. PCT/US89/01025
PCT Application WO 89/06700

Banati R B, Gehrmann J, Schubert P, Kreutzberg G W (1993) Cytotoxicity of microglia. Glia 7:111–118.

Bansal R, Warrington A E, Gard A L, Ranscht B, Pfeiffer S E (1989) Multiple and novel specificities of monoclonal antibodies 01, 04, and R-mAb used in the analysis of oligodendrocyte development. J Neurosci Res 24:548–557

Beckman J S, Beckman, T, Chen J, Marshall P A, and Freeman, B A (1990) Apparent hydroxyl radical production by peroxymitratie: implications for endothelial injury from nitric oxide and superoxide. Proc Natl Acad Sci. 87:1620–1627.

Beppu, M., Hora, M. & Kikugawa, K. Biol. Pharmaceut. Bull. 17,39–46 (1994).

Belil C. Davis J B, Lesley R, Schubert D (1994) Hydrogen peroxide mediates amyloid β protein toxicity. Cell 77:817–827.

Bolsi D (1927) Placche senile e microglia. Riv di Pat Nerv Ment 32: 65–72.

Breitner J C S, Gau B A, Welsh K A (1990) Inverse association of anti-inflammatory treatments and Alzheimer's disease: Initial results of a co-twin control study. Neurology 44:227–232.

Brunden, K. R., Richter-Cook, N. J., Chaturvedi, N. & Frederickson, R. C. J. Neurochem. 61,2147–2154 (1993).

Bu'ee, L., Ding, W., Delacourte, A. & Fillit, H. Brain Res. 601, 154–163 (1993).

Christie, R. H., Freeman, M. & Hyman, B. T. Am. J Pathol 148, 3 99–403 (1996).

Cotman C W, Pike C J, Copani A (1992) β-Amyloid neurotoxicity: A discussion of in vitro findings. Neurobiol Aging 13:587–590.

Davies P (1994) Neuronal abnormalities, not amyloid, are the cause of dementia in Alzheimer disease. In: Alzheimer disease (Terry R D, Katzman R, Bick K L, eds), pp 327–333. New York: Raven Press.

Davis T L, Wiley R G (1989) Immunotoxin, OX-42-saporin, destroys cerebellar Purkinje cells after intraventricular injection in rats. Brain Res 504:216–222.

Denis M (1994) Human monocytes/macrophages: NO or no NO? J Leukoc Biol 55:682–684.

Eikelenboom P, Zhan S-S, van Gool W A, Allsop D (1994) Inflammatory mechanisms in Alzheimer's disease. TIPS 15:447–450.

Fraser P E, Nguyen J T, Inouye H, Surewicz W X, Selkoe D J, Podlisney M B, Kirschner D A (1992) Fibril formation by primate, rodent, and Dutch-hemorrhagic analogues of Alzheimer amyloid protein. Biochem 31:10716–10723.

Fraser, P. E., Nguyen, J. T., McLachlan, D. R., Abraham, C. R. & Kirschner, D. A. J Neurochem. 61, 298–305 (1993).

Fraser, P. E., et al. Journal of Molecular Biology 244, 64–73 (1994).

Games D, Khan K M, Soriano F G, Keim P S, Davis D L, Bryant K, Lieberburg I (1992) Lack of Alzheimer pathology after 0-amyloid protein injections in rat brain. Neurobiol Aging 13:569576.

Gennaro, Alfonso, ed., Remington's Pharmaceutical Sciences, 18th Edition, 1990, Mack Publishing Co., Easton Pa.

Giaccone G, Tagliavini F, Linoli G, Bouras C, Frigerio L, Frangione B, Bugiani 0 (1989) Down patients: extracellular preamnyloid deposits precede neuritic degeneration and senile plaques. Neurosci Lett 97:232–238.

Giulian D (1992) Microglia and diseases of the nervous system. In: Current Neurology, Vol. 12 (Appel SH, ed), pp 23–54. St. Louis: Mosby-Year Book, Inc.

Giulian D, Baker T J (1986) Characterization of ameboid microglia isolated from developing mammalian brain. J Neurosci 6:2163–2178.

Giulian D, Robertson C (1990) Inhibition of mononuclear phagocytes reduces ischemic injury in the spinal cord. Ann Neurol 27:33–42.

Giulian D., Chen J, Ingeman J E, George J, Noponen M (1989) The role of mononuclear phagocytes in wound healing after traumatic injury to the adult mammalian brain. J Neurosci 9:4416–4429.

Giulian D, Vaca K, Corpuz M (1993a) Brain glia release factors with opposing actions upon neuronal survival. J Neurosci 13:29–37.

Giulian D, Corpuz M, Chapman S, Mansouri M, Robertson C (1993b) Reactive mononuclear phagocytes release neurotoxins after ischemic and traumatic injury to the central nervous system. J Neurosci Res 36:681–693.

Giulian D, Li J, Xi J, George J, Rutecki P (1994) The impact of microglia-derived cytokines upon gliosis in the CNS. Dev Neurosci 16:128–136.

Giulian D, Haverkamp L J, Li J, Karshin W L, Yu J, Tom D, Li X, Kirkpatrick J B (1995a) Senile plaques stimulate microglia to release a neurotoxin found in Alzheimer brain. Neurochem Int 27:119–137.

Giulian D, Li J, Bartel S, Broker J, Li X, Kirkpatrick J B (1995b) Cell surface morphology identifies microglia to be a distinct class of mononuclear phagocytes. J Neurosci 15:77127726.

Harris, M E, Carney J M, Cole P S, Hensley K, Howard B J, Martin L, Bununer P, Wang Y, Pedigo N W Jr, Butterfield D A (1995) 0-amyloid peptide derived, oxygen dependent free radicals inhibit glutamate uptake in cultured astrocytes: implications for Alzheimer's disease. NeuroReport 6:1875–1879.

Hensley K, Carney J M, Mattson M P, Aksenova M, Harris M, Wu J F, Floyd R A, Butterfield D A (1994) A model for β-amyloid aggregation and neurotoxicity based on free radical generation by the peptide: relevance to Alzheimer disease. Proc Natl Acad Sci 91:3270–3274.

Howlett D R, Jennings K H, Lee D C, Clark M S G, Brown F, Wetzel R, Wood S J, Camilleri P, Roberts G W (1995) Aggregation state and neurotoxic properties of Alzheimer beta-amyloid peptide. Neurodegeneration 4:23–32.

Hunter, M. J. & Ludwig, M. L. *Meth. Enzymol.* 25, 585–596 (1972).

Ignarro L J (1990) Nitric oxide. Hypertension 16:477–483.

Kallapur S. G. & Akeson R. A. *J Neurosci. Res.* 35, 538–548 (1992).

Koh J Y, Yang L L, Cotman C W (1990) β-amyloid protein increases the vulnerability of cultured cortical neurons to excitotoxic damage. Brain Res 533:315–320.

Kohler and Milstein, (1975) *Nature* 256:495.

Koo Eli, Park, L., and Selkoe D J (1993) Amyloid β-protein as a substrate interacts with extracellular matrix to promote neurite outgrowth. Proc Natl Acad USA 90:47448–4752.

Kuo Y-M, Ernmerlings M R, Vigo-Pelfrey C, Kasunic T C, Kirkpatrick J B, Murdoch G H, Ball M J, Roher A E (1996) Water-soluble Aβ (N-40, N-42) oligomers in normal and Alzheimer disease brains. J Biol Chem 271:40774081.

Lees G J (1993) Nitric oxide is produced by microglia. J Neurol Sci 1 14:119–122.

Lorenzo A, Yankner B A (1994) Beta-amyloid neurotoxicity requires fibril formation and is inhibited by congo red. Proc Natl Acad Sci USA 91:12243–12247.

Lucca U, Tettamanti M, Forloni G, Spagnoli A (1994) Nonsteroidal anti-inflammatory drug use in Alzheimer's disease. Biol Psychiat 36:854–856.

Masliah E, Terry R D, Mallory M, Alford M, Hansen L A (1990) Diffuse plaques do not accentuate synapse loss in Alzheimer's disease. Am J Pathol 137:1293–1297.

Maslia E, Mallory M, Deerinck T, DeTeresa R, Lamont S, Miller A, Terry R D, Carragher B, Ellisman M (1993) Re-evaluation of the structural organization of neuritic plaques in Alzheimer's disease. J Neuropathol Exp Neurol 52:619–632.

Mattson M P, Rydel R E (1992) β-amyloid precursor protein and Alzheimer's disease: The peptide plot thickens. Neurobiol Aging 13:617–621.

Mattson M P, Cheng B, Davis D, Bryant K, Lieberburg I, Rydel R E (1992) β-amyloid peptides destabilize calcium homeostasis and render human cortical neurons vulnerable to excitotoxicity. J Neurosci 12:376–389.

May P C, Gitter B D, Waters D C, Simmons L K, Becker G W, Small J S, Robison P M (1992) β-amyloid peptide in vitro toxicity: Lot-to-lot variability. Neurobiol Aging 13:605–607.

McGeer P L, Itagaki S, Boyes B E, McGeer E G (1987) Reactive microglia in patients with senile dementia of the Alzheimer type are positive for the histocompatibility glycoprotein HLADR. Neurosci Lett 79:195–200.

McGeer P L, McGeer E, Rogers J, Sibley J (1990) Anti-inflammatory drugs and Alzheimer disease. Lancet 335:1037.

Meda L, Cassatella M A, Szendrel G I, Otvos L, Jr, Baron P, Villalba M, Ferrari D, Rossi F (1995) Activation of microglial cells by β-amyloid protein and interferon-γ. Nature 374:647650.

Miles, E. W. *Meth. Enzymol.* 47,431–442 (1977).

Mirra S, Heyman A (1993) CERAD guide to the neuropathological assessment of Alzheimer's disease and other dementias. Decatur, Ga.: CERAD.

Mrak R E, Sheng J G, Griffin W S T (1995) Glial cytokines in Alzheimer's Disease: Review and pathogenic implications. Hum Pathol 26:816–823.

Narindrasorasak, S., Lowery, D., Gonzalez-DeWhitt, P., Poorman, R. A., Greenberg, B.& Kisilevsky, R. *J Biol. Chem.* 266, 12878–12883 (1991).

Patthy, L. & Smith, E. L. *J Biol Chem.* 250, 557–564 (1975).

Perlmutter L S, Scott S A, Barron E, Chui H C (1992) MHC class II-positive microglia in human brain: association with Alzheimer lesions. J Neurosci Res 33:549–558.

Piani D, Frei K, Do K, Cu'enod M, Fontana A (1991) Murine brain macrophages induce NMDA receptor mediated neurotoxicity in vitro by secreting glutamate. Neurosci Lett 133:159–162.

Pike C J, Walencewicz A J, Glabe C G, Cotman C W (1991) Aggregation-related toxicity of synthetic b-amyloid protein in hippocampal cultures. Eur J Pharmacol 207:367–368.

Pike C J, Burdick D, Walencewicz A J (1993) Neurodegeneration induced by beta-amyloid peptides in vitro: the role of peptide assembly state. J Neurosci 13:1676–1687.

Pike C J, Overman M J, Cotman C W (1995) Amino-terminal deletions enhance aggregation of beta-amyloid peptides in vitro. J Biol Chem 270:23895–23898.

Podlisny M B, Stephenson D T, Frosch M P, Lieberburg I, Clemens J A, Selkoe D J (1992) Synthetic amyloid β-protein fails to produce specific neurotoxicity in monkey cerebral cortex. Neurobiol Aging 13:561–567.

Pollack S J, Sadler I I J, Hawtin S R, Tailor V J, Shearman M S (1995) Sulfonated dyes attenuate the toxic effects of β-amyloid in a structure specific fashion. Neurosci Lett 197:211–214.

Price D L, Borchelt D R, Walker L C, Sisodia S S (1992) Toxicity of synthetic Aβ peptides and modeling of Alzheimer's disease. Neurobiol Aging 13:623–625.

Rio-Hortega P.(1932) Microglia. In: Cytology and cellular pathology of the nervous system (Penfield W, ed), pp 481–584. New York: Hocker, Inc.

Riordan, J. F. & Vallee, B. L. *Meth. Enymol* 25, 551–521 (1972).

Rogers J, Luber-Nardo J, Styren S D, Civin W H (1988) Expression of immune system-associated antigens by cells of the human central nervous system: relationship to the pathology of Alzheimer's disease. Neurobiol Aging 9:339–349.

Rogers J, Cooper N R, Webster S, Schultz J, McGeer P L, Styren S D, Civin W H, Brachova L, Bradt B, Ward P, Lieberburg I (1992) Complement activation by β-amyloid in Alzheimer disease. Proc Natl Acad Sci USA 89:10016–10020.

Roher A E, Palmer K C, Chau V, Ball M J (1988) Isolation and characterization of Alzheimer's disease paired helical filament cytoskeletons: Differentiation from amyloid plaque core protein. J Cell Biol 107:2703–2716.

Roher A E, Lowenson J D, Clarke S, Wolkow C, Wang R, Cotter R J, Reardon I M, Zurcher-Neely H A. Heinrikson R L, Ball M J, Greenberg B D (1993a) Structural alterations in the peptide backbone of β-amyloid core protein may account for its deposition and stability in Alzheimer's disease. J Biol Chem 268:3072–3083.

Roher, A E, Palmer K C, Yurewicz E C, Ball M J, Greenberg B D (1993b) Morphological and biochemical analyses of amyloid plaque core proteins purified from Alzheimer disease brain tissue. J Neurochem 61:1916–1926.

Schnabel, J. (1993) New Alzheimer's therapy suggested. Science 260:1719–1720.

Schrode, J.& Folk, J. E. J Biol Chem.253,4837–4840 (1978).

Selkoe, D. J. (1991) The molecular pathology of Alzheimer's disease. Neuron 6:487–498.

Simmons L K, May P C, Tamaselli K J, Rydel R E, Fuson K S, Brigham E F, Wright S, Lieberburg I, Becker G W, Brems D N, Li W Y (1994) Secondary structure of amyloid β peptide correlates with neurotoxic activity in vitro. Mol Pharmacol 45:373–379.

Sommer I, Schachner M (1981) Monoclonal antibodies (01 to 04) to oligodendrocytes cell surfaces: an immunocytological study in the central nervous system. Develop Biol 83:311327.

Stephenson D T and Clemens J A (1992) In vivo effects of β-amyloid implants in rodents: lack of potentiation of damages associated with transient global ischemia. Brain Res 586:235–246.

Terry R D, Katzman R, Bick K L, eds (1994a) Alzheimer's disease. New York: Raven Press.

Terry R D, Masliah E, Hansen L A (1994b) Structural basis of the cognitive alterations in Alzheimer disease. In: Alzheimer disease (Terry R D, Katzman R, Bick K L, eds), pp 179–196. New York: Raven Press.

Thery C, Chamak B, Mallat M (1991) Free radical killing of neurons. Eur J Neurosci 3:115–1164.

Verga L, Frangione B, Tagliavini F, Giaccone G, Migheli A, Bugiani O (1989) Alzheimer's disease and Down patients: cerebral preamyloid deposits differ ultrastructurally and histochemically from the amyloid of senile plaques. Neurosci Lett 105:294–299.

Whitson J S, Selkoe D J, Cotman C W (1989) Amyloid β protein enhances the survival of hippocampal neurons in vitro. Science 243:1488–1490.

Wu, D. Y. et al., 1989.

Wujek J R, Dority M D, Frederickson R C A, and Brudent K R (1996) Deposits of Aβ fibrils are not toxic to cortical and hippocampal neurons in vitro. Neurobiol Aging 17:107–113.

Yamaguchi H. Hirai S, Morimatsu M, Shoji M, Harigaya Y (1988) Diffuse type of senile plaques in the brains of Alzheimer-type dementia. Acta Neuropathol 77:113–119.

Yankner B A, Mesulam M-M (1991) Seminars in medicine of the Beth Israel Hospital, Boston: βAmyloid and the pathogenesis of Alzheimer's disease. N Engl J Med 325:1849–1857.

Yankner B A, Duffy L K, Kirschner D A (1990) Neurotrophic and neurotoxic effects of amyloid protein: reversal by tachykinin neuropeptides. Science 250:279–282.

Younkin SG (1995) Evidence that Aβ42 is the real culprit in Alzheimer's disease. Ann Neurol 37:287–288.

What is claimed is:

1. A method of screening for an agent that inhibits the effect on a neuron of a neurotoxin from a mononuclear phagocyte activated by β-amyloid or fragments of β-amyloid, wherein said fragments at a concentration of from about 0.001 to about 1 μmole/liter induce significant neuron injury in neuron cultures containing microglia as compared to neuronal injury in cultures lacking microglia, said method comprising:

contacting a monuclear phagocyte with β-amyloid or said fragments of β-amyloid effective to activate said mononuclear phagocyte to produce a neurotoxin, wherein said neurotoxin has a molecular mass of less than 1000 daltons, lacks peptide bonds, and is isolatable in aqueous solution from tissue or tissue culture media in active form;

separating said neurotoxin from said mononuclear phagocytes; and contacting a culture of neurons with an amount of said neurotoxin effective to produce a disruption of neuron cell metabolism in the neurons in the presence of an agent suspected of inhibiting the effect of the neurotoxin, wherein a decrease in disruption of neuronal cell metabolism in the presence of said agent compared to a culture lacking said agent is indicative of an agent that inhibits the effect on a neuron of a neurotoxin from said activated mononuclear phagocyte.

2. A method of screening for an agent that inhibits the effect on a neuron of a neurotoxin from a neurotoxic mononuclear phagocyte activated by β-amyloid or fragments of β-amyloid, wherein said fragments at a concentration of from about 0.001 to about 1 μmole/liter induce significant neuron injury in neuron cultures containing microglia as compared to neuronal injury in cultures lacking microglia, sad method comprising:

contacting a mononuclear phagocyte with βamyloid or said fragments of β-amyloid effective to activate said mononuclear phagocyte to produce a neurotoxic mononuclear phagocyte, wherein said neurotoxin has a molecular mass of less than 1000 daltons, lacks peptide bonds, and is isolatable in aqueous solution from tissue or tissue culture media in active form;

separating said neurotoxin from said mononuclear phagocytes;

contacting tissue or cell culture containing neurons with said neurotoxin produced by said mononuclear phagocyte in an amount effective to produce a disruption of neuron cell metabolism in said neurons, and with an agent suspected of inhibiting the effect of said neurotoxin an a neuron, and utilizing a neuron specific marker to identify neurons in said tissue or culture, wherein a disruption of neuron cell metabolism as indicated by changes in the neuron-specific marker;

and further wherein a decrease in disruption of neuron cell metabolism in the presence of said agent compared to a tissue or culture lacking said agent is indicative of an agent that inhibits the effect on a neuron of a neurotoxin from said neurotoxic mononuclear phagocyte.

3. A method of screening for an agent that inhibits the effect on a neuron of a neurotoxin from a mononuclear phagocyte activated by β-amyloid or fragments of β-amyloid, wherein said fragments at a concentration of from about 0.001 to about 1 μmole/liter induce significant neuron injury in neuron cultures containing microglia as compared to neuronal injury in cultures lacking microglia, said method comprising:

contacting a mononuclear phagocyte with β-amyloid or said fragments of β-amyloid effective to activate said mononuclear phagocyte to produce a neurotoxin, wherein said neurotoxin has a molecular mass of less than 1000 daltons, lacks peptide bonds, and is isolatable in aqueous solution from tissue or tissue culture media in active form;

separating said neurotoxin from said mononuclear phagocytes; and contacting a culture of neurons with an amount of the neurotoxin effective to produce injury or death in the neurons in the presence of an agent suspected of inhibiting the effect of the neurotoxin, when injury or death in the neurons is detected by obtaining an image of the culture;

and further wherein a decrease in death or injury to neurons as compared to cultures lacking the agent, is indicative of an agent that inhibits the effect on a neuron of a neurotoxin from said activated mononuclear phagocyte.

4. A method of screening for an agent that inhibits the effect on a neuron of a neurotoxin from a neurotoxic mononuclear phagocyte activated by β-amyloid or fragments of β-amyloid, wherein said fragments at a concentration of from about 0.001 to about 1 μmole/liter induce significant neuron injury in neuron cultures containing microglia as compared to neuronal injury in cultures lacking microglia, said method comprising:

contacting a mononuclear phagocyte with β-amyloid or said fragments of β-amyloid effective to activate said mononuclear phagocyte to produce a neurotoxic mononuclear phagocyte, wherein said neurotoxin has a molecular mass of less than 1000 daltons, lacks peptide bonds, and is isolatable in aqueous solution from tissue or tissue culture media in active form;

separating said neurotoxin from said mononuclear phagocytes;

contacting a tissue or cell culture containing neurons with an amount of said neurotoxin effective to produce injury or death in the neurons in the presence of an agent suspected of inhibiting the effect of the neurotoxin; and utilizing a neuron specific marker to identify neurons in the tissue or culture, wherein injury or death in said neurons is detected by obtaining an image of the tissue or culture;

and further wherein a decrease in neuron injury or death compared to a tissue or culture lacking the agent is indicative of an agent that inhibits the effect on a neuron of a neurotoxin from said neurotoxic mononuclear phagocyte.

5. A method of claim 1, 2, 3 or 4 wherein said neurotoxin is NTox.

6. A method of claim 1, 2, 3 or 4 wherein said agent is a neurotoxin blocker.

7. A method of claim 6 wherein said neurotoxin blocker is selected from tyramine and a tyramine-like agent.

8. A method of claim 1, 2, 3 or 4 wherein said β-amyloid or said fragments of β-amyloid are adhered to a microsphere, vesicle, microbubble, polymeric bead, or liposome.

9. A method of claim 1, 2, 3 or 4 wherein said β-amyloid or said fragment of β-amyloid is adhered to a solid support and is infused into a mammalian brain selected from the group consisting of primate, rodent, guinea pig, dog, cat, rabbit, and pig.

10. A method of claim 1 or 2 wherein said neuron metabolism is selected from the group consisting of metabolism of glucose, the production of ATP, maintenance of ion gradients across a cell membrane, protein synthesis, nucleic acid synthesis, and mitochondrial respiration.

11. A method of claim 1 or 2 wherein said disruption of neuron metabolism includes amplified nucleic acids from said neuron.

12. A method of claim 1, 2, 3 or 4 wherein said activation is associated with a disease selected from the group consisting of Alzheimer's Disease, hereditary hemorrhage with amyloidosis-Dutch type, cerebral amyloid angiopathy, and Down's syndrome.

13. A method of claim 1, 2, 3 or 4 wherein said neurotoxin is associated with a subject at risk for or suffering from Alzheimer's Disease.

14. A method of screening for an agent that inhibits the effect on a neuron of a neurotoxin from a mononuclear phagocyte activated by β-amyloid or fragments of β-amyloid, wherein said fragments at a concentration of from about 0.001 to about 1 μmole/liter induce significant neuron injury in neuron cultures containing microglia as compared to neuronal injury in cultures lacking microglia, said method comprising:

contacting a mononuclear phagocyte with β-amyloid or said fragments of β-amyloid coupled to a solid support, effective to activate said mononuclear phagocyte to produce a neurotoxin, wherein said neurotoxin has a molecular mass of less than 1000 daltons, lacks peptide bonds, and is isolatable in aqueous solution from tissue or tissue culture media in active form;

separating said neurotoxin from said mononuclear phagocytes; and contacting a culture of neurons, neuron-like cells or cells expressing an NMDA receptor with an amount of said neurotoxin effective to produce a disruption of normal cell metabolism in said neurons, neuron-like cells or cells expressing an NMDA receptor in the presence of an agent suspected of inhibiting the effect of said neurotoxin, wherein a decrease in disruption of normal neuronal cell metabolism in the presence of said agent compared to a culture lacking said agent is indicative of an agent that inhibits the effect on a neuron of a neurotoxin from said activated mononclear phagocyte.

15. A method of claim 14 wherein said solid support is selected from a microsphere and a polymeric bead.

16. A method of claim 14 wherein said disruption of neuron cell metabolism is detected by detecting amplified nucleic acids from said neuron.

17. A method of claim 14 wherein the indicator of neuron cell metabolism is selected from the group consisting of metabolism of glucose, the production of ATP, maintenance of ion gradients across a cell membrane, protein synthesis, nucleic acid synthesis, and mitochondrial respiration.

18. A method of screening for an agent that inhibits the effect on a neuron of a neurotoxin from a mononuclear phagocyte activated by β-amyloid fragments of β-amyloid, wherein, said fragments at a concentration of from about 0.001 to about 1 μmole/liter induce significant neuron injury in neuron culture containing microglia as compared to neuronal injury in culture lacking microglia, said method comprising:

contacting a mononuclear phagocyte with β-amyloid or said fragments of β-amyloid coupled to a sold support, effective to activate said mononuclear phagocyte to produce a neurotoxin, wherein said neurotoxin has a molecular mass of less than 1000 daltons, lacks peptide bonds, and is isolatable in aqueous solution from tissue or tissue culture media in active form;

separating said neurotoxin from said mononuclear phagocytes;

contacting tissue or cell culture containing neurons with said neurotoxin produced by said mononuclear phagocyte in an amount effective to produce a disruption of neuron cell metabolism in said neurons, and with an agent suspected of inhibiting the effect of said neurotoxin on a neuron, and utilizing a neuron specific marker to identify neurons in said tissue or culture, wherein a disruption of normal cell metabolism is correlated with a disruption of neuron function as indicated by changes in the neuron-specific marker; and further wherein a decrease in disruption of neuron cell metabolism in the presence of said agent compared to a tissue or culture lacking said agent is indicative of an agent that inhibits the effect on a neuron of a neurotoxin from said activated mononuclear phagocyte.

19. A method of claim 18 wherein said β-amyloid or fragments of β-amyloid coupled to said solid support is infused into a mammalian brain selected from the group consisting of primate, rodent, guinea pig, dog, cat, rabbit, and pig.

20. A method of claim 18 wherein said solid support is selected from a microsphere and a polymeric bead.

21. A method of claim 18 wherein said normal neuron metabolism is selected from the group consisting of metabolism of glucose, the production of ATP, maintenance of ion gradients across a cell membrane, protein synthesis, nucleic acid synthesis, and mitochondrial respiration.

22. A method of claim 18 wherein said disruption of neuron cell metabolism is detected by detecting amplified nucleic acids from said neuron.

23. A method of claim 18 wherein said mononuclear phagocyte is selected from the group consisting of a microglial cell, a monocyte, a macrophage, and a microglial precursor cell, monocyte precursor cell, a macrophage precursor cell, microglial-like cell, monocyte-like cell, and macrophage like cell.

* * * * *